US012078630B2

(12) United States Patent
Miller et al.

(10) Patent No.: US 12,078,630 B2
(45) Date of Patent: Sep. 3, 2024

(54) DEVICE FOR THE CAPTURE AND REMOVAL OF DISEASE MATERIAL FROM FLUIDS

(71) Applicant: PATH EX, Inc., Houston, TX (US)

(72) Inventors: Sinead E. Miller, Houston, TX (US); Jeffrey Ransden, Houston, TX (US); Alan Bachman, Houston, TX (US)

(73) Assignee: PATH EX, INC., Houston, TX (US)

( * ) Notice: Subject to any disclaimer, the term of this patent is extended or adjusted under 35 U.S.C. 154(b) by 774 days.

(21) Appl. No.: 16/902,745

(22) Filed: Jun. 16, 2020

(65) Prior Publication Data

US 2020/0378948 A1 Dec. 3, 2020

Related U.S. Application Data

(63) Continuation of application No. PCT/US2019/012403, filed on Jan. 4, 2019.

(60) Provisional application No. 62/614,250, filed on Jan. 5, 2018.

(51) Int. Cl.
*G01N 33/49* (2006.01)
*B01L 3/00* (2006.01)

(52) U.S. Cl.
CPC .......... *G01N 33/492* (2013.01); *B01L 3/5023* (2013.01); *B01L 2300/0854* (2013.01)

(58) Field of Classification Search
CPC ............................ G01N 33/492; B01L 3/5023
See application file for complete search history.

(56) References Cited

U.S. PATENT DOCUMENTS

| | | | |
|---|---|---|---|
| 3,538,744 | A | 11/1970 | Karasek |
| 4,311,589 | A | 1/1982 | Brumfield |
| 4,685,900 | A | 8/1987 | Honard et al. |
| 5,571,410 | A | 11/1996 | Swedberg et al. |
| 6,406,861 | B1 | 6/2002 | Henderson et al. |
| 6,498,007 | B1 | 12/2002 | Adachi et al. |
| 6,533,747 | B1 | 3/2003 | Polaschegg et al. |

(Continued)

FOREIGN PATENT DOCUMENTS

| | | | |
|---|---|---|---|
| CN | 1700009 | A | 11/2005 |
| CN | 103732271 | A | 4/2014 |

(Continued)

OTHER PUBLICATIONS

3D Printed Microfluidic Device for the Detection of Pathogenic Bacteria Using Size-based Separation in Helical Channel with Trapezoid Cross-Section Wonjae Lee, Donghoon Kwon, Woong Choi, Gyoo Yeol Jung, Anthony K Au, Albert Folch, Sangmin Jeon Scientific Reports 5:7717 (Year: 2015).*

(Continued)

*Primary Examiner* — Brian R Gordon
*Assistant Examiner* — Dwan A Gerido
(74) *Attorney, Agent, or Firm* — Wilson Sonsini Goodrich & Rosati

(57) ABSTRACT

A device for the capture and adsorption of blood-borne materials of interest comprising a fluidic cartridge with at least one inlet and at least one outlet; a multidirectional fluidic channel between the at least one inlet and the at least one outlet; said multidirectional fluidic channel comprising at least one inner wall; and a substance coating at least a portion of the at least one inner wall of the multidirectional fluidic channel.

25 Claims, 17 Drawing Sheets

(56) References Cited

U.S. PATENT DOCUMENTS 6,699,987 B2 3/2004 Hillebrand et al.
6,719,907 B2 4/2004 Collins et al.
RE38,869 E 11/2005 Polaschegg et al.
7,122,640 B2 10/2006 Gjerde et al.
7,151,167 B2 12/2006 Gierde et al.
7,569,025 B2 8/2009 Cantor
7,674,377 B2 3/2010 Carew
7,713,412 B2 5/2010 Heilmann et al.
7,723,123 B1 5/2010 Murphy et al.
7,789,245 B2 9/2010 Westberg et al.
7,993,821 B2 8/2011 Chiu et al.
8,007,738 B2 8/2011 Murphy et al.
8,173,413 B2 5/2012 Chiu et al.
8,206,330 B2 6/2012 Hyde et al.
8,288,172 B2 10/2012 Ichim et al.
8,308,672 B2 11/2012 Hyde et al.
8,425,446 B2 4/2013 Humes et al.
8,475,432 B2 7/2013 Moberg et al.
8,580,559 B2 11/2013 Petersen et al.
8,584,869 B2 11/2013 Shimagaki et al.
8,647,289 B2 2/2014 Pages et al.
8,758,286 B2 6/2014 Ward et al.
8,765,393 B2 7/2014 Burton et al.
8,784,012 B2 7/2014 Toner et al.
8,807,879 B2 8/2014 Toner et al.
8,915,875 B2 12/2014 Passlick-Deetjen et al.
9,033,908 B2 5/2015 Schilthuizen et al.
9,061,108 B2 6/2015 Kitaguchi et al.
9,072,831 B2 7/2015 Kelly et al.
9,095,666 B2 8/2015 Kizhakkedathu et al.
9,128,101 B2 9/2015 Halbert et al.
9,140,252 B2 9/2015 Miyazaki et al.
9,157,839 B2 10/2015 Chiu et al.
9,314,719 B2 4/2016 McAlister
9,322,047 B2 4/2016 Park et al.
9,364,601 B2 6/2016 Ichim et al.
9,408,962 B2 8/2016 Ward et al.
9,409,146 B2 8/2016 Frangione et al.
9,433,880 B2 9/2016 Lean et al.
9,458,489 B2 10/2016 Lim et al.
9,464,118 B2 10/2016 Willbold et al.
9,526,735 B2 12/2016 Kusunoki et al.
9,591,845 B2 3/2017 Willbold
9,707,333 B2 7/2017 Ichim et al.
9,782,531 B2 10/2017 Leinenbach et al.
9,789,485 B2 10/2017 Han et al.
9,808,803 B2 11/2017 Toner et al.
9,833,182 B2 12/2017 Marchiarullo et al.
9,867,923 B2 1/2018 Reiser
9,869,671 B2 1/2018 Dryga et al.
9,968,722 B2 5/2018 Tumlin
10,035,104 B2 7/2018 Chiu et al.
10,123,530 B2 11/2018 Willbold
10,894,255 B2 1/2021 Hou et al.
10,940,249 B2 3/2021 Min
11,154,861 B2 10/2021 Miller et al.
11,833,508 B2 * 12/2023 Han .................. B01L 3/502761
11,883,821 B2 1/2024 Miller et al.
2002/0164816 A1 11/2002 Quake
2003/0152491 A1 8/2003 Kellogg et al.
2004/0043479 A1 3/2004 Briscoe et al.
2004/0081563 A1 4/2004 Brach et al.
2004/0126890 A1 7/2004 Gjerde et al.
2004/0140265 A1 7/2004 Lihme
2004/0252584 A1 12/2004 Ji et al.
2005/0009101 A1 1/2005 Blackburn
2005/0103712 A1 5/2005 Voyce
2005/0133370 A1 6/2005 Park et al.
2005/0158306 A1 7/2005 Halikas
2005/0209547 A1 9/2005 Burbank et al.
2005/0238641 A1 10/2005 Burton et al.
2006/0030027 A1 2/2006 Ellson et al.
2007/0017812 A1 1/2007 Bousse
2007/0077555 A1 4/2007 Nowak et al.
2008/0011684 A1 1/2008 Dorian et al.
2008/0081332 A1 * 4/2008 Amano .................. B82Y 30/00
435/7.1
2008/0200342 A1 8/2008 Rao et al.
2009/0004665 A1 1/2009 Brenner
2009/0014360 A1 1/2009 Toner et al.
2009/0136586 A1 5/2009 Larm et al.
2009/0142772 A1 6/2009 Lau et al.
2009/0211976 A1 8/2009 Seidel et al.
2009/0215125 A1 8/2009 Reed et al.
2009/0255601 A1 10/2009 Baeuerle et al.
2009/0259164 A1 10/2009 Pages et al.
2009/0304677 A1 12/2009 Ichim et al.
2010/0075340 A1 3/2010 Javanmard et al.
2010/0130904 A1 5/2010 Kirber
2010/0135976 A1 6/2010 Nilsson et al.
2010/0173392 A1 7/2010 Davis et al.
2010/0217173 A1 8/2010 Hyde et al.
2010/0268147 A1 10/2010 Humes et al.
2010/0268199 A1 10/2010 Hyde et al.
2010/0285044 A1 11/2010 Lentz
2011/0014722 A1 1/2011 Sakowski et al.
2011/0098809 A1 * 4/2011 Wardle ................ A61F 9/00781
623/6.12
2011/0295175 A1 12/2011 Felder et al.
2012/0022441 A1 1/2012 Kelly et al.
2012/0109171 A1 5/2012 Zeroni et al.
2012/0115167 A1 5/2012 Chandler et al.
2012/0122831 A1 5/2012 Sauer-Budge et al.
2012/0149872 A1 6/2012 Belgrader
2012/0152847 A1 6/2012 Falkenhagen et al.
2012/0160771 A1 6/2012 Storr et al.
2012/0289429 A1 11/2012 Chen et al.
2012/0305482 A1 12/2012 McCrea et al.
2012/0328488 A1 12/2012 Puntambekar et al.
2013/0015118 A1 1/2013 Ichim et al.
2013/0045216 A1 2/2013 Frangione et al.
2013/0045496 A1 2/2013 Jansen
2013/0071350 A1 3/2013 Lentz
2013/0123308 A1 5/2013 Ghannoum et al.
2013/0131423 A1 5/2013 Wang et al.
2013/0209988 A1 8/2013 Barber et al.
2013/0251672 A1 9/2013 Lentz
2013/0270198 A1 10/2013 Leinenbach et al.
2013/0287772 A1 10/2013 Halbert et al.
2013/0302814 A1 11/2013 Haydock
2014/0012097 A1 1/2014 McCrea et al.
2014/0014570 A1 1/2014 Okuda
2014/0039172 A1 2/2014 Nelson et al.
2014/0042098 A1 2/2014 Kitaguchi et al.
2014/0083945 A1 3/2014 Reiser
2014/0127312 A1 5/2014 Kizhakkedathu et al.
2014/0134646 A1 5/2014 Martin et al.
2014/0148350 A1 5/2014 Spetzler et al.
2014/0148750 A1 5/2014 Pages et al.
2014/0154703 A1 6/2014 Skelley et al.
2014/0166578 A1 6/2014 Ichim et al.
2014/0179659 A1 6/2014 Kusunoki et al.
2014/0255409 A1 9/2014 Nilsson
2014/0291248 A1 10/2014 Foley et al.
2014/0326339 A1 11/2014 Toner et al.
2015/0038364 A1 2/2015 Zheng et al.
2015/0110763 A1 4/2015 Leach
2015/0111195 A1 4/2015 Hamman et al.
2015/0111277 A1 4/2015 Hamman et al.
2015/0111849 A1 4/2015 McCrea et al.
2015/0119336 A1 4/2015 Willbold et al.
2015/0121808 A1 5/2015 Gaitas et al.
2015/0122737 A1 5/2015 Gaitas
2015/0132312 A1 5/2015 McAlvin et al.
2015/0231233 A1 8/2015 Lentz
2015/0273129 A1 10/2015 Freeman et al.
2015/0282477 A1 10/2015 Willbold
2015/0285808 A1 10/2015 Nagrath et al.
2015/0290381 A1 10/2015 Tumlin
2015/0290386 A1 10/2015 Zhao et al.
2015/0306238 A1 10/2015 Baker et al.
2015/0368635 A1 12/2015 Lo et al.
2016/0022898 A1 1/2016 Larm et al.
2016/0032350 A1 2/2016 Hou et al.

(56) References Cited

U.S. PATENT DOCUMENTS

| | | | |
|---|---|---|---|
| 2016/0058937 A1 | 3/2016 | Gaitas et al. | |
| 2016/0303565 A1* | 10/2016 | Bhagat | G01N 15/0255 |
| 2016/0317949 A1 | 11/2016 | Fabis et al. | |
| 2016/0331886 A1 | 11/2016 | Ward et al. | |
| 2016/0334312 A1 | 11/2016 | Gaitas et al. | |
| 2017/0035956 A1 | 2/2017 | McCrea et al. | |
| 2017/0172139 A1 | 6/2017 | Willbold | |
| 2017/0227535 A1 | 8/2017 | Dryga et al. | |
| 2017/0296732 A1 | 10/2017 | Ebrahimi Warkiani et al. | |
| 2017/0340803 A1 | 11/2017 | Larm et al. | |
| 2018/0038859 A1 | 2/2018 | Winqvist et al. | |
| 2018/0104685 A1 | 4/2018 | Ryans et al. | |
| 2018/0128723 A1 | 5/2018 | Ryu et al. | |
| 2018/0136210 A1 | 5/2018 | Khoo et al. | |
| 2018/0161410 A1 | 6/2018 | Wang | |
| 2018/0161775 A1 | 6/2018 | Kapur et al. | |
| 2018/0345250 A1 | 12/2018 | Bastide et al. | |
| 2018/0361050 A1 | 12/2018 | Ward et al. | |
| 2018/0369783 A1 | 12/2018 | Baier-Goschutz et al. | |
| 2019/0086404 A1 | 3/2019 | Boulet et al. | |
| 2019/0091264 A1 | 3/2019 | Perlstein et al. | |
| 2019/0143027 A1 | 5/2019 | Larm et al. | |
| 2019/0144919 A1 | 5/2019 | Jackson et al. | |
| 2019/0160465 A1 | 5/2019 | Toner et al. | |
| 2019/0176150 A1 | 6/2019 | Kapur et al. | |
| 2019/0300928 A1 | 10/2019 | Krishnamurthy | |
| 2019/0351126 A1 | 11/2019 | Foley et al. | |
| 2020/0056221 A1 | 2/2020 | Ward et al. | |
| 2020/0139372 A1 | 5/2020 | Toner et al. | |
| 2020/0171233 A1 | 6/2020 | McCrea et al. | |
| 2020/0276381 A1 | 9/2020 | Gutzler et al. | |
| 2020/0297913 A1 | 9/2020 | Larm et al. | |
| 2020/0338256 A1 | 10/2020 | Ward et al. | |
| 2021/0190809 A1 | 6/2021 | Vlassov et al. | |
| 2021/0220818 A1 | 7/2021 | Miller | |

FOREIGN PATENT DOCUMENTS

| | | | |
|---|---|---|---|
| CN | 103889556 | A | 6/2014 |
| EP | 1779926 | A2 | 5/2007 |
| EP | 1884274 | A1 | 2/2008 |
| EP | 1942329 | A2 | 7/2008 |
| EP | 1960016 | A1 | 8/2008 |
| EP | 2378267 | A1 | 10/2011 |
| EP | 2378269 | A1 | 10/2011 |
| EP | 2381238 | A1 | 10/2011 |
| EP | 2533828 | A1 | 12/2012 |
| EP | 2562531 | A2 | 2/2013 |
| EP | 2578230 | A1 | 4/2013 |
| EP | 2718312 | A2 | 4/2014 |
| EP | 2378269 | B1 | 10/2014 |
| EP | 2903640 | A1 | 8/2015 |
| EP | 2913671 | A1 | 9/2015 |
| EP | 1886704 | B1 | 9/2016 |
| EP | 3173145 | A1 | 5/2017 |
| EP | 3415214 | A2 | 12/2018 |
| EP | 3417937 | A1 | 12/2018 |
| EP | 2696961 | B1 | 2/2019 |
| EP | 3533860 | A1 | 9/2019 |
| EP | 3197342 | B1 | 8/2020 |
| GB | 2472927 | A | 2/2011 |
| JP | 2003265606 | A | 9/2003 |
| JP | 2007268490 | A | 10/2007 |
| WO | WO-0126673 | A1 | 4/2001 |
| WO | WO-2006021410 | A1 | 3/2006 |
| WO | WO-2009012343 | A2 | 1/2009 |
| WO | WO-2010092333 | A1 | 8/2010 |
| WO | WO-2011039430 | A2 | 4/2011 |
| WO | WO-2011109762 | A1 | 9/2011 |
| WO | WO-2013049636 | A1 | 4/2013 |
| WO | WO-2013126774 | A2 | 8/2013 |
| WO | WO-2014046621 | A1 | 3/2014 |
| WO | WO-2016019142 | A1 | 2/2016 |
| WO | WO 2016040850 | * | 3/2016 |
| WO | WO-2016040850 | A1 | 3/2016 |
| WO | WO-2016077055 | A1 | 5/2016 |
| WO | WO-2017044723 | A1 | 3/2017 |
| WO | WO-2017194609 | A1 | 11/2017 |
| WO | WO 2018009756 | * | 1/2018 |
| WO | WO-2018009756 | A1 | 1/2018 |
| WO | WO-2019136289 | A1 | 7/2019 |
| WO | WO-2019241794 | A1 | 12/2019 |
| WO | WO-2020086761 | A1 | 4/2020 |
| WO | WO-2021097183 | A1 | 5/2021 |

OTHER PUBLICATIONS

Isolation of viable cancer cells in antibody-functionalized microfluidic devices Xiangjun Zheng, Linan Jiang, Joyce Schroeder, Alison Stopeck, Yitshak Zohar Biomicrofluidics 8, 024119, 2014 (Year: 2014).*

PCT/US2019/012403 International Search Report and Written Opinion dated Mar. 25, 2019.

Amini, H. et al., Inertial microfluidic physics, Lab on a Chip 14:2739-2761 (2014).

Bhagat, et al. Continuous particle separation in spiral microchannels using Dean flows and differential migration. Lab Chip. Nov. 2008;8(11): 1906-14. doi: 10.1039/b807107a. Epub Sep. 24, 2008.

Boucher, H.W. et al., Bad Bugs, No. Drugs: No. ESKAPE! An Update from the Infectious Diseases of Society of America, Clinical Infectious Diseases 48:1-12 (2009).

EP19875133.1 Extended European Search Report dated Jun. 28, 2022.

Extended European Search Report for EP Patent Application No. 19735789.0 dated Jan. 28, 2022.

Hongliang, Wang, et al., Application Of Blood Purification Therapy In Sepsis. Chinese Journal of Blood Purification 13(4):329-332 (2014).

Hur, S.C. et al., Inertial focusing of non-spherical microparticles, Applied Physics Letters 99:044101-1-044101-3 (2011).

Kang, J.H. et al., An extracorporeal blood-cleansing device for sepsis therapy, Nature Medicine Technical Reports 20(10):1211-1216, Online Methods 5 pages (Oct. 2014).

Katsaragakis, S. et al., Acinetobacter baumannii Infections in a Surgical Intensive Care Unit: Predictors of Multi-drug Resistance, World Journal of Surgery 32:1194-1202 (2008).

Maragakis, L.L. et al., Acinetobacter baumannii: Epidemiology, Antimicrobial Resistance, and Treatment Options, Antimicrobial Resistance 46:1254-1263 2008.

Masaeli, M. et al., Continuous Inertial Focusing and Separation of Particles by Shape, Physical Review X 2:031017-1-031017-13(2012).

Mayr, F.B. et al., Epidemiology of severe sepsis, Virulence 5(1):4-11 (Jan. 1, 2014).

PCT/US19/57724 International Search Report and Written Opinion dated Feb. 18, 2020.

Raub, C.B. et al., Sequestration of bacteria from whole blood by optimized microfluidic cross-flow filtration for Rapid Antimicrobial Susceptibility Testing, Sensors and Actuators B: Chemical 210:120-123 (2015).

Sun, J. et al., Double spiral microchannel for label-free tumor cell separation and enrichment, Lab on a Chip 12:3952-3960 (2012).

Blais, B.W, et al., Comparison of Fluorogenic and Chromogenic Assay Systems in the Detection of *Escherichia Coli* O157 by a Novel Polymyxin-based ELISA. Letters in Applied Microbiology 39(6):516-522 (2004).

Green, James V, et al., Microfluidic Enrichment of a Target Cell Type From a Heterogenous Suspension by Adhesion-based Negative Selection. Lab on a Chip 9:2245-2248 (2009). With 6 pages of Supplementary Information.

Han, Kyungsup, et al., Self-powered Switch-controlled Nucleic Acid Extraction System. Lab on a Chip 16(1):132-141 (2016).

Kai, Junhai, et al., The Next Generation Microplate Using Power of Microfluidics for Femtogram/ML Level Sensitivity. 15th International Conference on Miniaturized Systems for Chemistry and Life Sciences, 1370-1372 (2011).

Kell, Arnold J, et al., Vancomycin-Modified Nanoparticles for Efficient Targeting and Preconcentration of Gram-Positive and

(56) References Cited

OTHER PUBLICATIONS

Gram-Negative Bacteria. ACS Nano 2(9): 1777-1788 (2008). With 16 pages of supporting information.
Kotz, K.T, et al., Clinical Microfluidics for Neutrophil Genomics and Proteomics. Nature Medicine 16(9):1042-1048 (2010). With 37 pages of Supplementary Information.
Kwak, Bongseop, et al., Spiral Shape Microfluidic Channel for Selective Isolating of Heterogenic Circulating Tumor Cells. Biosensors and Bioelectronics 101:311-316 (2018). Available online Oct. 17, 2017.
Lehmann, Lutz Eric, et al., A Multiplex Real-time PCR Assay for Rapid Detection and Differentiation of 25 Bacterial and Fungal Pathogens From Whole Blood Samples. Medical Microbiology and Immunology 197:313-324 (2008). Published online Nov. 16, 2007.
Li, Peng, et al., Negative Enrichment of Target Cells by Microfluidic Affinity Chromatography. Analytical Chemistry 83:7863-7869 (2011). With 10 pages of Supporting Information.
Plouffe, Brian D, et al., Microfluidic Depletion of Endothelial Cells, Smooth Muscle Cells, and Fibroblasts from Heterogeneous Suspensions. Lab on a Chip 8(3):462-472 (2008).
Shin, Yong, et al., Solid Phase Nucleic Acid Extraction Technique in a Microfluidic Chip Using a Novel Non-chaotropic Agent: Dimethyl Adipimidate. Lab on a Chip 14(2):359-368 (2014).
U.S. Appl. No. 17/224,811 Office Action dated Apr. 26, 2024.
Vickers, Dwayne, A.L, et al., Separation of Two Phenotypically Similar Cell Types via a Single Common Marker in Microfluidic Channels. Lab on a Chip 12:3399-3407 (2012). With 2 pages of Supplementary Information.
Warner, Elizabeth A, et al., Microfluidics-based Capture of Human Neutrophils for Expression Analysis in Blood and Bronchoalveolar Lavage. Laboratory Investigation 91(12): 1787-1795 (2011).
Zhang, Li, et al., A Self-contained Disposable Cartridge Microsystem for Dengue Viral Ribonucleic Acid Extraction. Sensors and Actuators B 160:1557-1564 (2011).
Zhang, Ye, et al., Microfluidic Cell Surface Antigen Expression Analysis Using a Single Antibody Type. The Analyst 141(4): 1440-1447 (2016). With 2 pages of Supporting Information.
Zhu, Minjun, et al., Construction of Fe3O4/Vancomycin/PEG Magnetic Nanocarrier for Highly Efficient Pathogens Enrichment and Gene-Sensing. ACS Applied Materials & Interfaces 7(23):12873-12881 (2015).

* cited by examiner

Colistin

Vancomycin

| Sample | Polymyxin functionalized device - flow rate | Starting Concentration (CFU/mL) (Time Zero) | Percent Reduction at 1 min Compared to Time Zero | Total Captured Bacteria (i.e. saturation point) (CFUs) |
|---|---|---|---|---|
| *A. baumannii* ATCC 17978 | 80 mL/min | 1.02E+05 | 89.46% | 2.39E+07 |
| *A. baumannii* Colistin Resistant | 80 mL/min | 3.87E+04 | 96.34% | 7.89E+06 |
| *K. pneumoniae* ATCC 700603 | 80 mL/min | 1.45E+05 | 99.08% | 1.98E+07 |
| *K. pneumoniae* ATCC 700603 Colistin Resistant | 80 mL/min | 8.67E+04 | 79.62% | 7.31E+06 |

| Sample | Vancomycin functionalized device - flow rate | Starting Concentration (CFU/mL) (Time Zero) | Percent Reduction at 1 min Compared to Time Zero | Total Captured Bacteria (i.e. saturation point) (CFUs) |
|---|---|---|---|---|
| *S. aureus* ATCC 29213 | 80 mL/min | 3.77E+04 | 80.53% | 5.24E+06 |

| Sample | Polyethylene glycol (PEG) functionalized device - flow rate | Starting Concentration (CFU/mL) (Time Zero) | Percent Reduction at 1 min Compared to Time Zero | Total Captured Bacteria (i.e. saturation point) (CFUs) |
|---|---|---|---|---|
| *S. aureus* ATCC 29213 | 80 mL/min | 6.30E+04 | 0.00% | 0.00E+00 |
| *A. baumannii* ATCC 17978 | 80 mL/min | 9.43E+05 | 0.00% | 0.00E+00 |

FIG. 15

DEVICE FOR THE CAPTURE AND REMOVAL OF DISEASE MATERIAL FROM FLUIDS

CROSS-REFERENCE

This application is a continuation of International Patent Application No. PCT/US2019/012403, filed Jan. 4, 2019, which claims the benefit of U.S. Provisional Application No. 62/614,250, filed Jan. 5, 2018, each of which is incorporated herein by reference in its entirety for all purposes.

STATEMENT REGARDING FEDERALLY SPONSORED RESEARCH

This invention was made with Government Support under Small Business Innovation Research Grant No. 1721476 (Phase I) and Grant No. 1831150 (Phase II) awarded by the National Science Foundation. The Government has certain rights to the invention.

SUMMARY

Methods and devices and systems described herein are used to capture and remove bacterial pathogens or associated toxins from fluids for the treatment of sepsis, endotoxemia, bacteremia infection, and other blood-borne diseases. Provided herein are methods, devices, and systems for removing pathogens and/or toxins from fluids by flowing fluids through a multidirectional channel that is coated with a polypeptide antibiotic and/or other materials.

Provided herein are devices, methods, and systems for the capture and adsorption of blood-borne materials of interest comprising a fluidic cartridge with at least one inlet and at least one outlet; a multidirectional fluidic channel between the at least one inlet and the at least one outlet; said multidirectional fluidic channel comprising at least one inner wall; and a substance coating at least a portion of the at least one inner wall of the multidirectional fluidic channel In some embodiments, the substance is selected from the group consisting of: antibodies, crosslinking agents, peptides, proteins, antibiotics, polymers, amines, polyethers, amino acids, aptamers, tumor necrosis factors, adhesion receptors, E-selectin, cytokines, chemotherapy agents, quorum sensing proteins, quorum sensing receptors, and biological agents. In some embodiments, the substance coating the channel wall comprises a fixed, covalently-bonded polypeptide antibiotic. In some embodiments, the covalently-bonded polypeptide antibiotic is a polymyxin-polymyxin B and/or polymyxin E. In some embodiments, the amount of polymyxin fixed is about 0.5 mM (milliMolar) to about 50 mM. In some embodiments, the amount of polymyxin fixed is at least about 0.5 mM. In some embodiments, the amount of polymyxin fixed is at most about 50 mM. In some embodiments, the amount of polymyxin fixed is about 0.5 mM to about 1 mM, about 0.5 mM to about 5 mM, about 0.5 mM to about 10 mM, about 0.5 mM to about 20 mM, about 0.5 mM to about 30 mM, about 0.5 mM to about 40 mM, about 0.5 mM to about 50 mM, about 1 mM to about 5 mM, about 1 mM to about 10 mM, about 1 mM to about 20 mM, about 1 mM to about 30 mM, about 1 mM to about 40 mM, about 1 mM to about 50 mM, about 5 mM to about 10 mM, about 5 mM to about 20 mM, about 5 mM to about 30 mM, about 5 mM to about 40 mM, about 5 mM to about 50 mM, about 10 mM to about 20 mM, about 10 mM to about 30 mM, about 10 mM to about 40 mM, about 10 mM to about 50 mM, about 20 mM to about 30 mM, about 20 mM to about 40 mM, about 20 mM to about 50 mM, about 30 mM to about 40 mM, about 30 mM to about 50 mM, or about 40 mM to about 50 mM. The term about, when used in reference to the amount of polymyxin, means 0.5 mM, 1 mM, 5 mM, 10 mM, 20 mM, 30 mM, 40 mM, or 50 mM. In some embodiments, the covalently-bonded polypeptide antibiotic is vancomycin. In some embodiments, the amount of vancomycin fixed is about 0.5 mM to about 50 mM. In some embodiments, the amount of vancomycin fixed is at least about 0.5 mM. In some embodiments, the amount of vancomycin fixed is at most about 50 mM. In some embodiments, the amount of vancomycin fixed is about 0.5 mM to about 1 mM, about 0.5 mM to about 5 mM, about 0.5 mM to about 10 mM, about 0.5 mM to about 20 mM, about 0.5 mM to about 30 mM, about 0.5 mM to about 40 mM, about 0.5 mM to about 50 mM, about 1 mM to about 5 mM, about 1 mM to about 10 mM, about 1 mM to about 20 mM, about 1 mM to about 30 mM, about 1 mM to about 40 mM, about 1 mM to about 50 mM, about 5 mM to about 10 mM, about 5 mM to about 20 mM, about 5 mM to about 30 mM, about 5 mM to about 40 mM, about 5 mM to about 50 mM, about 10 mM to about 20 mM, about 10 mM to about 30 mM, about 10 mM to about 40 mM, about 10 mM to about 50 mM, about 20 mM to about 30 mM, about 20 mM to about 40 mM, about 20 mM to about 50 mM, about 30 mM to about 40 mM, about 30 mM to about 50 mM, or about 40 mM to about 50 mM. The term about, when used in reference to the amount of vancomycin, means 0.5 mM, 1 mM, 5 mM, 10 mM, 20 mM, 30 mM, 40 mM, or 50 mM. In some embodiments, the substance coating the channel wall comprises a fixed crosslinking agent selected from the group consisting of: hexamethylene diamine, polyethylene glycol, polyethylene glycol derivatives, N-hydroxysuccinimide esters, and glycine. In some embodiments, the hexamethylene diamine crosslinking agent to be fixed to the base material is about 1% volume/volume (v/v) aqueous solution to about 20% (v/v) aqueous solution. In some embodiments, the hexamethylene diamine crosslinking agent to be fixed to the base material is at least about 1% (v/v) aqueous solution. In some embodiments, the hexamethylene diamine crosslinking agent to be fixed to the base material is at most about 20% (v/v) aqueous solution. In some embodiments, the hexamethylene diamine crosslinking agent to be fixed to the base material is about 1% (v/v) aqueous solution to about 2% (v/v) aqueous solution, about 1% (v/v) aqueous solution to about 3% (v/v) aqueous solution, about 1% (v/v) aqueous solution to about 4% (v/v) aqueous solution, about 1% (v/v) aqueous solution to about 5% (v/v) aqueous solution, about 1% (v/v) aqueous solution to about 10% (v/v) aqueous solution, about 1% (v/v) aqueous solution to about 15% (v/v) aqueous solution, about 1% (v/v) aqueous solution to about 20% (v/v) aqueous solution, about 2% (v/v) aqueous solution to about 3% (v/v) aqueous solution, about 2% (v/v) aqueous solution to about 4% (v/v) aqueous solution, about 2% (v/v) aqueous solution to about 5% (v/v) aqueous solution, about 2% (v/v) aqueous solution to about 10% (v/v) aqueous solution, about 2% (v/v) aqueous solution to about 15% (v/v) aqueous solution, about 2% (v/v) aqueous solution to about 20% (v/v) aqueous solution, about 3% (v/v) aqueous solution to about 4% (v/v) aqueous solution, about 3% (v/v) aqueous solution to about 5% (v/v) aqueous solution, about 3% (v/v) aqueous solution to about 10% (v/v) aqueous solution, about 3% (v/v) aqueous solution to about 15% (v/v) aqueous solution, about 3% (v/v) aqueous solution to about 20% (v/v) aqueous solution, about 4% (v/v) aqueous solution to about 5% (v/v) aqueous solution, about 4% (v/v) aqueous solution to about 10% (v/v) aqueous solution, about 4% (v/v) aqueous solution to about 15% (v/v) aqueous solution, about 4% (v/v) aqueous solution to about 20% (v/v) aqueous solution, about 5% (v/v) aqueous solution to about 10% (v/v) aqueous solution, about 5% (v/v) aqueous solution to about 15% (v/v) aqueous solution, about 5% (v/v) aqueous solution to about 20% (v/v) aqueous solution, about 10% (v/v) aqueous solution to about 15% (v/v) aqueous solution, about 10% (v/v) aqueous solution to about 20% (v/v) aqueous solution, or about 15% (v/v) aqueous solution to about 20% (v/v) aqueous solution. The term about, when used in reference to the amount of the hexamethylene diamine crosslinking agent aqueous solution, means 1% (v/v) aqueous solution, 2% (v/v) aqueous solution, 3% (v/v) aqueous solution, 4% (v/v) aqueous solution, 5% (v/v) aqueous solution, 10% (v/v) aqueous solution, 15% (v/v) aqueous solution, or 20% (v/v) aqueous solution. In some embodiments, the crosslinking agent to be fixed to the base material is polyethylene glycol or a derivative substance in which the amount fixed is about 1 mM to about 50 mM. In some embodiments, the crosslinking agent to be fixed to the base material is polyethylene glycol or a derivative substance in which the amount fixed is at least about 1 mM. In some embodiments, the crosslinking agent to be fixed to the base material is polyethylene glycol or a derivative substance in which the amount fixed is at most about 50 mM. In some embodiments, the crosslinking agent to be fixed to the base material is polyethylene glycol or a derivative substance in which the amount fixed is about 1 mM to about 5 mM, about 1 mM to about 10 mM, about 1 mM to about 20 mM, about 1 mM to about 30 mM, about 1 mM to about 40 mM, about 1 mM to about 50 mM, about 5 mM to about 10 mM, about 5 mM to about 20 mM, about 5 mM to about 30 mM, about 5 mM to about 40 mM, about 5 mM to about 50 mM, about 10 mM to about 20 mM, about 10 mM to about 30 mM, about 10 mM to about 40 mM, about 10 mM to about 50 mM, about 20 mM to about 30 mM, about 20 mM to about 40 mM, about 20 mM to about 50 mM, about 30 mM to about 40 mM, about 30 mM to about 50 mM, or about 40 mM to about 50 mM. The term about, when used in reference to the amount of crosslinking agent, means 1 mM, 5 mM, 10 mM, 20 mM, 30 mM, 40 mM, or 50 mM. In some embodiments of the devices or systems herein, the multidirectional channel is composed of at least one thermoplastic polymer base material that has at least one surface exposed functional group. In some embodiments, the thermoplastic polymer base material has at least one surface exposed functional group selected from the groups consisting of: carbonyl groups, carboxyl groups, alcohol groups, amino groups, chloride groups, styrene groups, alpha-halogenated acyl group, benzyl groups, isocyanic acid groups, and other polymers or copolymers such as vinylchloride, vinylacetate, acrylamide, polyethylene, polyethylene terephthalate acrylic acid, acrylonitrile, maleic anhydride and methylmethacrylate. In some embodiments, the base material is polycarbonate.

In some embodiments of the device, the fluidic device is disposable. In some embodiments of the device, the multidirectional channel has a width of about 0.01 mm (millimeter) to about 1,000 mm. In some embodiments of the device, the multidirectional channel has a width of at least about 0.01 mm. In some embodiments of the device, the multidirectional channel has a width of at most about 1,000 mm. In some embodiments of the device, the multidirectional channel has a width of about 0.01 mm to about 0.05 mm, about 0.01 mm to about 0.1 mm, about 0.01 mm to about 0.5 mm, about 0.01 mm to about 1 mm, about 0.01 mm to about 10 mm, about 0.01 mm to about 50 mm, about 0.01 mm to about 100 mm, about 0.01 mm to about 500 mm, about 0.01 mm to about 1,000 mm, about 0.05 mm to about 0.1 mm, about 0.05 mm to about 0.5 mm, about 0.05 mm to about 1 mm, about 0.05 mm to about 10 mm, about 0.05 mm to about 50 mm, about 0.05 mm to about 100 mm, about 0.05 mm to about 500 mm, about 0.05 mm to about 1,000 mm, about 0.1 mm to about 0.5 mm, about 0.1 mm to about 1 mm, about 0.1 mm to about 10 mm, about 0.1 mm to about 50 mm, about 0.1 mm to about 100 mm, about 0.1 mm to about 500 mm, about 0.1 mm to about 1,000 mm, about 0.5 mm to about 1 mm, about 0.5 mm to about 10 mm, about 0.5 mm to about 50 mm, about 0.5 mm to about 100 mm, about 0.5 mm to about 500 mm, about 0.5 mm to about 1,000 mm, about 1 mm to about 10 mm, about 1 mm to about 50 mm, about 1 mm to about 100 mm, about 1 mm to about 500 mm, about 1 mm to about 1,000 mm, about 10 mm to about 50 mm, about 10 mm to about 100 mm, about 10 mm to about 500 mm, about 10 mm to about 1,000 mm, about 50 mm to about 100 mm, about 50 mm to about 500 mm, about 50 mm to about 1,000 mm, about 100 mm to about 500 mm, about 100 mm to about 1,000 mm, or about 500 mm to about 1,000 mm. The term about, when used in reference to the width of the multidirectional channel, means 0.01 mm, 0.05 mm, 0.1 mm, 0.5 mm, 1 mm, 10 mm, 50 mm, 100 mm, or 500 mm. In some embodiments of the device, the multidirectional channel has a height of about 0.001 mm to about 100 mm. In some embodiments of the device, the multidirectional channel has a height of at least about 0.001 mm. In some embodiments of the device, the multidirectional channel has a height of at most about 100 mm. In some embodiments of the device, the multidirectional channel has a height of about 0.001 mm to about 0.005 mm, about 0.001 mm to about 0.01 mm, about 0.001 mm to about 0.05 mm, about 0.001 mm to about 0.1 mm, about 0.001 mm to about 0.5 mm, about 0.001 mm to about 1 mm, about 0.001 mm to about 10 mm, about 0.001 mm to about 50 mm, about 0.001 mm to about 100 mm, about 0.005 mm to about 0.01 mm, about 0.005 mm to about 0.05 mm, about 0.005 mm to about 0.1 mm, about 0.005 mm to about 0.5 mm, about 0.005 mm to about 1 mm, about 0.005 mm to about 10 mm, about 0.005 mm to about 50 mm, about 0.005 mm to about 100 mm, about 0.01 mm to about 0.05 mm, about 0.01 mm to about 0.1 mm, about 0.01 mm to about 0.5 mm, about 0.01 mm to about 1 mm, about 0.01 mm to about 10 mm, about 0.01 mm to about 50 mm, about 0.01 mm to about 100 mm, about 0.05 mm to about 0.1 mm, about 0.05 mm to about 0.5 mm, about 0.05 mm to about 1 mm, about 0.05 mm to about 10 mm, about 0.05 mm to about 50 mm, about 0.05 mm to about 100 mm, about 0.1 mm to about 0.5 mm, about 0.1 mm to about 1 mm, about 0.1 mm to about 10 mm, about 0.1 mm to about 50 mm, about 0.1 mm to about 100 mm, about 0.5 mm to about 1 mm, about 0.5 mm to about 10 mm, about 0.5 mm to about 50 mm, about 0.5 mm to about 100 mm, about 1 mm to about 10 mm, about 1 mm to about 50 mm, about 1 mm to about 100 mm, about 10 mm to about 50 mm, about 10 mm to about 100 mm, or about 50 mm to about 100 mm. The term about, when used in reference to the height of the multidirectional channel, means 0.001 mm, 0.005 mm, 0.01 mm, 0.05 mm, 0.1 mm, 0.5 mm, 1 mm, 10 mm, or 50 mm. In some embodiments of the device, the multidirectional channel has a length of about 0.1 mm to about 10,000 mm. In some embodiments of the device, the multidirectional channel has a length of at least about 0.1 mm. In some embodiments of the device, the multidirectional channel has a length of at most about 10,000 mm. In some embodiments of the device, the multidirectional channel has a length of about 0.1 mm to about 0.5 mm, about 0.1 mm to about 1 mm, about 0.1 mm to about 10 mm, about 0.1 mm to about 50 mm, about 0.1 mm to about 100 mm, about 0.1 mm to about 500 mm, about 0.1 mm to about 1,000 mm, about 0.1 mm to about 5,000 mm, about 0.1 mm to about 10,000 mm, about 0.5 mm to about 1 mm, about 0.5 mm to about 10 mm, about 0.5 mm to about 50 mm, about 0.5 mm to about 100 mm, about 0.5 mm to about 500 mm, about 0.5 mm to about 1,000 mm, about 0.5 mm to about 5,000 mm, about 0.5 mm to about 10,000 mm, about 1 mm to about 10 mm, about 1 mm to about 50 mm, about 1 mm to about 100 mm, about 1 mm to about 500 mm, about 1 mm to about 1,000 mm, about 1 mm to about 5,000 mm, about 1 mm to about 10,000 mm, about 10 mm to about 50 mm, about 10 mm to about 100 mm, about 10 mm to about 500 mm, about 10 mm to about 1,000 mm, about 10 mm to about 5,000 mm, about 10 mm to about 10,000 mm, about 50 mm to about 100 mm, about 50 mm to about 500 mm, about 50 mm to about 1,000 mm, about 50 mm to about 5,000 mm, about 50 mm to about 10,000 mm, about 100 mm to about 500 mm, about 100 mm to about 1,000 mm, about 100 mm to about 5,000 mm, about 100 mm to about 10,000 mm, about 500 mm to about 1,000 mm, about 500 mm to about 5,000 mm, about 500 mm to about 10,000 mm, about 1,000 mm to about 5,000 mm, about 1,000 mm to about 10,000 mm, or about 5,000 mm to about 10,000 mm. The term about, when used in reference to length of the multidirectional channel, means 0.1 mm, 0.5 mm, 1 mm, 10 mm, 50 mm, 100 mm, 500 mm, 1,000 mm, or 5,000 mm. In some embodiments of the device, the multidirectional channel has a length of about 1.0 to about 3,000.0 mm. In some embodiments of the device, the spiral shaped channel has an outer-most radius of curvature of about 0.1 mm to about 1,000 mm. In some embodiments of the device, the spiral shaped channel has an outer-most radius of curvature of at least about 0.1 mm. In some embodiments of the device, the spiral shaped channel has an outer-most radius of curvature of at most about 1,000 mm. In some embodiments of the device, the spiral shaped channel has an outer-most radius of curvature of about 0.1 mm to about 10 mm, about 0.1 mm to about 50 mm, about 0.1 mm to about 100 mm, about 0.1 mm to about 500 mm, about 0.1 mm to about 1,000 mm, 1 mm to about 10 mm, about 1 mm to about 50 mm, about 1 mm to about 100 mm, about 1 mm to about 500 mm, about 1 mm to about 1,000 mm, about 10 mm to about 50 mm, about 10 mm to about 100 mm, about 10 mm to about 500 mm, about 10 mm to about 1,000 mm, about 50 mm to about 100 mm, about 50 mm to about 500 mm, about 50 mm to about 1,000 mm, about 100 mm to about 500 mm, about 100 mm to about 1,000 mm, or about 500 mm to about 1,000 mm. In some embodiments of the device, the spiral shaped channel has an outer-most radius of curvature of about 5 mm to about 100 mm. In some embodiments of the device, the spiral shaped channel has an outer-most radius of curvature of at least about 5 mm. In some embodiments of the device, the spiral shaped channel has an outer-most radius of curvature of at most about 100 mm. In some embodiments of the device, the spiral shaped channel has an outer-most radius of curvature of about 5 mm to about 10 mm, about 5 mm to about 25 mm, about 5 mm to about 50 mm, about 5 mm to about 75 mm, about 5 mm to about 100 mm, about 10 mm to about 25 mm, about 10 mm to about 50 mm, about 10 mm to about 75 mm, about 10 mm to about 100 mm, about 25 mm to about 50 mm, about 25 mm to about 75 mm, about 25 mm to about 100 mm, about 50 mm to about 75 mm, about 50 mm to about 100 mm, or about 75 mm to about 100 mm. In some embodiments of the device, the spiral shaped multidirectional channel has a center-to-center distance between the channels in the spiral about 0.01 mm to about 1,000 mm. In some embodiments of the device, the spiral shaped multidirectional channel has a center-to center distance between the channels in the spiral at least about 0.01 mm. In some embodiments of the device, the spiral shaped multidirectional channel has a center-to center distance between the channels in the spiral at most about 1,000 mm. In some embodiments of the device, the spiral shaped multidirectional channel has a center-to center distance between the channels in the spiral about 0.01 mm to about 0.05 mm, about 0.01 mm to about 0.1 mm, about 0.01 mm to about 0.5 mm, about 0.01 mm to about 1 mm, about 0.01 mm to about 10 mm, about 0.01 mm to about 50 mm, about 0.01 mm to about 100 mm, about 0.01 mm to about 500 mm, about 0.01 mm to about 1,000 mm, about 0.05 mm to about 0.1 mm, about 0.05 mm to about 0.5 mm, about 0.05 mm to about 1 mm, about 0.05 mm to about 10 mm, about 0.05 mm to about 50 mm, about 0.05 mm to about 100 mm, about 0.05 mm to about 500 mm, about 0.05 mm to about 1,000 mm, about 0.1 mm to about 0.5 mm, about 0.1 mm to about 1 mm, about 0.1 mm to about 10 mm, about 0.1 mm to about 50 mm, about 0.1 mm to about 100 mm, about 0.1 mm to about 500 mm, about 0.1 mm to about 1,000 mm, about 0.5 mm to about 1 mm, about 0.5 mm to about 10 mm, about 0.5 mm to about 50 mm, about 0.5 mm to about 100 mm, about 0.5 mm to about 500 mm, about 0.5 mm to about 1,000 mm, about 1 mm to about 10 mm, about 1 mm to about 50 mm, about 1 mm to about 100 mm, about 1 mm to about 500 mm, about 1 mm to about 1,000 mm, about 10 mm to about 50 mm, about 10 mm to about 100 mm, about 10 mm to about 500 mm, about 10 mm to about 1,000 mm, about 50 mm to about 100 mm, about 50 mm to about 500 mm, about 50 mm to about 1,000 mm, about 100 mm to about 500 mm, about 100 mm to about 1,000 mm, or about 500 mm to about 1,000 mm. The term about, when used in reference to the distance between the channel in the spiral, means 0.01 mm, 0.05 mm, 0.1 mm, 0.5 mm, 1 mm, 10 mm, 50 mm, 100 mm, or 500 mm. In some embodiments of the device, the multidirectional channel is helically shaped and fabricated around a cylindrical chamber. In some embodiments of the device, the helical shaped multidirectional channel has a radius of curvature of about 0.1 mm to about 1,000 mm. In some embodiments of the device, the helical shaped multidirectional channel has a radius of curvature of at least about 0.1 mm. In some embodiments of the device, the helical shaped multidirectional channel has a radius of curvature of at most about 1,000 mm. In some embodiments of the device, the helical shaped multidirectional channel has a radius of curvature of about 0.1 mm to about 5 mm, about 0.1 mm to about 10 mm, about 0.1 mm to about 50 mm, about 0.1 mm to about 100 mm, about 0.1 mm to about 500 mm, about 0.1 mm to about 1,000 mm, 1 mm to about 5 mm, about 1 mm to about 10 mm, about 1 mm to about 50 mm, about 1 mm to about 100 mm, about 1 mm to about 500 mm, about 1 mm to about 1,000 mm, about 5 mm to about 10 mm, about 5 mm to about 50 mm, about 5 mm to about 100 mm, about 5 mm to about 500 mm, about 5 mm to about 1,000 mm, about 10 mm to about 50 mm, about 10 mm to about 100 mm, about 10 mm to about 500 mm, about 10 mm to about 1,000 mm, about 50 mm to about 100 mm, about 50 mm to about 500 mm, about 50 mm to about 1,000 mm, about 100 mm to about 500 mm, about 100 mm to about 1,000 mm, or about 500 mm to about 1,000 mm. The term about, when used in reference to the radius of curvature of the helical shaped multidirectional channel, means 0.1 mm, 1 mm, 5 mm, 10 mm, 50 mm, 100 mm, 500 mm, or 1,000 mm. In some embodiments of the device, the helical shaped multidirectional channel has a radius of curvature of 5.0 to 100.0 mm. In some embodiments of the device, the helical shaped multidirectional channel has a radius of curvature of about 5.0 to about 100.0 mm. In some embodiments of the device, the helical shaped multidirectional channel has a pitch of about 1 mm to about 1,000 mm, with the pitch measured as the height of one complete helix turn measured parallel to the axis of the helix. In some embodiments of the device, the helical shaped multidirectional channel has a pitch of at least about 0.1 mm. In some embodiments of the device, the helical shaped multidirectional channel has a pitch of at most about 1,000 mm. In some embodiments of the device, the helical shaped multidirectional channel has a pitch of about 0.1 mm to about 5 mm, about 0.1 mm to about 10 mm, about 0.1 mm to about 50 mm, about 0.1 mm to about 100 mm, about 0.1 mm to about 500 mm, about 0.1 mm to about 1,000 mm, 1 mm to about 5 mm, about 1 mm to about 10 mm, about 1 mm to about 50 mm, about 1 mm to about 100 mm, about 1 mm to about 500 mm, about 1 mm to about 1,000 mm, about 5 mm to about 10 mm, about 5 mm to about 50 mm, about 5 mm to about 100 mm, about 5 mm to about 500 mm, about 5 mm to about 1,000 mm, about 10 mm to about 50 mm, about 10 mm to about 100 mm, about 10 mm to about 500 mm, about 10 mm to about 1,000 mm, about 50 mm to about 100 mm, about 50 mm to about 500 mm, about 50 mm to about 1,000 mm, about 100 mm to about 500 mm, about 100 mm to about 1,000 mm, or about 500 mm to about 1,000 mm. The term about, when used in reference to the pitch, means 0.1 mm, 1 mm, 5 mm, 10 mm, 50 mm, 100 mm, 500 mm, or 1,000 mm. In some embodiments of the device, the helical shaped multidirectional channel has a pitch of about 1.0 to about 100.0 mm. In some embodiments of the device, the helical shaped multidirectional channel operates at a flow rate of about 1 mL/min (milliliters per minute) to about 1,000 mL/min. In some embodiments of the device, the helical shaped multidirectional channel operates at a flow rate of at least about 1 mL/min. In some embodiments of the device, the helical shaped multidirectional channel operates at a flow rate of at most about 1,000 mL/min. In some embodiments of the device, the helical shaped multidirectional channel operates at a flow rate of about 1 mL/min to about 5 mL/min, about 1 mL/min to about 10 mL/min, about 1 mL/min to about 50 mL/min, about 1 mL/min to about 100 mL/min, about 1 mL/min to about 500 mL/min, about 1 mL/min to about 1,000 mL/min, about 5 mL/min to about 10 mL/min, about 5 mL/min to about 50 mL/min, about 5 mL/min to about 100 mL/min, about 5 mL/min to about 500 mL/min, about 5 mL/min to about 1,000 mL/min, about 10 mL/min to about 50 mL/min, about 10 mL/min to about 100 mL/min, about 10 mL/min to about 500 mL/min, about 10 mL/min to about 1,000 mL/min, about 50 mL/min to about 100 mL/min, about 50 mL/min to about 500 mL/min, about 50 mL/min to about 1,000 mL/min, about 100 mL/min to about 500 mL/min, about 100 mL/min to about 1,000 mL/min, or about 500 mL/min to about 1,000 mL/min. The term about, when used in reference to the flow rate, means 1 mL/min, 5 mL/min, 10 mL/min, 50 mL/min, 100 mL/min, 200 mL/min, 500 mL/min, or 1000 mL/min. In some embodiments of the device, the helical shaped multidirectional channel operates with flow rates of about 50 to about 400 mL/min. In some embodiments of the device, the multidirectional channel is enclosed. In some embodiments of the device, the multidirectional channel is enclosed using bolts, adhesive, binding material, thermal expansion, resin, epoxy, an inner and/or outer sleeve, a base plate, a mandrel, cover glass, curing, extrusion welding, contact welding, high frequency welding, friction welding, laser welding, ultrasonic welding, solvent welding, or casting. In some embodiments of the device, the multidirectional channel is fabricated using at least one method selected from the group consisting of: 3-D printing, soft lithography, photolithography, injection molding, blow molding, casting, ultrasonic welding, high frequency welding, heated tool or plate welding, solvent bonding, laser welding, spin welding, infrared welding, vibration welding, adhesive bonding, machining, turning, drilling, boring, reaming, electric discharge machining, or milling In some embodiments of the device, tubing is attached to the multidirectional channel inlet(s) and/or outlet(s) by the use of fittings, caps, or luer lock connectors.

Provided herein is a method for the capture and adsorption of materials of interest comprising bringing a sample of fluid in contact with a multidirectional, polypeptide antibiotic coated channel; adsorbing said material(s) of interest on said multidirectional channel walls; and detecting the presence or amount of said materials of interest captured within the multidirectional, polypeptide antibiotic coated channel In some embodiments of the method, a fluid sample is brought in contact with a multidirectional, polypeptide antibiotic coated channel using a pump. In some embodiments, the pump is a peristaltic pump. In some embodiments, the pump is a syringe pump. In some embodiments of the method, a fluid sample is brought in contact with a multidirectional, polypeptide antibiotic coated channel using a syringe. In some embodiments, the polypeptide antibiotic is polymyxin. In some embodiments, the polypeptide antibiotic is vancomycin. In some embodiments of the method, heparin, sodium citrate, or other anticoagulants, are added to the fluid sample prior to being brought in contact with a multidirectional, polypeptide antibiotic coated channel In some embodiments, detection of the presence or amount of materials of interest captured within the multidirectional, polypeptide antibiotic coated channel is performed using a method selected from the group comprising: cell counting, MALDI-TOF MS (matrix assisted laser desorption ionization-time of flight mass spectrometry), mass spectrometry, PCR (polymerase chain reaction), biosensing, flow cytometry, and fluorescent labeling.

Provided herein is a system for the capture and adsorption of blood-borne materials of interest comprising a fluidic cartridge with at least one inlet and at least one outlet; a multidirectional fluidic channel between the at least one inlet and the at least one outlet; said multidirectional fluidic channel comprising at least one inner wall; and a substance selected from the group consisting of: antibodies, crosslinking agents, peptides, proteins, antibiotics, polymers, amines, polyethers, amino acids, aptamers, tumor necrosis factors, adhesion receptors, E-selectin, cytokines, chemotherapy agents, quorum sensing proteins, quorum sensing receptors, and biological agents, coating, fixed and covalently bonded to at least a portion of the at least one inner wall of the multidirectional fluidic channel In some embodiments of the system, the substance coating the channel wall comprises a fixed, covalently-bonded polypeptide antibiotic. In some embodiments of the system, the covalently-bonded polypeptide antibiotic is polymyxin. In some embodiments, the covalently-bonded polypeptide antibiotic is vancomycin. In some embodiments of the system, the substance coating the channel wall comprises a fixed crosslinking agent selected from the group consisting of: hexamethylene diamine, polyethylene glycol, polyethylene glycol derivatives, N-hydroxysuccinimide esters, and glycine. In some embodiments of the system, the multidirectional channel is composed of at least one thermoplastic polymer base material that has at least one surface exposed functional group. In some embodiments of the system, the thermoplastic polymer base material has at least one surface exposed functional group selected from the groups consisting of: carbonyl groups, carboxyl groups, alcohol groups, amino groups, chloride groups, styrene groups, alpha-halogenated acyl group, benzyl groups, isocyanic acid groups, and other polymers or copolymers such as vinylchloride, vinylacetate, acrylamide, polyethylene, polyethylene terephthalate acrylic acid, acrylonitrile, maleic anhydride and methylmethacrylate. In some embodiments of the system, the base material is polycarbonate. In some embodiments of the system, the fluidic device is disposable.

Provided herein is a method for treating a patient suspected of having bacteremia, endotoxemia or sepsis comprising contacting a sample of blood with the fluidic cartridge containing a multidirectional fluidic channel between at least one inlet and at least one outlet; adsorbing one or more materials of interest on at least one wall of the multidirectional fluidic channel; removing the one or more materials of interest from the sample of blood to produce treated blood; and returning said treated blood to said patient.

Provided herein is a method for diagnosing a patient suspected of having bacteremia, endotoxemia or sepsis comprising contacting a sample of fluid with a fluidic cartridge containing a multidirectional fluidic channel between at least one inlet and at least one outlet; adsorbing one or more materials of interest on at least one wall of the multidirectional fluidic channel; and detecting the presence or amount of materials of interest captured along the at least one wall of the multidirectional fluidic channel In some embodiments, the method comprises identifying the captured materials of interest through a procedure selected from the group consisting of: polymerase chain reaction (PCR), fluorescence in situ hybridization (FISH), optically active microbeads, optically active nanoparticles, and matrix-assisted laser desorption/ionization time-of-flight (MALDI-TOF). In some embodiments, the method comprises identifying the captured materials of interest through culturing methods. In some embodiments, the method comprises identifying the captured materials of interest through elution of the captured materials of interest followed by a procedure selected from the group consisting of polymerase chain reaction (PCR), fluorescence in situ hybridization (FISH), optically active microbeads, optically active nanoparticles, and/or matrix-assisted laser desorption/ionization time-of-flight (MALDI-TOF), or culturing.

Provided herein is a filter plate for the capture and adsorption of blood-borne materials of interest comprising: a helical-shaped fluidic channel with at least one inlet and at least one outlet; said helical-shaped fluidic channel comprising at least one inner wall; and a substance coating at least a portion of the at least one inner wall of the helical-shaped fluidic channel In some embodiments, the substance is selected from the group consisting of: antibodies, cross-linking agents, peptides, proteins, antibiotics, polymers, amines, polyethers, amino acids, aptamers, tumor necrosis factors, adhesion receptors, E-selectin, cytokines, chemotherapy agents, quorum sensing proteins, quorum sensing receptors, and biological agents. In some embodiments, the substance coating the channel wall comprises a fixed, covalently-bonded polypeptide antibiotic. In some embodiments, the covalently-bonded polypeptide antibiotic is polymyxin. In some embodiments, the amount of polymyxin fixed is at least 0.5 mM. In some embodiments, the amount of polymyxin fixed is about 1.0 to about 50.0 mM. In some embodiments, the covalently-bonded polypeptide antibiotic is vancomycin. In some embodiments, the amount of vancomycin fixed is at least 0.5 mM. In some embodiments, the amount of vancomycin fixed is about 1.0 to about 50.0 mM. In some embodiments, the substance coating the channel wall comprises a fixed crosslinking agent selected from the group consisting of: hexamethylene diamine, polyethylene glycol, polyethylene glycol derivatives, N-hydroxysuccinimide esters, and glycine. In some embodiments, the hexamethylene diamine crosslinking agent to be fixed to the base material is about 1% to about 20% (v/v) aqueous solution. In some embodiments, the crosslinking agent to be fixed to the base material is polyethylene glycol or a derivative substance in which the amount fixed is about 1.0 to about 50.0 mM. In some embodiments, the filter plate is multidirectional. In some embodiments, the multidirectional channel is composed of at least one thermoplastic polymer base material that has at least one surface exposed functional group. In some embodiments, the thermoplastic polymer base material has at least one surface exposed functional group selected from the groups consisting of: carbonyl groups, carboxyl groups, alcohol groups, amino groups, chloride groups, styrene groups, alpha-halogenated acyl group, benzyl groups, isocyanic acid groups, and other polymers or copolymers such as vinylchloride, vinylacetate, acrylamide, polyethylene, polyethylene terephthalate acrylic acid, acrylonitrile, maleic anhydride and methylmethacrylate. In some embodiments, the base material is polycarbonate. In some embodiments, the filter plate is disposable. In some embodiments, the multidirectional channel has a width of about 0.01 to about 1,000.0 mm. In some embodiments, the multidirectional channel has a width of about 1.0 to about 10.0 mm. In some embodiments, the multidirectional channel has a height of about 0.001 to about 100.0 mm. In some embodiments, the multidirectional channel has a height of about 0.1 to about 10.0 mm. In some embodiments, the multidirectional channel has a length of 0.1 to 10,000 mm. In some embodiments, the multidirectional channel has a length of about 1.0 to about 3,000.0 mm. In some embodiments, said multidirectional channel is spiral shaped. In some embodiments, the spiral shaped channel has an outer-most radius of curvature of about 1.0 to about 1,000.0 mm. In some embodiments, the spiral shaped channel has an outer-most radius of curvature of about 5.0 to about 100.0 mm. In some embodiments, the spiral shaped multidirectional channel has a distance between channels of 0.01 to 1,000 mm. In some embodiments, the spiral shaped multidirectional channel has a distance between the channels in the spiral of about 1.0 to about 10.0 mm. In some embodiments, said multidirectional channel is helically shaped and fabricated around a mandrel. In some embodiments, the helical shaped multidirectional channel has a radius of curvature of about 1.0 to about 1,000.0 mm. In some embodiments, the helical shaped multidirectional channel has a radius of curvature of about 5.0 to about 100.0 mm. In some embodiments, the helical shaped multidirectional channel has a pitch of about 1.0 to about 1,000.0 mm. In some embodiments, the helical shaped multidirectional channel has a pitch of about 10.0 to about 100.0 mm. In some embodiments, the helical shaped multidirectional channel is formed in a stackable plate configuration. In some embodiments, the stackable plate configuration is between 1 plate and 25 plates. In some embodiments, the stackable plate configuration is between 2 plate and 23 plates. In some embodiments, the stackable plate configuration is between 3 plate and 20 plates. In some embodiments, the helical shaped multidirectional stackable plate is fabricated using:

3-D printing; soft lithography; photolithography; injection molding; blow molding; casting; machining; turning; drilling; boring; reaming; electric discharge machining (EDM); or milling In some embodiments, the helical shaped multidirectional stackable plate configuration is assembled using bolts, adhesive, binding material, thermal expansion, resin, epoxy, an inner sleeve, an outer sleeve, a base plate, a mandrel, cover glass, curing, extrusion welding, contact welding, high frequency welding, friction welding, laser welding, ultrasonic welding, solvent welding, or casting. In some embodiments, the multidirectional channel is extruded. In some embodiments, the multidirectional channel is extruded polycarbonate tubing. In some embodiments, the multidirectional channel is enclosed. In some embodiments, the multidirectional stackable plate configuration is enclosed within a cylinder. In some embodiments, the multidirectional channel is extruded around a mandrel. In some embodiments, the multidirectional channel is injection molded polycarbonate. In some embodiments, the multidirectional channel is incorporated into a housing formed around a mandrel. In some embodiments, the multidirectional channel is incorporated into an internal surface of the housing formed around a mandrel. In some embodiments, the multidirectional channel is incorporated into an external surface of the housing formed around a mandrel. In some embodiments, the multidirectional channel is incorporated into a housing formed around a mandrel and contained within a cylinder. In some embodiments, the multidirectional channel is stackable and contained within a cylinder. In some embodiments, the multidirectional channel is stackable and contained within a cylinder, wherein a first multidirectional channel is functionalized with a first polypeptide, and wherein a second multidirectional channel is functionalized with a second polypeptide. In some embodiments, the first polypeptide comprises polymyxin. In some embodiments, the second polypeptide comprises vancomycin. In some embodiments, the stackable multidirectional channels contained within a cylinder form a single device connected using a connector tube, wherein said channels capture and remove Gram-negative bacteria, Gram-positive bacteria, and endotoxins from flowing fluids within said single device. In some embodiments, the stackable multidirectional channels contained within the cylinder forming a single device can be connected to an in-line filtration system. In some embodiments, the in-line filtration system is a dialysis system.

Provided herein is a device for the capture and adsorption of blood-borne materials of interest comprising: a sheet comprising a helical-shaped fluidic channel with at least one inlet and at least one outlet; said helical-shaped fluidic channel comprising at least one inner wall; a mandrel attached to the sheet, wherein the sheet is rolled around the mandrel to create a helical shape; and a substance coating at least a portion of the at least one inner wall of the sheet comprising the helical-shaped fluidic channel In some embodiments, the substance is selected from the group consisting of: antibodies, crosslinking agents, peptides, proteins, antibiotics, polymers, amines, polyethers, amino acids, aptamers, tumor necrosis factors, adhesion receptors, E-selectin, cytokines, chemotherapy agents, quorum sensing proteins, quorum sensing receptors, and biological agents. In some embodiments, the substance coating the channel wall comprises a fixed, covalently-bonded polypeptide antibiotic. In some embodiments, the covalently-bonded polypeptide antibiotic is polymyxin. In some embodiments, the amount of polymyxin fixed is at least 0.5 mM. In some embodiments, the amount of polymyxin fixed is about 1.0 to about 50.0 mM. In some embodiments, the covalently-bonded polypeptide antibiotic is vancomycin. In some embodiments, the amount of vancomycin fixed is at least 0.5 mM. In some embodiments, the amount of vancomycin fixed is about 1.0 to about 50.0 mM. In some embodiments, the substance coating the channel wall comprises a fixed crosslinking agent selected from the group consisting of: hexamethylene diamine, polyethylene glycol, polyethylene glycol derivatives, N-hydroxysuccinimide esters, and glycine. In some embodiments, the hexamethylene diamine crosslinking agent to be fixed to the base material is about 1% to about 20% (v/v) aqueous solution. In some embodiments, the crosslinking agent to be fixed to the base material is polyethylene glycol or a derivative substance in which the amount fixed is about 1.0 to about 50.0 mM. In some embodiments, the device is multidirectional. In some embodiments, the multidirectional channel is composed of at least one thermoplastic polymer base material that has at least one surface exposed functional group. In some embodiments, the thermoplastic polymer base material has at least one surface exposed functional group selected from the groups consisting of: carbonyl groups, carboxyl groups, alcohol groups, amino groups, chloride groups, styrene groups, alpha-halogenated acyl group, benzyl groups, isocyanic acid groups, and other polymers or copolymers such as vinylchloride, vinylacetate, acrylamide, polyethylene, polyethylene terephthalate acrylic acid, acrylonitrile, maleic anhydride and methylmethacrylate. In some embodiments, the base material is polycarbonate. In some embodiments, the device is disposable. In some embodiments, the multidirectional channel has a width of about 0.01 to about 1,000.0 mm. In some embodiments, the multidirectional channel has a width of about 1.0 to about 10.0 mm. In some embodiments, the multidirectional channel has a height of about 0.001 to about 100.0 mm. In some embodiments, the multidirectional channel has a height of about 0.1 to about 10.0 mm. In some embodiments, the multidirectional channel has a length of 0.1 to 10,000 mm. In some embodiments, the multidirectional channel has a length of about 1.0 to about 3,000.0 mm. In some embodiments, said multidirectional channel is spiral shaped. In some embodiments, the spiral shaped channel has an outer-most radius of curvature of about 1.0 to about 1,000.0 mm. In some embodiments, the spiral shaped channel has an outer-most radius of curvature of about 5.0 to about 100.0 mm. In some embodiments, the spiral shaped multidirectional channel has a distance between channels of 0.01 to 1,000 mm. In some embodiments, the spiral shaped multidirectional channel has a distance between the channels in the spiral of about 1.0 to about 10.0 mm. In some embodiments, said multidirectional channel is helically shaped and fabricated around a mandrel. In some embodiments, the helical shaped multidirectional channel has a radius of curvature of about 1.0 to about 1,000.0 mm. In some embodiments, the helical shaped multidirectional channel has a radius of curvature of about 5.0 to about 100.0 mm. In some embodiments, the helical shaped multidirectional channel has a pitch of about 1.0 to about 1,000.0 mm. In some embodiments, the helical shaped multidirectional channel has a pitch of about 10.0 to about 100.0 mm. In some embodiments, the sheet is rolled around the mandrel between 1 and 100 times. In some embodiments, the sheet is rolled around the mandrel between 1 and 20 times. In some embodiments, the sheet is rolled around the mandrel between 1 and 5 times. In some embodiments, the sheet is fabricated using: 3-D printing; soft lithography; photolithography; injection molding; blow molding; casting; machining; turning; drilling; boring; reaming; electric discharge machining (EDM); or milling. In some embodiments, the device is assembled using bolts, adhesive, binding material, thermal expansion, resin, epoxy, an inner sleeve, an outer sleeve, a base plate, cover glass, curing, extrusion welding, contact welding, high frequency welding, friction welding, laser welding, ultrasonic welding, solvent welding, or casting. In some embodiments, the multidirectional channel is enclosed. In some embodiments, the device is enclosed within a cylinder. In some embodiments, a first multidirectional channel is functionalized with a first polypeptide, and wherein a second multidirectional channel is functionalized with a second polypeptide. In some embodiments, the first polypeptide comprises polymyxin. In some embodiments, the second polypeptide comprises vancomycin. In some embodiments, the device is contained within a cylinder form a single device connected using a connector tube, wherein said channels capture and remove Gram-negative bacteria, Gram-positive bacteria, and endotoxins from flowing fluids within said single device. In some embodiments, the stackable multidirectional channels contained within the cylinder forming a single device can be connected to an in-line filtration system. In some embodiments, the in-line filtration system is a dialysis system.

INCORPORATION BY REFERENCE

All publications, patents, and patent applications mentioned in this specification are herein incorporated by reference to the same extent as if each individual publication, patent, or patent application was specifically and individually indicated to be incorporated by reference. This application expressly incorporates herein by reference the contents of PCT Application No. PCT/US17/41038.

BRIEF DESCRIPTION OF FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 15 summarizes the capture capacity of the bacteria adsorbent device using a variety of bacterial strains;

DETAILED DESCRIPTION

Figure 1:
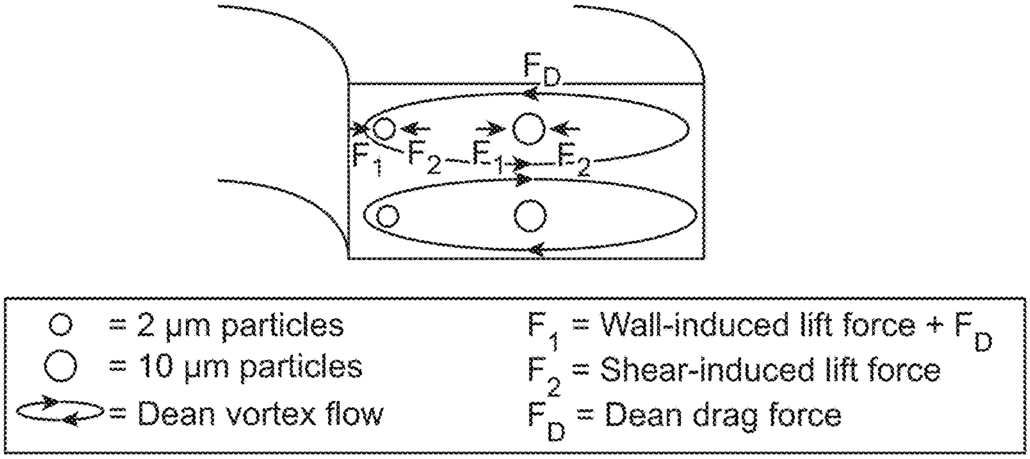
FIG. 1 is a representation of particles flowing through a channel and associated forces.

An endotoxin is a lipopolysaccharide derived from cell walls of Gram-negative bacteria. The presence of endotoxin, Gram-positive bacteria, and/or Gram-negative bacteria in blood initiates a cascade of local and systemic regulatory mechanisms that can result in sepsis. Sepsis, defined as a life-threatening organ dysfunction caused by a dysregulated host response to infection, afflicts over one million Americans annually and has an associated mortality rate ranging from 25-50%. Sepsis is the leading cause of death in the critically ill in the United States, costing the United States over $20 billion annually As the average life expectancy increases and the number of invasive procedures expand, the incidence of sepsis is rising. Currently, no specific sepsis treatment is available. Treatment of sepsis relies primarily on early recognition and rapid administration of antibiotics, fluid resuscitation, and vasoactive medications. Early, effective antibiotic therapy is essential and improves patient outcomes. However, sepsis-associated mortality remains unacceptably and persistently high, which highlights the urgent need for new sepsis therapies. Widespread use of antibiotics has significantly increased the number of drug resistant bacterial strains, suggesting that an extracorporeal device-based therapy may be more effective overall.

Much research has been done to evaluate experimental adjunct treatments for sepsis, such as extracorporeal cytokine filtration, recombinant human activated protein C, corticosteroids, human recombinant lactoferrin, and immunomodulation. Although immunomodulation has been widely anticipated, the heterogeneity of the patient population and the complexity of sepsis pathogenesis have limited advancement of these experimental approaches. Blockage of single mediators, such as interleukin-1 (IL-1) or tumor necrosis factor-alpha (TNF-α), has shown little promise in improving sepsis survival. Cytokine removal has displayed encouraging results in animal studies; however, results are believed to be a consequence of modulating other downstream mechanisms rather than the direct impact of cytokine removal. Mechanical bacterial removal using magnetic nanoparticles has been reported to improve survival of septic rodent models. Surface modification of nanoparticles using bacterial targeting ligands can lead to the efficient and reproducible capture of several important pathogenic bacteria. However, these approaches suffer from potential limitations in scale-up for treatment of large living systems and uncertain regulatory hurdles in regard to blood contact with nanoparticles.

Provided herein are devices, systems and methods that are a clinically translatable, alternative therapy for sepsis that can remove both the pathogenic bacteria and modulate the resulting molecular effectors to help mitigate the systemic inflammatory response characteristic of sepsis and inhibit sepsis progression. Methods and devices and systems described herein are used to capture and remove bacterial pathogens or associated toxins from fluids for the treatment of sepsis, endotoxemia, bacteremia infection, and other blood-borne diseases. Provided herein are methods, devices, and systems for removing pathogens and/or toxins from fluids by flowing fluids through a multidirectional channel that is coated with a polypeptide antibiotic and/or other materials.

Extracorporeal blood cleansing technologies for sepsis have been tested by others with little success. These technologies, in the past, have used dialysis membranes, fibers, or porous beads to capture inflammatory molecules based on size or molecular weight. However, bacteria and many other sepsis mediators are too large to be removed from the blood using these technologies. Furthermore, current extracorporeal blood cleansing technologies are prone to clogging and indiscriminate capture of healthy blood cell components. Polymyxin E, also known as colistin, is a cationic polypeptide antibiotic used for the treatment of Gram-negative infection and for detoxifying endotoxin. The positive charge of polymyxins, or colistin, allows for binding to the negatively charged outer membrane of Gram-negative pathogens and endotoxin. Although it is a powerful antibiotic, its use is limited due to its nephro- and neuro-toxicity. Therefore, its intravenous use is limited. It is known that polymyxin immobilized on beads can absorb endotoxin. However, the use of beads, nanoparticles, porous materials, and fibers has proven inefficient in the capture of endotoxin from fluids such as blood. Vancomycin is a polypeptide antibiotic that can be used for the treatment of Gram-positive infections. Vancomycin interacts with the cell wall of Gram-positive pathogens and inhibits bacterial cell wall assembly. This leads to activation of bacterial autolysins that destroy the cell wall by lysis. However, vancomycin is nephrotoxic when administered systemically. Also, none of these extracorporeal blood cleansing technologies for sepsis technologies are capable of efficient capture and adsorption of blood-borne Gram-positive and Gram-negative pathogens, both of which are root causes of sepsis.

Provided herein are devices, methods, and systems for the capture and adsorption of blood-borne materials of interest comprising a fluidic cartridge with at least one inlet and at least one outlet; a multidirectional fluidic channel between the at least one inlet and the at least one outlet; said multidirectional fluidic channel comprising at least one inner wall; and a substance coating at least a portion of the at least one inner wall of the multidirectional fluidic channel In some embodiments, the substance coating the channel wall is fixed to the channel wall. In some embodiments, the substance is selected from the group consisting of: antibodies, crosslinking agents, peptides, proteins, antibiotics, polymers, amines, polyethers, amino acids, aptamers, tumor necrosis factors, adhesion receptors, E-selectin, cytokines, chemotherapy agents, quorum sensing proteins, quorum sensing receptors, and biological agents. In some embodiments, the substance coating the channel wall comprises a covalently-bonded polypeptide antibiotic. In some embodiments, the covalently-bonded polypeptide antibiotic is a polymyxin—polymyxin B and/or polymyxin E. In some embodiments, the covalently-bonded polypeptide antibiotic is a polymyxin—polymyxin B and/or polymyxin E. In some embodiments, the amount of polymyxin fixed is about 0.5 mM to about 50 mM. In some embodiments, the amount of polymyxin fixed is at least about 0.5 mM. In some embodiments, the amount of polymyxin fixed is at most about 50 mM. In some embodiments, the amount of polymyxin fixed is about 0.5 mM to about 1 mM, about 0.5 mM to about 5 mM, about 0.5 mM to about 10 mM, about 0.5 mM to about 20 mM, about 0.5 mM to about 30 mM, about 0.5 mM to about 40 mM, about 0.5 mM to about 50 mM, about 1 mM to about 5 mM, about 1 mM to about 10 mM, about 1 mM to about 20 mM, about 1 mM to about 30 mM, about 1 mM to about 40 mM, about 1 mM to about 50 mM, about 5 mM to about 10 mM, about 5 mM to about 20 mM, about 5 mM to about 30 mM, about 5 mM to about 40 mM, about 5 mM to about 50 mM, about 10 mM to about 20 mM, about 10 mM to about 30 mM, about 10 mM to about 40 mM, about 10 mM to about 50 mM, about 20 mM to about 30 mM, about 20 mM to about 40 mM, about 20 mM to about 50 mM, about 30 mM to about 40 mM, about 30 mM to about 50 mM, or about 40 mM to about 50 mM. The term about, when used in reference to the amount of polymyxin, means 0.5 mM, 1 mM, 5 mM, 10 mM, 20 mM, 30 mM, 40 mM, or 50 mM. In some embodiments, the fixed, covalently-bonded polypeptide antibiotic is vancomycin. In some embodiments, the covalently-bonded polypeptide antibiotic is vancomycin. In some embodiments, the substance coating the channel wall comprises a covalently-bonded polypeptide antibiotic. Therefore, in some embodiments, the fixed, covalently-bonded polypeptide antibiotic is vancomycin. In some embodiments, the covalently-bonded polypeptide antibiotic is fixed to the channel wall. In some embodiments, the substance coating the channel wall is fixed to the channel wall. The amount of vancomycin fixed is about 0.5 mM to about 50 mM. In some embodiments, the amount of vancomycin fixed is at least about 0.5 mM. In some embodiments, the amount of vancomycin fixed is at most about 50 mM. In some embodiments, the amount of vancomycin fixed is about 0.5 mM to about 1 mM, about 0.5 mM to about 5 mM, about 0.5 mM to about 10 mM, about 0.5 mM to about 20 mM, about 0.5 mM to about 30 mM, about 0.5 mM to about 40 mM, about 0.5 mM to about 50 mM, about 1 mM to about 5 mM, about 1 mM to about 10 mM, about 1 mM to about 20 mM, about 1 mM to about 30 mM, about 1 mM to about 40 mM, about 1 mM to about 50 mM, about 5 mM to about 10 mM, about 5 mM to about 20 mM, about 5 mM to about 30 mM, about 5 mM to about 40 mM, about 5 mM to about 50 mM, about 10 mM to about 20 mM, about 10 mM to about 30 mM, about 10 mM to about 40 mM, about 10 mM to about 50 mM, about 20 mM to about 30 mM, about 20 mM to about 40 mM, about 20 mM to about 50 mM, about 30 mM to about 40 mM, about 30 mM to about 50 mM, or about 40 mM to about 50 mM. The term about, when used in reference to the amount of vancomycin, means 0.5 mM, 1 mM, 5 mM, 10 mM, 20 mM, 30 mM, 40 mM, or 50 mM.

As used herein, and unless otherwise specified, the phrase "material of interest", "materials of interest" or "disease material" means captured disease material being one or more disease materials comprising cancer cells, circulating tumor cells, peptides, beta amyloid, proteins, enzymes, toxins, diseased cells, infectious microorganisms, cells, parasites, fungi, viruses, microorganisms, bacteria, bacterial toxin, quorum sensing proteins or receptors, lipopolysaccharide, cytokines, IL-Iβ, IL-4, IL-6, IL-8, IL-10, IL-11, IL-13, IL-15, IL-16, tumor necrosis factors, procalcitonin, pathogen-associated molecular patterns, C reactive protein, or a small or protein bound biological molecule relevant to liver failure.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range. In certain embodiments, the term "about" or "approximately" means within 40.0 mm, 30.0 mm, 20.0 mm, 10.0 mm 5.0 mm 1.0 mm, 0.9 mm, 0.8 mm, 0.7 mm, 0.6 mm, 0.5 mm, 0.4 mm, 0.3 mm, 0.2 mm or 0.1 mm of a given value or range.

As used herein, the terms "comprises", "comprising", or any other variation thereof, are intended to cover a nonexclusive inclusion, such that a process, method, article, or apparatus that comprises a list of elements does not include only those elements but may include other elements not expressly listed or inherent to such process, method, article, or apparatus.

As used herein, the terms "user", "subject" or "patient" are used interchangeably. As used herein, the terms "subject" and "subjects" refers to an animal (e.g., birds, reptiles, and mammals), a mammal including a primate (e.g., a monkey, chimpanzee, and a human) and a non-primate (e.g., a camel, donkey, zebra, cow, pig, horse, cat, dog, rat, and mouse). In certain embodiments, the mammal is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100. In some embodiments, the subject or patient is a pig. In certain embodiments, the pig is 0 to 6 months old, 6 to 12 months old, 1 to 5 years old, 5 to 10 years old or 10 to 15 years old. The natural lifespan of a pig is 10-15 years.

As used herein, and unless otherwise specified, the term "transverse force", (also called the Euler force) is the tangential force that is felt in reaction to any angular acceleration. Also known as azimuthal acceleration or transverse acceleration. It is an acceleration that appears when a non-uniformly rotating reference frame is used for analysis of motion and there is variation in the angular velocity of the reference frame's axes. This definition is typically restricted to a reference frame that rotates about a fixed axis. The Euler force is related to the Euler acceleration by "F=ma", where "a" is the Euler acceleration and m is the mass of the body. Said another way, the Euler force will be felt by a person riding a merry-go-round. As the ride starts, the Euler force will be the apparent force pushing the person to the back of the horse, and as the ride comes to a stop, it will be the apparent force pushing the person towards the front of the horse. A person on a horse close to the perimeter of the merry-go-round will perceive a greater apparent force than a person on a horse closer to the axis of rotation. The Euler force is perpendicular to the centrifugal force and is in the plane of rotation.

As used herein, the terms "therapies" and "therapy" can refer to any protocol(s), method(s), compositions, formulations, and/or agent(s) that can be used in the prevention, treatment, management, or amelioration of a condition (e.g., a virus infection or a condition or symptom associated therewith, an infection other than a virus infection or a condition or symptom associated therewith, an IFN treatable disease or a condition in which the attenuated viruses can be used as a vector to induce an immune response to a particular antigen associated with the condition). In certain embodiments, the terms "therapies" and "therapy" refer to biological therapy, supportive therapy, and/or other therapies useful in treatment, management, prevention, or amelioration of a virus infection or a condition or symptom associated therewith, an infection other than a virus infection or a condition or symptom associated therewith, an IFN treatable disease or a condition in which the attenuated viruses can be used as a vector to induce an immune response to a particular antigen associated with the condition, known to one of skill in the art.

As used herein, the terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., one or more prophylactic or therapeutic agents) to "manage" a disease so as to prevent the progression or worsening of the disease.

As used herein, the terms "prevent", "preventing" and "prevention" refer to the inhibition of the development or onset of a condition (e.g.: a virus infection or a condition associated therewith, an infection other than a virus infection or a condition associated therewith, an IFN-treatable disease or a condition in which the attenuated viruses can be used as a vector to induce an immune response to a particular antigen associated with the condition), or the prevention of the recurrence, onset, or development of one or more symptoms of a condition (e.g., virus infection or a condition associated therewith, an infection other than a virus infection or a condition associated therewith, or an IFN-treatable disease), in a subject resulting from the administration of a therapy (e.g., a prophylactic or therapeutic agent), or the administration of a combination of therapies (e.g., a combination of prophylactic or therapeutic agents).

As used herein, the terms "treat," "treatment," and "treating" refer to the eradication or control of virus replication or the replication of a pathogen (e.g., a virus, a bacteria) other than virus, the reduction in the titer of virus or titer other than virus, the reduction in the numbers of a pathogen, the reduction or amelioration of the progression, severity, and/or duration of a condition (e.g., a virus infection or a condition associated therewith, an infection other than a virus infection or a condition or symptom associated therewith, an IFN treatable disease or a condition in which the attenuated viruses can be used as a vector to induce an immune response to a particular antigen associated with the condition), or the amelioration of one or more symptoms resulting from the administration of one or more therapies (including, but not limited to, the administration of one or more prophylactic or therapeutic agents).

As used herein, the terms "therapeutic agent" and "therapeutic agents" refer to any agent(s) which can be used in the prevention, treatment, management, or amelioration of a condition or a symptom thereof (e.g., an infection or a condition or symptoms associated therewith, an infection other than a virus infection or a condition or symptom associated therewith, an IFN treatable disease or a condition in which the attenuated viruses can be used as a vector to induce an immune response to a particular antigen associated with the condition). In some embodiments, a therapeutic agent is an agent which is known to be useful for, or has been or is currently being used for the prevention, treatment, management, or amelioration of a virus infection or a condition or symptoms associated therewith, an infection other than a virus infection or a condition or symptom associated therewith, an IFN treatable disease or a condition in which the attenuated viruses can be used as a vector to induce an immune response to a particular antigen associated with the condition.

As used herein, and unless otherwise specified, the term "helix" means an object having a three-dimensional shape like that of a wire wound uniformly in a single layer around a cylinder or cone, as in a corkscrew or spiral staircase. Alternative synonymous terms may comprise spiral corkscrew, curl, curlicue, twist, gyre, whorl, convolution, etc.

Geometrically a helix, as used herein can also mean a curve on a conical or cylindrical surface that would become a straight line if the surface were unrolled into a plane.

As used herein, and unless otherwise specified, the term "cylindrical" means having straight parallel sides and a circular or oval cross-section; in the shape or form of a cylinder; i.e.: "a cylindrical plastic container".

As used herein, and unless otherwise specified, the term "multidirectional" means involving, or operating in several directions, such as moving around in a curved, non-linear or radial direction, such as around a column, a cylinder, a cone, a barrel shape, a parabolic, an ellipse, a hyperbola, etc., as non-limiting examples.

Provided herein are devices, methods, and systems for the capture and adsorption of blood-borne materials of interest comprising a fluidic cartridge with at least one inlet and at least one outlet; a multidirectional fluidic channel between the at least one inlet and the at least one outlet; said multidirectional fluidic channel comprising at least one inner wall; and a substance coating at least a portion of the at least one inner wall of the multidirectional fluidic channel.

The presently described embodiments relate to a membrane-free pathogen and endotoxin adsorption device technology that is capable of continuous flow and high throughput. The working principle relies on two components: 1) polypeptide antibiotics bonded to the device channel walls and 2) fluidic flow in curved or multidirectional channel structures, such as a spiral or helix, eliminating the need for membrane-based filters or external forces. FIG. 1 is a representation of particles flowing through a channel and associated forces. Transverse force in a multidirectional channel, such as a spiral or helix, concentrates particulates according to the designed channel aspect ratio (FIG. 1). Transverse Dean flows exert a Dean drag force ($F_D$) on particles flowing in a spiral channel The competition between wall lift force, shear lift force, and Dean drag force results in differential migration of particles to unique equilibrium positions dependent of particle size (Johnston, I. D. et al. Dean flow focusing and separation of small microspheres within a narrow size range. *Microfluid. Nanofluidics* 17, 509-518 (2014)). Concentrating particulates, such as bacteria and endotoxin, near the multidirectional channel sidewalls functionalized with polypeptide antibiotics promotes capture, adsorption, and removal of these particulates from fluid through interaction with the polypeptide antibiotics. The simplicity of this design (i.e. no moving parts, no membrane-based filter, etc.) allows for incorporation of this device into other downstream processes, such as hemodialysis. This device can also serve as stand-alone blood filtration device for the diagnosis and treatment of bacteremia, endotoxemia, sepsis, and other blood-borne diseases.

The described embodiments use a curved channel of a spiral or helical device to introduce centrifugal force upon particulates (i.e. bacteria and endotoxin) flowing in a fluid (i.e. blood, saline, urine) to facilitate improved separation, capture, and removal of such particulates from the fluid. As these particulates flow through the channel, the particulates are forced toward the channel sidewalls, in a position offset from the center of the channel. The combination of centrifugal and fluidic forces in a helical- or spiral-shaped multidirectional channel allows for concentration of particulates near the polypeptide antibiotic functionalized sidewalls for capture and adsorption of bacteria and endotoxin.

The polypeptide antibiotics described herein, including polymyxin and vancomycin, are antibiotic substances having a strong affinity for the outer membrane of various strains of Gram-positive and Gram-negative bacteria, as well as an affinity for endotoxins. This allows for capture and adsorption of these biologics.

In some embodiments of the devices or systems herein, the multidirectional channel is composed of at least one thermoplastic polymer base material that has at least one surface exposed functional group. In some embodiments, the base material is polycarbonate. In some embodiments of the devices or systems herein, the multidirectional channel is made of a base material that is typically a thermoplastic polymer, such as polycarbonate. The thermoplastic polymer, in some embodiments, has surface exposed functional groups capable of fixing polymyxin, vancomycin, and other relative molecules. Examples of the exposed functional groups characteristic of the base material include carbonyl groups, carboxyl groups, alcohol groups, amino groups, chloride groups, styrene groups, alpha-halogenated acyl group, benzyl groups, isocyanic acid groups, and other polymers or copolymers such as vinylchloride, vinylacetate, acrylamide, polyethylene, polyethylene terephthalate acrylic acid, acrylonitrile, maleic anhydride, methylmethacrylate, etc.

In some embodiments, the substance coating the channel wall is fixed to the channel wall. In some embodiments, the substance is selected from the group consisting of: antibodies, crosslinking agents, peptides, proteins, antibiotics, polymers, amines, polyethers, amino acids, aptamers, tumor necrosis factors, adhesion receptors, E-selectin, cytokines, chemotherapy agents, quorum sensing proteins, quorum sensing receptors, and biological agents.

Among the materials listed, polycarbonate derivatives are suitable for the carrier due to the exposed carbonyl groups and biocompatibility. The exposed carbonyl groups on the polycarbonate surface undergo nucleophilic addition by the amine groups of the polypeptide antibiotic, such as colistin or vancomycin. This reaction results in scission of the polymer chain and the formation of a terminal carbamate. Addition of the polypeptide antibiotic containing one or more amine groups results in a polycarbonate surface decorated with the polypeptide antibiotic, which is available for subsequent capture of bacteria and/or endotoxin (FIG. 4 and FIG. 5).

Figure 4:
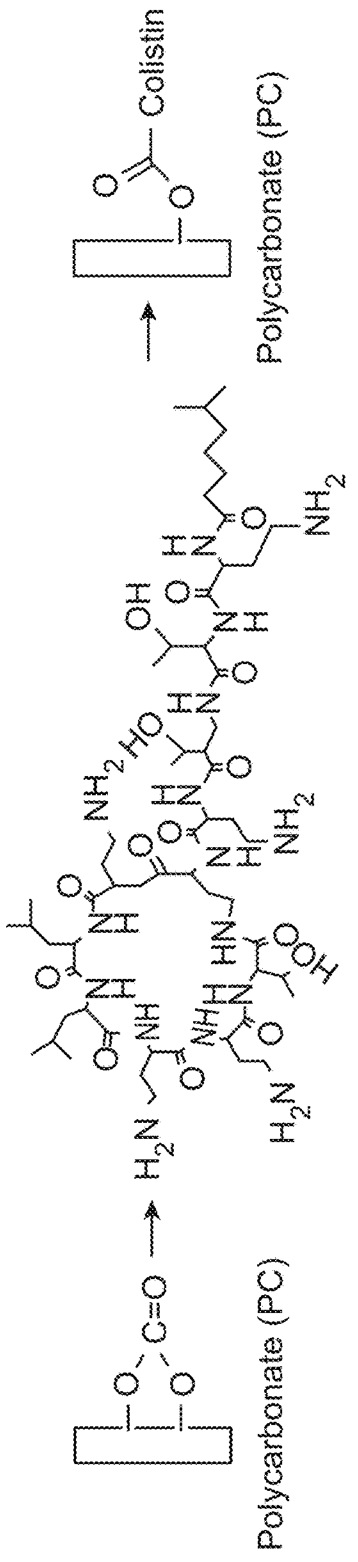
FIG. 4 illustrates chemistry of functionalization of polycarbonate surface with polymyxin E (i.e. colistin) according to the embodiments described herein.

FIG. 4 illustrates chemistry of functionalization of polycarbonate surface with polymyxin E (i.e. colistin) according to the embodiments described herein. FIG. 4 illustrates chemistry of functionalization of polycarbonate surface with polymyxin E (i.e. colistin) according to the embodiments described herein. In some embodiments, the substance coating the channel wall comprises a covalently-bonded polypeptide antibiotic. In some embodiments, the covalently-bonded polypeptide antibiotic is a polymyxin—polymyxin B and/or polymyxin E. In some embodiments, the covalently-bonded polypeptide antibiotic is a polymyxin—polymyxin B and/or polymyxin E. In some embodiments, the amount of polymyxin fixed is about 0.5 mM to about 50 mM. In some embodiments, the amount of polymyxin fixed is at least about 0.5 mM. In some embodiments, the amount of polymyxin fixed is at most about 50 mM. In some embodiments, the amount of polymyxin fixed is about 0.5 mM to about 1 mM, about 0.5 mM to about 5 mM, about 0.5 mM to about 10 mM, about 0.5 mM to about 20 mM, about 0.5 mM to about 30 mM, about 0.5 mM to about 40 mM, about 0.5 mM to about 50 mM, about 1 mM to about 5 mM, about 1 mM to about 10 mM, about 1 mM to about 20 mM, about 1 mM to about 30 mM, about 1 mM to about 40 mM, about 1 mM to about 50 mM, about 5 mM to about 10 mM, about 5 mM to about 20 mM, about 5 mM to about 30 mM, about 5 mM to about 40 mM, about 5 mM to about 50 mM, about 10 mM to about 20 mM, about 10 mM to about 30 mM, about 10 mM to about 40 mM, about 10 mM to about 50 mM, about 20 mM to about 30 mM, about 20 mM to about 40 mM, about 20 mM to about 50 mM, about 30 mM to about 40 mM, about 30 mM to about 50 mM, or about 40 mM to about 50 mM. The term about, when used in reference to the amount of polymyxin, means 0.5 mM, 1 mM, 5 mM, 10 mM, 20 mM, 30 mM, 40 mM, or 50 mM.

Figure 5:
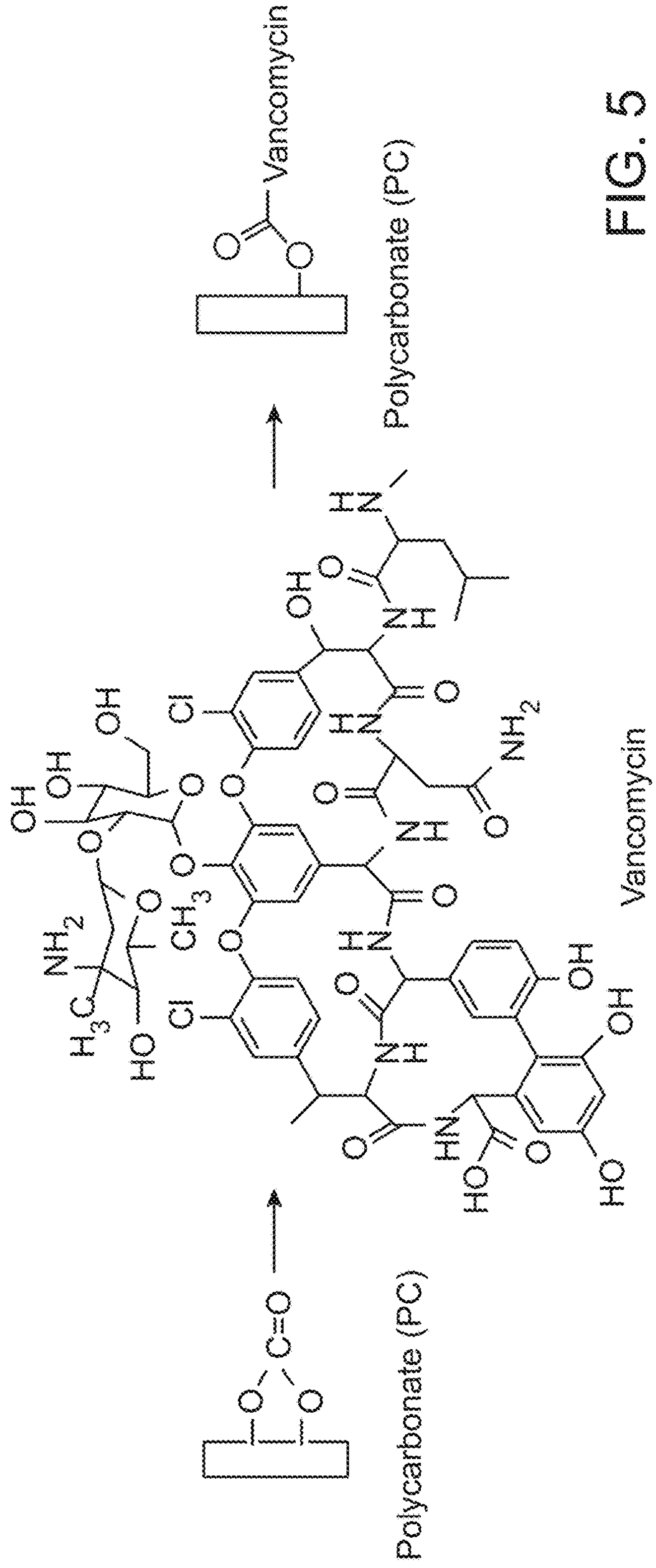
FIG. 5 illustrates chemistry of functionalization of polycarbonate surface with vancomycin according to the embodiments described herein.

FIG. 5 illustrates chemistry of functionalization of polycarbonate surface with vancomycin according to the embodiments described herein. FIG. 5 illustrates chemistry of functionalization of polycarbonate surface with vancomycin according to the embodiments described herein. In some embodiments, the fixed, covalently-bonded polypeptide antibiotic is vancomycin. In some embodiments, the covalently-bonded polypeptide antibiotic is vancomycin. In some embodiments, the substance coating the channel wall comprises a covalently-bonded polypeptide antibiotic. Therefore, in some embodiments, the fixed, covalently-bonded polypeptide antibiotic is vancomycin. In some embodiments, the covalently-bonded polypeptide antibiotic is fixed to the channel wall. In some embodiments, the substance coating the channel wall is fixed to the channel wall. The amount of vancomycin fixed is about 0.5 mM to about 50 mM. In some embodiments, the amount of vancomycin fixed is at least about 0.5 mM. In some embodiments, the amount of vancomycin fixed is at most about 50 mM. In some embodiments, the amount of vancomycin fixed is about 0.5 mM to about 1 mM, about 0.5 mM to about 5 mM, about 0.5 mM to about 10 mM, about 0.5 mM to about 20 mM, about 0.5 mM to about 30 mM, about 0.5 mM to about 40 mM, about 0.5 mM to about 50 mM, about 1 mM to about 5 mM, about 1 mM to about 10 mM, about 1 mM to about 20 mM, about 1 mM to about 30 mM, about 1 mM to about 40 mM, about 1 mM to about 50 mM, about 5 mM to about 10 mM, about 5 mM to about 20 mM, about 5 mM to about 30 mM, about 5 mM to about 40 mM, about 5 mM to about 50 mM, about 10 mM to about 20 mM, about 10 mM to about 30 mM, about 10 mM to about 40 mM, about 10 mM to about 50 mM, about 20 mM to about 30 mM, about 20 mM to about 40 mM, about 20 mM to about 50 mM, about 30 mM to about 40 mM, about 30 mM to about 50 mM, or about 40 mM to about 50 mM. The term about, when used in reference to the amount of vancomycin, means 0.5 mM, 1 mM, 5 mM, 10 mM, 20 mM, 30 mM, 40 mM, or 50 mM.

Figure 6:
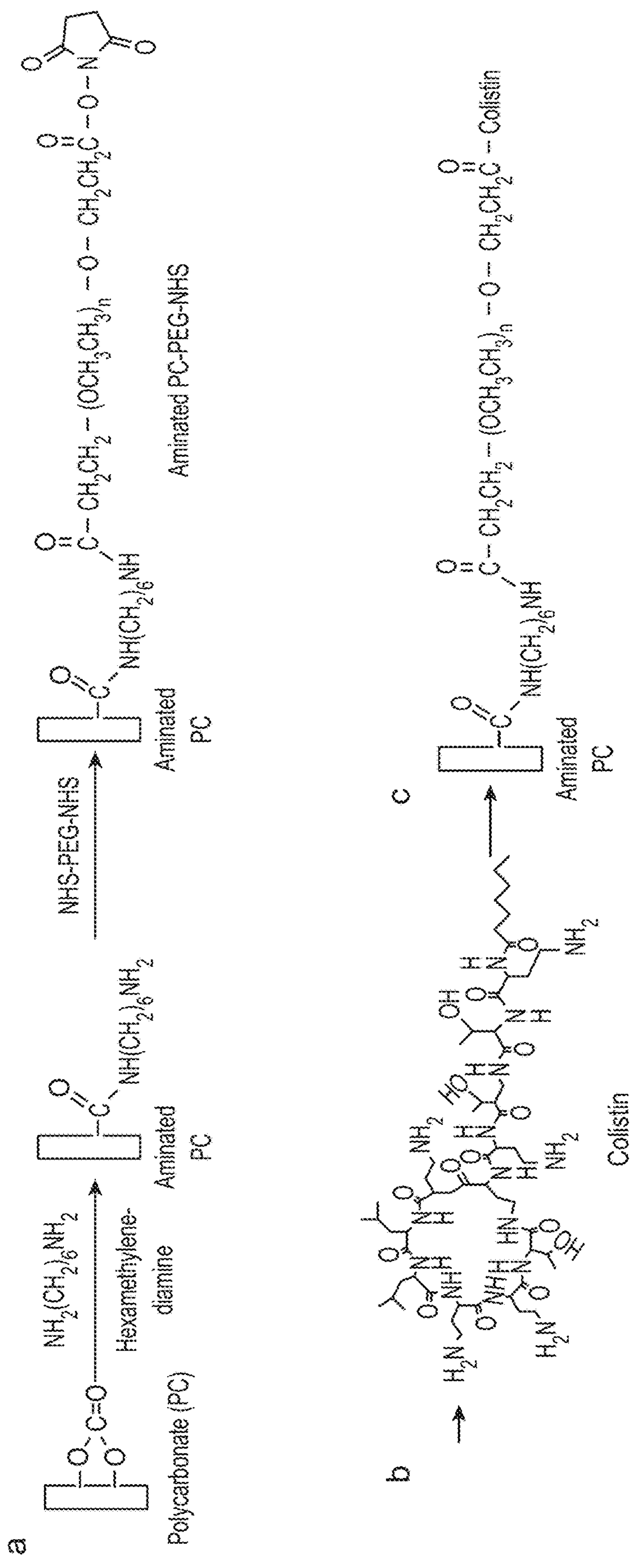
FIG. 6 illustrates an embodiment device prepared according to the description herein.
Figure 7:
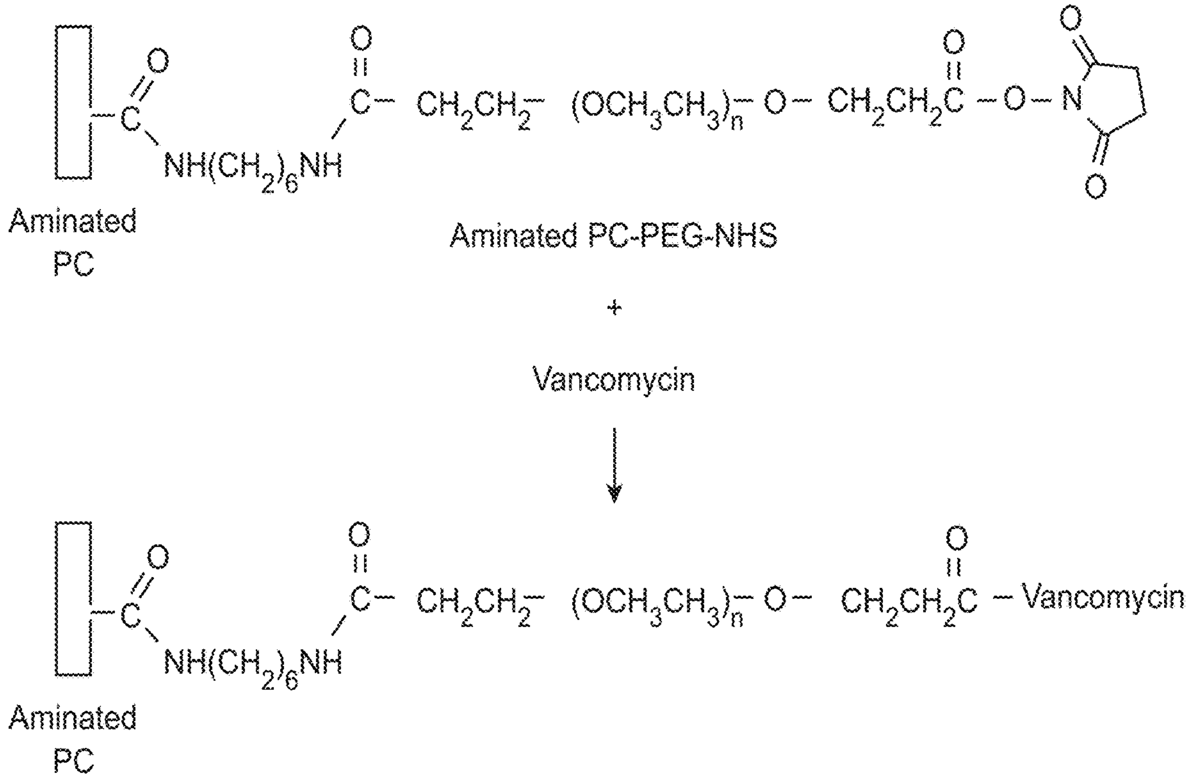
FIG. 7 illustrates an embodiment device prepared according to the description herein.

Alternatively, other functional groups conjugated to the base material surface could be attached using similar chemistry. For example, a glycine or similar structure could be used to generate a carboxylated surface. Also, hexamethylene diamine can be functionalized to the surface of the polycarbonate by nucleophilic addition by the diamine, resulting in the formation of a terminal hexylaminocarbamate. NHS esters (N-hydroxysuccinimide esters), such as NHS-Polyethylene glycol-NHS (NHS-PEG-NHS) can then be used as a cross linker and react with the amine groups exposed on the hexylaminocarbamate surface using carbodiimide chemistry. This reaction results in a surface exposed NHS group, which can then be used to react with the exposed amine groups of polypeptide antibiotics, such as vancomycin or polymyxin, forming a polypeptide functionalized surface (FIG. 6 and FIG. 7). This functionalization methodology allows for extension of the polypeptide antibiotic further from the polycarbonate surface, thereby potentially improving interaction, capture, and adsorption of target biologics, such as bacteria and endotoxin. A nitrogen atom bonded to the base material is also effective for capture and removal of Gram-negative pathogens and endotoxin.

The amount of polypeptide antibiotic substance to be fixed to the base material is, in some embodiments, more than 0.5 mM of substance and in some embodiments is from 1.0 mM to 50.0 mM substance. If the amount is less than 0.5 mM of substance, detoxifying may become ineffective, in some embodiments. In some embodiments, the substance coating the channel wall comprises a fixed crosslinking agent selected from the group consisting of: hexamethylene diamine, polyethylene glycol, polyethylene glycol derivatives, N-hydroxysuccinimide esters, and glycine. The amount of crosslinking agent, such as NHS-PEH-NHS, to be to be fixed to the base material is, in some embodiments, more than 0.1 mM of substance and in some embodiments, 1.0-50.0 mM substance.

FIG. 6 illustrates chemistry of functionalization of polycarbonate surface with a crosslinking agent and polymyxin E (i.e. colistin) according to the embodiments described herein. FIG. 7 illustrates chemistry of functionalization of polycarbonate surface with a crosslinking agent and vancomycin according to the embodiments described herein. In some embodiments, the crosslinking agent to be fixed to the base material is polyethylene glycol or a derivative substance in which the amount fixed is about 1 mM to about 50 mM. In some embodiments, the crosslinking agent to be fixed to the base material is polyethylene glycol or a derivative substance in which the amount fixed is at least about 1 mM. In some embodiments, the crosslinking agent to be fixed to the base material is polyethylene glycol or a derivative substance in which the amount fixed is at most about 50 mM. In some embodiments, the crosslinking agent to be fixed to the base material is polyethylene glycol or a derivative substance in which the amount fixed is about 1 mM to about 5 mM, about 1 mM to about 10 mM, about 1 mM to about 20 mM, about 1 mM to about 30 mM, about 1 mM to about 40 mM, about 1 mM to about 50 mM, about 5 mM to about 10 mM, about 5 mM to about 20 mM, about 5 mM to about 30 mM, about 5 mM to about 40 mM, about 5 mM to about 50 mM, about 10 mM to about 20 mM, about 10 mM to about 30 mM, about 10 mM to about 40 mM, about 10 mM to about 50 mM, about 20 mM to about 30 mM, about 20 mM to about 40 mM, about 20 mM to about 50 mM, about 30 mM to about 40 mM, about 30 mM to about 50 mM, or about 40 mM to about 50 mM. The term about, when used in reference to the amount of crosslinking agent, means 1 mM, 5 mM, 10 mM, 20 mM, 30 mM, 40 mM, or 50 mM. The amount of crosslinking agent, such as hexamethylene diamine, to be to be fixed to the base material is, in some embodiments, more than 0.1% aqueous hexamethylene diamine solution and in some embodiments is from 1% to 20% aqueous hexamethylene diamine solution. In some embodiments, the hexamethylene diamine crosslinking agent to be fixed to the base material is about 1% (v/v) aqueous solution to about 20% (v/v) aqueous solution. In some embodiments, the hexamethylene diamine crosslinking agent to be fixed to the base material is at least about 1% (v/v) aqueous solution. In some embodiments, the hexamethylene diamine crosslinking agent to be fixed to the base material is at most about 20% (v/v) aqueous solution. In some embodiments, the hexamethylene diamine crosslinking agent to be fixed to the base material is about 1% (v/v) aqueous solution to about 2% (v/v) aqueous solution, about 1% (v/v) aqueous solution to about 3% (v/v) aqueous solution, about 1% (v/v) aqueous solution to about 4% (v/v) aqueous solution, about 1% (v/v) aqueous solution to about 5% (v/v) aqueous solution, about 1% (v/v) aqueous solution to about 10% (v/v) aqueous solution, about 1% (v/v) aqueous solution to about 15% (v/v) aqueous solution, about 1% (v/v) aqueous solution to about 20% (v/v) aqueous solution, about 2% (v/v) aqueous solution to about 3% (v/v) aqueous solution, about 2% (v/v) aqueous solution to about 4% (v/v) aqueous solution, about 2% (v/v) aqueous solution to about 5% (v/v) aqueous solution, about 2% (v/v) aqueous solution to about 10% (v/v) aqueous solution, about 2% (v/v) aqueous solution to about 15% (v/v) aqueous solution, about 2% (v/v) aqueous solution to about 20% (v/v) aqueous solution, about 3% (v/v) aqueous solution to about 4% (v/v) aqueous solution, about 3% (v/v) aqueous solution to about 5% (v/v) aqueous solution, about 3% (v/v) aqueous solution to about 10% (v/v) aqueous solution, about 3% (v/v) aqueous solution to about 15% (v/v) aqueous solution, about 3% (v/v) aqueous solution to about 20% (v/v) aqueous solution, about 4% (v/v) aqueous solution to about 5% (v/v) aqueous solution, about 4% (v/v) aqueous solution to about 10% (v/v) aqueous solution, about 4% (v/v) aqueous solution to about 15% (v/v) aqueous solution, about 4% (v/v) aqueous solution to about 20% (v/v) aqueous solution, about 5% (v/v) aqueous solution to about 10% (v/v) aqueous solution, about 5% (v/v) aqueous solution to about 15% (v/v) aqueous solution, about 5% (v/v) aqueous solution to about 20% (v/v) aqueous solution, about 10% (v/v) aqueous solution to about 15% (v/v) aqueous solution, about 10% (v/v) aqueous solution to about 20% (v/v) aqueous solution, or about 15% (v/v) aqueous solution to about 20% (v/v) aqueous solution. The term about, when used in reference to the amount of the hexamethylene diamine crosslinking agent aqueous solution, means 1% (v/v) aqueous solution, 2% (v/v) aqueous solution, 3% (v/v) aqueous solution, 4% (v/v) aqueous solution, 5% (v/v) aqueous solution, 10% (v/v) aqueous solution, 15% (v/v) aqueous solution, or 20% (v/v) aqueous solution.

Embodiments of a multidirectional fluidic channel as described herein may comprise various geometries including without limitation those illustrated in FIGS. 8A, 8B, 9A, 9B, 9C, 17, 18, 21A, 21B, 21C, 21D, 22A, 22B, 23A, 23B, 24A, 24B, 25A, 25B, 25C, 26A, 26B, 27A, 27B, and 28. The multidirectional channel, in some embodiments, has an internal channel surface area of 0.001 square meters ($m^2$) to 100 $m^2$. The multidirectional channel, in some embodiments, has a surface area of from 0.001 $m^2$ to 10 $m^2$, as well as exposed functional groups being capable of fixing polymyxin and vancomycin. A surface area too large (beyond the maximum of 100 $m^2$ or 10 $m^2$, for example depending on the embodiment) increases the pressure drop of the fluid (e.g. blood) passed through the device too much, and a surface area that is too small (below 0.001 $m^2$) makes the detoxifying capacity of the device insufficient in removing the bacteria and/or pathogens, at least. The pressure drop is in some embodiments, less than 10 pounds per square inch (psi) [69 kilopascals (kPa)], and in some embodiments less than 3 psi [21 kPa].

The internal channel surface area may comprise the area of the entire surface coated by the substance. The multidirectional channel, in some embodiments, has an internal channel surface area of 0.001 $m^2$ to 80 $m^2$, 0.001 $m^2$ to 70 $m^2$, 0.001 $m^2$ to 60 $m^2$, 0.001 $m^2$ to 50 $m^2$, 0.001 $m^2$ to 40 $m^2$, 0.001 $m^2$ to 30 $m^2$, 0.001 $m^2$ to 25 $m^2$, 0.001 $m^2$ to 20 $m^2$, 0.001 $m^2$ to 19 $m^2$, 0.001 $m^2$ to 18 $m^2$, 0.001 $m^2$ to 17 $m^2$, 0.001 $m^2$ to 16 $m^2$, 0.001 $m^2$ to 15 $m^2$, 0.001 $m^2$ to 14 $m^2$, 0.001 $m^2$ to 13 $m^2$, 0.001 $m^2$ to 12 $m^2$, 0.001 $m^2$ to 11 $m^2$, 0.01 $m^2$ to 20 $m^2$, 0.01 $m^2$ to 19 $m^2$, 0.01 $m^2$ to 18 $m^2$, 0.01 $m^2$ to 17 $m^2$, 0.01 $m^2$ to 16 $m^2$, 0.01 $m^2$ to 15 $m^2$, 0.01 $m^2$ to 14 $m^2$, 0.01 $m^2$ to 13 $m^2$, 0.01 $m^2$ to 12 $m^2$, 0.01 $m^2$ to 11 $m^2$, 0.01 $m^2$ to 10 $m^2$, 0.01 $m^2$ to 100 $m^2$, 0.01 $m^2$ to 80 $m^2$, 0.01 $m^2$ to 70 $m^2$, 0.01 $m^2$ to 60 $m^2$, 0.01 $m^2$ to 50 $m^2$, 0.01 $m^2$ to 40 $m^2$, 0.01 $m^2$ to 30 $m^2$, 0.01 $m^2$ to 25 $m^2$, 0.1 $m^2$ to 20 $m^2$, 0.1 $m^2$ to 19 $m^2$, 0.1 $m^2$ to 18 $m^2$, 0.1 $m^2$ to 17 $m^2$, 0.1 $m^2$ to 16 $m^2$, 0.1 $m^2$ to 15 $m^2$, 0.1 $m^2$ to 14 $m^2$, 0.1 $m^2$ to 13 $m^2$, 0.1 $m^2$ to 12 $m^2$, 0.1 $m^2$ to 11 $m^2$, 0.1 $m^2$ to 10 $m^2$, 0.1 $m^2$ to 100 $m^2$, 0.1 $m^2$ to 80 $m^2$, 0.1 $m^2$ to 70 $m^2$, 0.1 $m^2$ to 60 $m^2$, 0.1 $m^2$ to 50 $m^2$, 0.1 $m^2$ to 40 $m^2$, 0.1 $m^2$ to 30 $m^2$, 0.1 $m^2$ to 25 $m^2$, 1 $m^2$ to 20 $m^2$, 1 $m^2$ to 19 $m^2$, 1 $m^2$ to 18 $m^2$, 1 $m^2$ to 17 $m^2$, 1 $m^2$ to 16 $m^2$, 1 $m^2$ to 15 $m^2$, 1 $m^2$ to 14 $m^2$, 1 $m^2$ to 13 $m^2$, 1 $m^2$ to 12 $m^2$, 1 $m^2$ to 11 $m^2$, 1 $m^2$ to 10 $m^2$, 1 $m^2$ to 100 $m^2$, 1 $m^2$ to 80 $m^2$, 1 $m^2$ to 70 $m^2$, 1 $m^2$ to 60 $m^2$, 1 $m^2$ to 50 $m^2$, 1 $m^2$ to 40 $m^2$, 1 $m^2$ to 30 $m^2$, 1 $m^2$ to 25 $m^2$, about 0.001 $m^2$ to about 100 $m^2$, or about 0.001 $m^2$ to about 10 $m^2$.

The radius of curvature may the radius of the circular arc which best approximates the curve of the coated surface of channel at a point on the outer-surface of the channel (in the direction of the Dean's wall-induced lift force). The helical-shaped multidirectional channel in some embodiments has a radius of curvature of 0.1 mm to 1,000 mm, in some embodiments has a radius of curvature of 10 mm to 500 mm, and in some embodiments has a radius of curvature of 5 mm to 100 mm. In some embodiments of the device, the spiral shaped channel has an outer-most radius of curvature of about 0.1 mm to about 1,000 mm. In some embodiments of the device, the spiral shaped channel has an outer-most radius of curvature of at least about 0.1 mm. In some embodiments of the device, the spiral shaped channel has an outer-most radius of curvature (in the direction of the Dean's wall-induced lift force) of at most about 1,000 mm. In some embodiments of the device, the spiral shaped channel has an outer-most radius of curvature of about 0.1 mm to about 10 mm, about 0.1 mm to about 50 mm, about 0.1 mm to about 100 mm, about 0.1 mm to about 500 mm, about 0.1 mm to about 1,000 mm, 1 mm to about 10 mm, about 1 mm to about 50 mm, about 1 mm to about 100 mm, about 1 mm to about 500 mm, about 1 mm to about 1,000 mm, about 10 mm to about 50 mm, about 10 mm to about 100 mm, about 10 mm to about 500 mm, about 10 mm to about 1,000 mm, about 50 mm to about 100 mm, about 50 mm to about 500 mm, about 50 mm to about 1,000 mm, about 100 mm to about 500 mm, about 100 mm to about 1,000 mm, or about 500 mm to about 1,000 mm. In some embodiments of the device, the spiral shaped channel has an outer-most radius of curvature of about 5 mm to about 100 mm. In some embodiments of the device, the spiral shaped channel has an outer-most radius of curvature of at least about 5 mm. The spiral-shaped multidirectional channel in some embodiments, has an outer-most radius of curvature of 0.1 mm to 1,000 mm, and in some embodiments, the spiral-shaped multidirectional channel has an outer-most radius of curvature of 1 mm to 500 mm, and in some embodiments, the spiral-shaped multidirectional channel has an outer-most radius of curvature of 5 mm to 100 mm. In some embodiments of the device, the spiral shaped channel has an outer-most radius of curvature of at most about 100 mm. In some embodiments of the device, the spiral shaped channel has an outer-most radius of curvature of about 5 mm to about 10 mm, about 5 mm to about 25 mm, about 5 mm to about 50 mm, about 5 mm to about 75 mm, about 5 mm to about 100 mm, about 10 mm to about 25 mm, about 10 mm to about 50 mm, about 10 mm to about 75 mm, about 10 mm to about 100 mm, about 25 mm to about 50 mm, about 25 mm to about 75 mm, about 25 mm to about 100 mm, about 50 mm to about 75 mm, about 50 mm to about 100 mm, or about 75 mm to about 100 mm.

The spiral-shaped multidirectional channel in some embodiments has a distance between channels (defined from center of channel lumen to center of channel lumen) of 0.01 mm to 1,000 mm, and in some embodiments the spiral-shaped multidirectional channel has a distance between channels of 0.1 mm to 100 mm, and in some embodiments the spiral-shaped multidirectional channel has a distance between channels of 1 mm to 10 mm. In some embodiments of the device, the spiral shaped multidirectional channel has a center-to-center distance between the channels in the spiral about 0.01 mm to about 1,000 mm. In some embodiments of the device, the spiral shaped multidirectional channel has a center-to center distance between the channels in the spiral at least about 0.01 mm. In some embodiments of the device, the spiral shaped multidirectional channel has a center-to center distance between the channels in the spiral at most about 1,000 mm. In some embodiments of the device, the spiral shaped multidirectional channel has a center-to center distance between the channels in the spiral about 0.01 mm to about 0.05 mm, about 0.01 mm to about 0.1 mm, about 0.01 mm to about 0.5 mm, about 0.01 mm to about 1 mm, about 0.01 mm to about 10 mm, about 0.01 mm to about 50 mm, about 0.01 mm to about 100 mm, about 0.01 mm to about 500 mm, about 0.01 mm to about 1,000 mm, about 0.05 mm to about 0.1 mm, about 0.05 mm to about 0.5 mm, about 0.05 mm to about 1 mm, about 0.05 mm to about 10 mm, about 0.05 mm to about 50 mm, about 0.05 mm to about 100 mm, about 0.05 mm to about 500 mm, about 0.05 mm to about 1,000 mm, about 0.1 mm to about 0.5 mm, about 0.1 mm to about 1 mm, about 0.1 mm to about 10 mm, about 0.1 mm to about 50 mm, about 0.1 mm to about 100 mm, about 0.1 mm to about 500 mm, about 0.1 mm to about 1,000 mm, about 0.5 mm to about 1 mm, about 0.5 mm to about 10 mm, about 0.5 mm to about 50 mm, about 0.5 mm to about 100 mm, about 0.5 mm to about 500 mm, about 0.5 mm to about 1,000 mm, about 1 mm to about 10 mm, about 1 mm to about 50 mm, about 1 mm to about 100 mm, about 1 mm to about 500 mm, about 1 mm to about 1,000 mm, about 10 mm to about 50 mm, about 10 mm to about 100 mm, about 10 mm to about 500 mm, about 10 mm to about 1,000 mm, about 50 mm to about 100 mm, about 50 mm to about 500 mm, about 50 mm to about 1,000 mm, about 100 mm to about 500 mm, about 100 mm to about 1,000 mm, or about 500 mm to about 1,000 mm. The term about, when used in reference to the distance between the channel in the spiral, means 0.01 mm, 0.05 mm, 0.1 mm, 0.5 mm, 1 mm, 10 mm, 50 mm, 100 mm, or 500 mm. In some embodiments of the device, the multidirectional channel is helically shaped and fabricated around a cylindrical chamber.

The pitch of the helical channel may be defined from center of channel lumen to center of channel lumen in the cylindrical axis (e.g. non-radially symmetric axis) of helical devices. The device may be cylindrical helical or conical helical. The pitch of the helical channel is in some embodiments 0.1 mm to 1,000 mm and in some embodiments has a pitch of 1 mm to 500 mm, and in some embodiments has a pitch of 1 mm to 100 mm. In some embodiments of the device, the helical shaped multidirectional channel has a pitch of about 1 mm to about 1,000 mm, with the pitch measured as the height of one complete helix turn measured parallel to the axis of the helix. In some embodiments of the device, the helical shaped multidirectional channel has a pitch of at least about 0.1 mm. In some embodiments of the device, the helical shaped multidirectional channel has a pitch of at most about 1,000 mm. In some embodiments of the device, the helical shaped multidirectional channel has a pitch of about 0.1 mm to about 5 mm, about 0.1 mm to about 10 mm, about 0.1 mm to about 50 mm, about 0.1 mm to about 100 mm, about 0.1 mm to about 500 mm, about 0.1 mm to about 1,000 mm, 1 mm to about 5 mm, about 1 mm to about 10 mm, about 1 mm to about 50 mm, about 1 mm to about 100 mm, about 1 mm to about 500 mm, about 1 mm to about 1,000 mm, about 5 mm to about 10 mm, about 5 mm to about 50 mm, about 5 mm to about 100 mm, about 5 mm to about 500 mm, about 5 mm to about 1,000 mm, about 10 mm to about 50 mm, about 10 mm to about 100 mm, about 10 mm to about 500 mm, about 10 mm to about 1,000 mm, about 50 mm to about 100 mm, about 50 mm to about 500 mm, about 50 mm to about 1,000 mm, about 100 mm to about 500 mm, about 100 mm to about 1,000 mm, or about 500 mm to about 1,000 mm. The term about, when used in reference to the pitch, means 0.1 mm, 1 mm, 5 mm, 10 mm, 50 mm, 100 mm, 500 mm, or 1,000 mm. In some embodiments of the device, the helical shaped multidirectional channel has a pitch of about 1.0 to about 100.0 mm.

In some embodiments, the cross-section of the lumen of the channel may be polygonal (e.g. square, rectangle, hexagonal, etc.) or may be ellipsoid. The channel width may be the interior surface to surface distance of the channel lumen at its widest point. The helical- and spiral-shaped multidirectional channel(s) in some embodiments have a channel width of 0.01 mm to 1,000 mm, in some embodiments the helical- and spiral-shaped multidirectional channel(s) have a channel width of 0.1 mm to 100 mm, and in some embodiments the helical- and spiral-shaped multidirectional channel(s) have a channel width of 1 mm to 10 mm. The channel height may be the widest, interior center to center distance within the lumen perpendicular to its widest point. The helical- and spiral-shaped multidirectional channel(s) in some embodiments have a channel height of 0.001 mm to 100 mm, and in some embodiments the helical- and spiral-shaped multidirectional channel(s) have a channel height of 0.01 mm to 20 mm, and in some embodiments the helical- and spiral-shaped multidirectional channel(s) have a channel height of 0.1 mm to 10 mm. The helical- and spiral-shaped multidirectional channel(s) in some embodiments have a channel length of 0.1 mm to 10,000 mm, and in some embodiments the helical- and spiral-shaped multidirectional channel(s) have a channel length of 1 mm to 5,000 mm, and in some embodiments the helical- and spiral-shaped multidirectional channel(s) have a channel length of 1 mm to 3,000 mm.

In some embodiments, the cross-section of the lumen of the channel may be polygonal (e.g. square, rectangle, hexagonal, etc.) or may be ellipsoid. The channel width may be the interior surface to surface distance of the channel lumen at its widest point. In some embodiments of the device, the multidirectional channel has a width of about 0.01 mm to about 1,000 mm. In some embodiments of the device, the multidirectional channel has a width of at least about 0.01 mm. In some embodiments of the device, the multidirectional channel has a width of at most about 1,000 mm. In some embodiments of the device, the multidirectional channel has a width of about 0.01 mm to about 0.05 mm, about 0.01 mm to about 0.1 mm, about 0.01 mm to about 0.5 mm, about 0.01 mm to about 1 mm, about 0.01 mm to about 10 mm, about 0.01 mm to about 50 mm, about 0.01 mm to about 100 mm, about 0.01 mm to about 500 mm, about 0.01 mm to about 1,000 mm, about 0.05 mm to about 0.1 mm, about 0.05 mm to about 0.5 mm, about 0.05 mm to about 1 mm, about 0.05 mm to about 10 mm, about 0.05 mm to about 50 mm, about 0.05 mm to about 100 mm, about 0.05 mm to about 500 mm, about 0.05 mm to about 1,000 mm, about 0.1 mm to about 0.5 mm, about 0.1 mm to about 1 mm, about 0.1 mm to about 10 mm, about 0.1 mm to about 50 mm, about 0.1 mm to about 100 mm, about 0.1 mm to about 500 mm, about 0.1 mm to about 1,000 mm, about 0.5 mm to about 1 mm, about 0.5 mm to about 10 mm, about 0.5 mm to about 50 mm, about 0.5 mm to about 100 mm, about 0.5 mm to about 500 mm, about 0.5 mm to about 1,000 mm, about 1 mm to about 10 mm, about 1 mm to about 50 mm, about 1 mm to about 100 mm, about 1 mm to about 500 mm, about 1 mm to about 1,000 mm, about 10 mm to about 50 mm, about 10 mm to about 100 mm, about 10 mm to about 500 mm, about 10 mm to about 1,000 mm, about 50 mm to about 100 mm, about 50 mm to about 500 mm, about 50 mm to about 1,000 mm, about 100 mm to about 500 mm, about 100 mm to about 1,000 mm, or about 500 mm to about 1,000 mm. The term about, when used in reference to the width of the multidirectional channel, means 0.01 mm, 0.05 mm, 0.1 mm, 0.5 mm, 1 mm, 10 mm, 50 mm, 100 mm, or 500 mm.

The channel height may be the widest, interior center-to-center distance within the lumen perpendicular to its widest point. In some embodiments of the device, the multidirectional channel has a height of about 0.001 mm to about 100 mm. In some embodiments of the device, the multidirectional channel has a height of at least about 0.001 mm. In some embodiments of the device, the multidirectional channel has a height of at most about 100 mm. In some embodiments of the device, the multidirectional channel has a height of about 0.001 mm to about 0.005 mm, about 0.001 mm to about 0.01 mm, about 0.001 mm to about 0.05 mm, about 0.001 mm to about 0.1 mm, about 0.001 mm to about 0.5 mm, about 0.001 mm to about 1 mm, about 0.001 mm to about 10 mm, about 0.001 mm to about 50 mm, about 0.001 mm to about 100 mm, about 0.005 mm to about 0.01 mm, about 0.005 mm to about 0.05 mm, about 0.005 mm to about 0.1 mm, about 0.005 mm to about 0.5 mm, about 0.005 mm to about 1 mm, about 0.005 mm to about 10 mm, about 0.005 mm to about 50 mm, about 0.005 mm to about 100 mm, about 0.01 mm to about 0.05 mm, about 0.01 mm to about 0.1 mm, about 0.01 mm to about 0.5 mm, about 0.01 mm to about 1 mm, about 0.01 mm to about 10 mm, about 0.01 mm to about 50 mm, about 0.01 mm to about 100 mm, about 0.05 mm to about 0.1 mm, about 0.05 mm to about 0.5 mm, about 0.05 mm to about 1 mm, about 0.05 mm to about 10 mm, about 0.05 mm to about 50 mm, about 0.05 mm to about 100 mm, about 0.1 mm to about 0.5 mm, about 0.1 mm to about 1 mm, about 0.1 mm to about 10 mm, about 0.1 mm to about 50 mm, about 0.1 mm to about 100 mm, about 0.5 mm to about 1 mm, about 0.5 mm to about 10 mm, about 0.5 mm to about 50 mm, about 0.5 mm to about 100 mm, about 1 mm to about 10 mm, about 1 mm to about 50 mm, about 1 mm to about 100 mm, about 10 mm to about 50 mm, about 10 mm to about 100 mm, or about 50 mm to about 100 mm. The term about, when used in reference to the height of the multidirectional channel, means 0.001 mm, 0.005 mm, 0.01 mm, 0.05 mm, 0.1 mm, 0.5 mm, 1 mm, 10 mm, or 50 mm.

The channel length may be the total distance traveled by the fluid while exposed to the coating. In some embodiments of the device, the multidirectional channel has a length of about 0.1 mm to about 10,000 mm. In some embodiments of the device, the multidirectional channel has a length of at least about 0.1 mm. In some embodiments of the device, the multidirectional channel has a length of at most about 10,000 mm. In some embodiments of the device, the multidirectional channel has a length of about 0.1 mm to about 0.5 mm, about 0.1 mm to about 1 mm, about 0.1 mm to about 10 mm, about 0.1 mm to about 50 mm, about 0.1 mm to about 100 mm, about 0.1 mm to about 500 mm, about 0.1 mm to about 1,000 mm, about 0.1 mm to about 5,000 mm, about 0.1 mm to about 10,000 mm, about 0.5 mm to about 1 mm, about 0.5 mm to about 10 mm, about 0.5 mm to about 50 mm, about 0.5 mm to about 100 mm, about 0.5 mm to about 500 mm, about 0.5 mm to about 1,000 mm, about 0.5 mm to about 5,000 mm, about 0.5 mm to about 10,000 mm, about 1 mm to about 10 mm, about 1 mm to about 50 mm, about 1 mm to about 100 mm, about 1 mm to about 500 mm, about 1 mm to about 1,000 mm, about 1 mm to about 5,000 mm, about 1 mm to about 10,000 mm, about 10 mm to about 50 mm, about 10 mm to about 100 mm, about 10 mm to about 500 mm, about 10 mm to about 1,000 mm, about 10 mm to about 5,000 mm, about 10 mm to about 10,000 mm, about 50 mm to about 100 mm, about 50 mm to about 500 mm, about 50 mm to about 1,000 mm, about 50 mm to about 5,000 mm, about 50 mm to about 10,000 mm, about 100 mm to about 500 mm, about 100 mm to about 1,000 mm, about 100 mm to about 5,000 mm, about 100 mm to about 10,000 mm, about 500 mm to about 1,000 mm, about 500 mm to about 5,000 mm, about 500 mm to about 10,000 mm, about 1,000 mm to about 5,000 mm, about 1,000 mm to about 10,000 mm, or about 5,000 mm to about 10,000 mm. The term about, when used in reference to length of the multidirectional channel, means 0.1 mm, 0.5 mm, 1 mm, 10 mm, 50 mm, 100 mm, 500 mm, 1,000 mm, or 5,000 mm. In some embodiments of the device, the multidirectional channel has a length of about 1.0 to about 3,000.0 mm In some embodiments of the device, the helical shaped multidirectional channel operates at a flow rate of about 1 mL/min to about 1,000 mL/min. In some embodiments of the device, the helical shaped multidirectional channel operates at a flow rate of at least about 1 mL/min. In some embodiments of the device, the helical shaped multidirectional channel operates at a flow rate of at most about 1,000 mL/min. In some embodiments of the device, the helical shaped multidirectional channel operates at a flow rate of about 1 mL/min to about 5 mL/min, about 1 mL/min to about 10 mL/min, about 1 mL/min to about 50 mL/min, about 1 mL/min to about 100 mL/min, about 1 mL/min to about 500 mL/min, about 1 mL/min to about 1,000 mL/min, about 5 mL/min to about 10 mL/min, about 5 mL/min to about 50 mL/min, about 5 mL/min to about 100 mL/min, about 5 mL/min to about 500 mL/min, about 5 mL/min to about 1,000 mL/min, about 10 mL/min to about 50 mL/min, about 10 mL/min to about 100 mL/min, about 10 mL/min to about 500 mL/min, about 10 mL/min to about 1,000 mL/min, about 50 mL/min to about 100 mL/min, about 50 mL/min to about 500 mL/min, about 50 mL/min to about 1,000 mL/min, about 100 mL/min to about 500 mL/min, about 100 mL/min to about 1,000 mL/min, or about 500 mL/min to about 1,000 mL/min. The term about, when used in reference to the flow rate, means 1 mL/min, 5 mL/min, 10 mL/min, 50 mL/min, 100 mL/min, 200 mL/min, 500 mL/min, or 1000 mL/min. In some embodiments of the device, the helical shaped multidirectional channel operates with flow rates of about 50 to about 400 mL/min.

In some embodiments, the detoxifying capacity of the devices, systems, and methods herein, alternatively called capture efficiency herein, as defined as the percent reduction of pathogenic bacteria at 1 minute compared to the starting concentration of the pathogenic bacteria in the fluid passed through the device is at least 30%, at least 35%, at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, at least about 30%, at least about 35%, at least about 40%, at least about 45%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, depending on the embodiment.

Figure 8A:
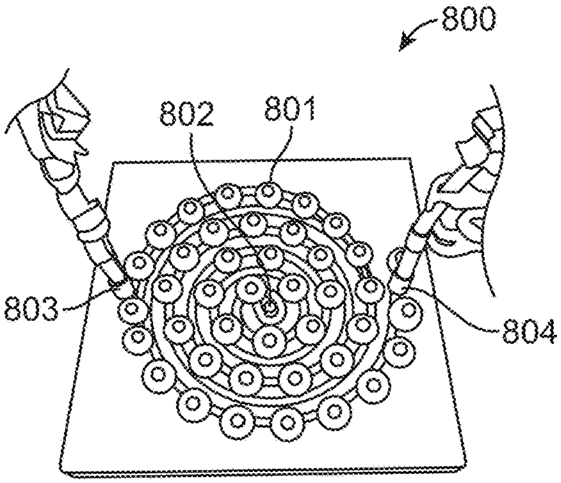
FIG. 8A illustrates a non-limiting embodiment of a spiral-shaped multidirectional channel, (channel Length=1,816 mm, Width=5.08 mm, Height=1.75 mm), fabricated using milling techniques and sealed by bolting two polycarbonate pieces together.
Figure 8B:
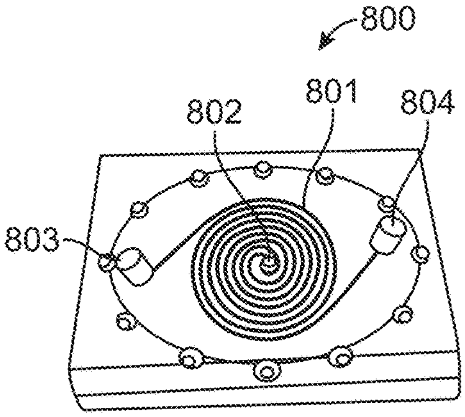
FIG. 8B illustrates another non-limiting embodiment of a spiral-shaped multidirectional channel, (channel Length=2,009 mm, Width=2 mm, Height=0.25 mm), fabricated using milling techniques and sealed by bolting two polycarbonate pieces together.

FIG. 8A and FIG. 8B illustrate a non-limiting embodiment of a multidirectional fluidic channel with a spiral shaped channel The multidirectional channel 801 may be spiral shaped. In some embodiments, spiral-shaped multidirectional channel 800 has two, 3 to 10-loop spiral channels 801 joined at an S-junction 802 to form a double spiral channel with one inlet 803 and one outlet 804 for bacterial/endotoxin removal. In some embodiments, the spiral-shaped multidirectional channel has two, 3 to 6-loop spiral channels joined at an S-junction to form a double spiral channel with one inlet and one outlet for bacterial/endotoxin removal (FIG. 8A and FIG. 8B). In some embodiments, the helical-shaped multidirectional channel comprises less than 3 loops with one inlet and one outlet for bacterial/endotoxin removal. In some embodiments, the helical-shaped multidirectional channel comprises more than 20 loops with one inlet and one outlet for bacterial/endotoxin removal. Ideally, the helical-shaped multidirectional channel is configured to provide maximum exposure in both time and surface area to enable it to capture, adsorb, and/or remove disease-causing material from biological fluids. Alternatively, the ultimate length and/or number of loops must be monitored to assure that an excessive pressure drop does not occur when the device is used in an in-line procedure with a patient.

The multidirectional channel may be a part of a device for the capture and adsorption of blood-borne materials as described herein. The multidirectional channel may comprise at least one inlet 803 and at least one outlet 804. The multidirectional channel may be a double-spiral channel 800 joined at an S-junction 802. FIG. 8A illustrates a non-limiting embodiment of a spiral-shaped multidirectional channel, (channel Length=1,816 mm, Width=5.08 mm, Height=1.75 mm), fabricated using milling techniques and sealed by bolting two polycarbonate pieces together. FIG. 8B illustrates another non-limiting embodiment of a spiral-shaped multidirectional channel, (channel Length=2,009 mm, Width=2 mm, Height=0.25 mm), fabricated using milling techniques and sealed by bolting two polycarbonate pieces together.

Figures 9A, 9B, 9C:
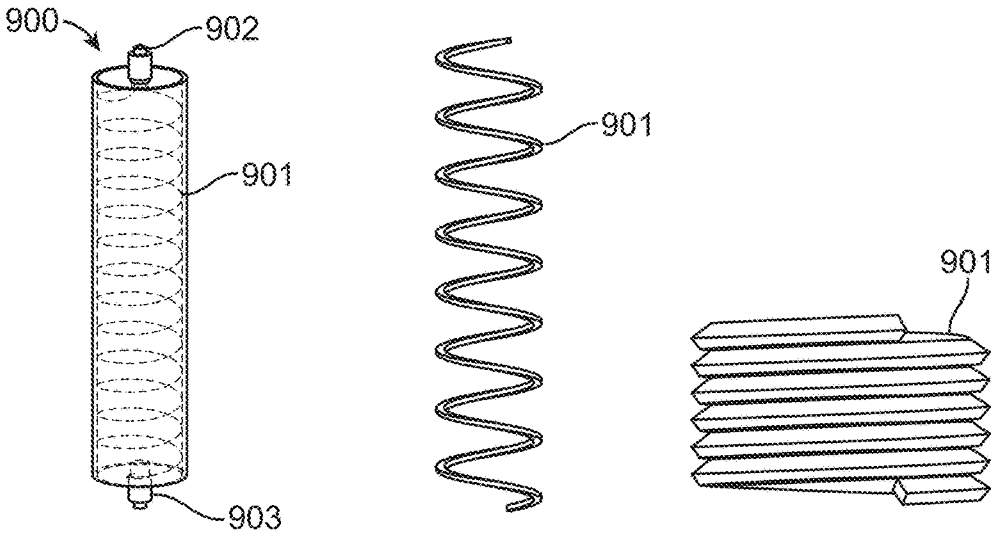
FIG. 9A illustrates a helical-shaped multidirectional channel fabricated around a cylindrical chamber or mandrel.
FIG. 9B illustrates a helical-shaped multidirectional channel not fabricated around a cylindrical chamber or mandrel.
FIG. 9C illustrates a more compact helical-shaped multidirectional channel not fabricated around a cylindrical chamber or mandrel.

FIG. 9A illustrates a non-limiting example of a helical-shaped multidirectional channel fabricated around a cylindrical chamber or mandrel. FIG. 9B illustrates a helical-shaped multidirectional channel not fabricated around a cylindrical chamber or mandrel. FIG. 9C illustrates a more compact helical-shaped multidirectional channel not fabricated around a cylindrical chamber or mandrel. The helical-shaped multidirectional channel device 900 is fabricated or extruded around or within a cylindrical chamber or mandrel (FIGS. 9A, 9B, 9C, 22A, 22B, 23B, 24A, 24B, 25A, 25B and 25C). The vertically designed device offers a constant radius of curvature and compact size and shape. A single, assembled helical-shaped multidirectional channel 901 in some embodiments has 3 to 40 loops fabricated around a mandrel with one inlet 902 and one outlet 903 for bacterial/endotoxin removal. In some embodiments, the helical-shaped multidirectional channel is composed of 3 to 20-loops fabricated around a mandrel with one inlet and one outlet for bacterial/endotoxin removal. In some embodiments, a single assembled helical-shaped channel is connected in series to another single assembled helical-shaped channel using connector tubing within housing (FIG. 22B). This allows for the capture and removal of Gram-negative, Gram-positive, and endotoxins from fluids within a single device.

Figure 17:
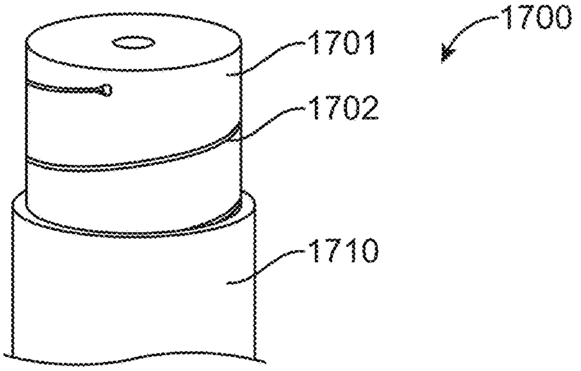
FIG. 17 illustrates a helical-shaped multidirectional channel fabricated around a cylindrical chamber or mandrel that is sealed and enclosed using an outer sleeve.
Figure 18:
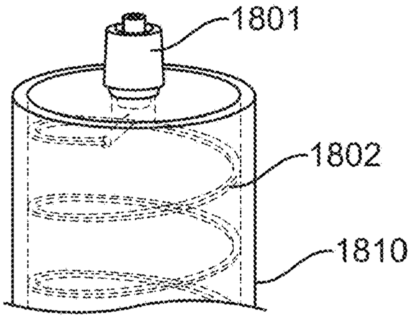
FIG. 18 illustrates the channel(s)'s inlet(s) and/or outlet(s) fitting of the channel of FIG. 17.

FIG. 17 illustrates a non-limiting example of a helical-shaped multidirectional channel fabricated around a cylindrical chamber or mandrel that is sealed and enclosed using an outer sleeve. A helical-shaped multidirectional channel device 1700, comprising a helical-shaped multidirectional channel 1702 fabricated around a cylindrical chamber or mandrel 1701, by one of the methods described above, then is sealed and enclosed using an outer sleeve 1710. FIG. 18 illustrates the channel(s)'s inlet(s) and/or outlet(s) fitting of the channel of FIG. 17. Subsequent to enclosing the helical-shaped multidirectional channel in the sealed sleeve 1810, the channel 1802 is fitted with appropriate inlet (i.e.: 1801) and outlet (not shown) fittings as illustrated in FIG. 18.

Figure 21A:
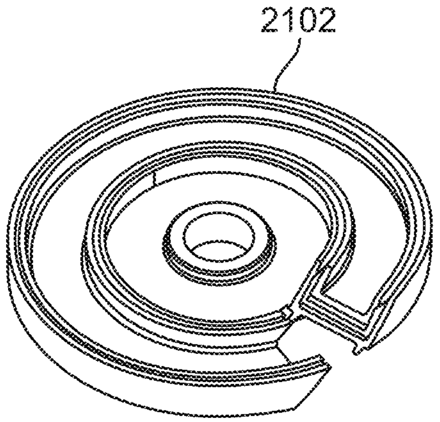
FIG. 21A illustrates an embodiment comprising a filter plate that is a helical-shaped channel fabricated using machining methods or injection molding, with each filter plate channel being 98 mm length at the outermost edge of curve.
Figure 21B:
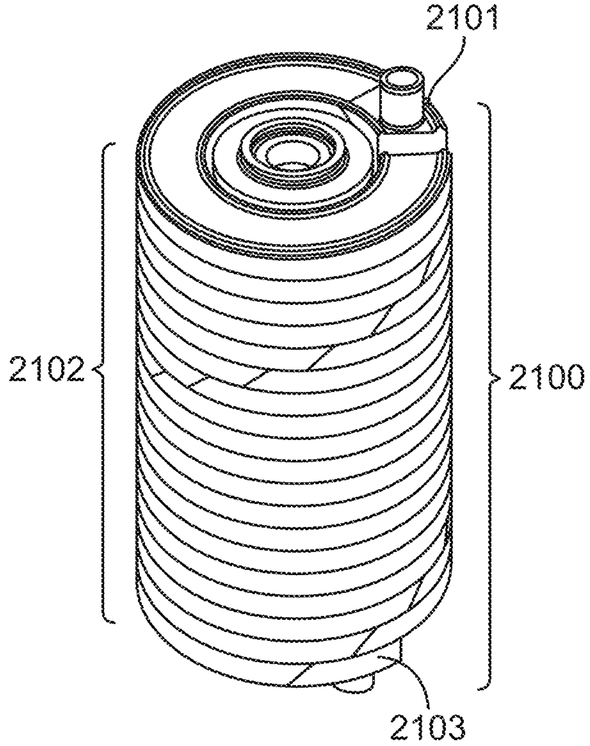
FIG. 21B illustrates an embodiment comprising multiple filter plates that are assembled, stacked, and sealed together using solvent welding and adhesive, yielding a total channel length of 1960 mm.
Figure 21C:
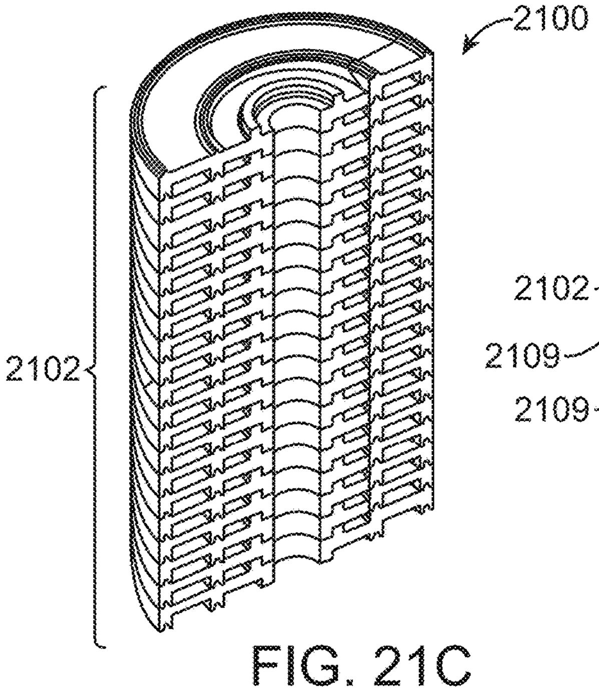
FIG. 21C illustrates a cross-sectional view of embodiment stacked helical plates of FIG. 21B.
Figure 21D:
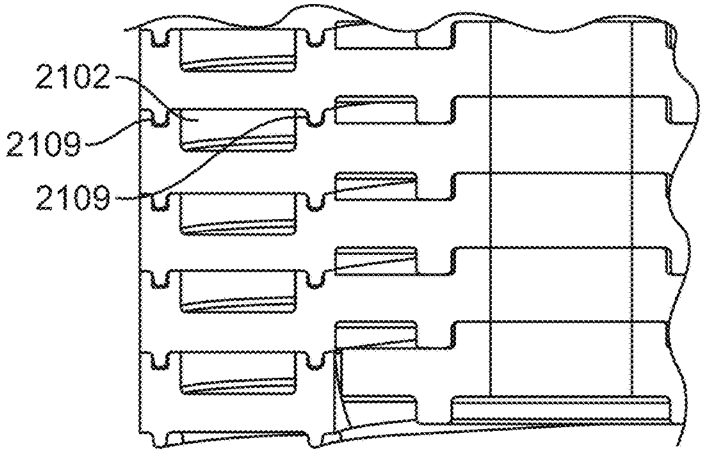
FIG. 21D illustrates sealed joints of embodiment stacked helical filter plates of FIG. 21B.

FIG. 21A illustrates a non-limiting embodiment of a device comprising a filter plate that is a helical-shaped channel fabricated using machining methods or injection molding, with each filter plate channel being 98 mm length at the outermost edge of curve. In some embodiments, as illustrated in FIG. 21A, a helical-shaped filter plate channel 2102 is fabricated using machining methods or injection molding, as described above, with each filter plate channel being 98 mm in length at the outermost edge of its curve. Expanding this concept, multiple filter plates 2100, 2102 are assemblable, stacked, and sealed together using solvent welding and adhesive, yielding a total channel length of 1,960 mm, as illustrated in FIG. 21B, to create another variant of the claimed device, also comprising an inlet adapter 2101 and outlet 2103 adapter, each attached to the helical-shaped filter plate channel 2102. FIG. 21C illustrates a cross-sectional view of an embodiment comprising stacked helical plates 2100, 2102. FIG. 21D illustrates the sealed joints 2109 on either side of each filter plate channel 2102 of an embodiment comprising stacked helical filter plates. Each plate may be made of translucent polycarbonate.

Figure 22A:
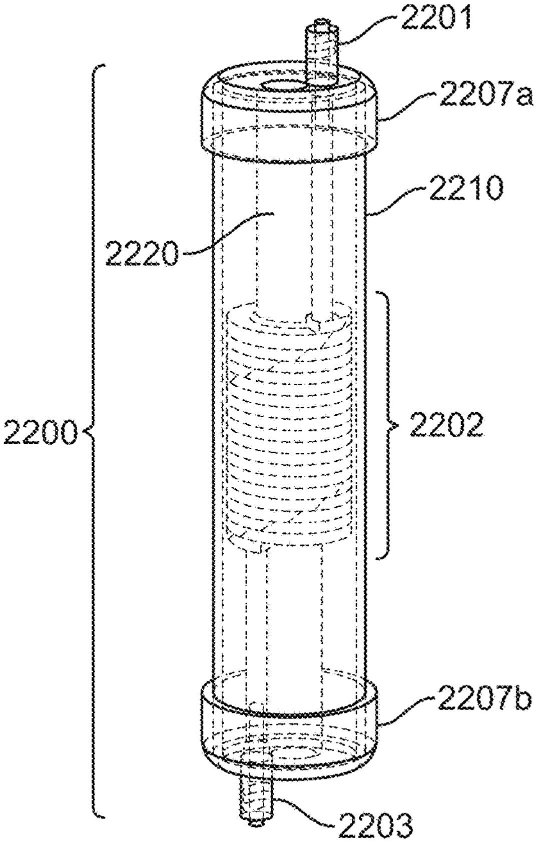
FIG. 22A illustrates an embodiment comprising stacked helical filter plates in housing and incorporating an inlet and outlet.
Figure 22B:
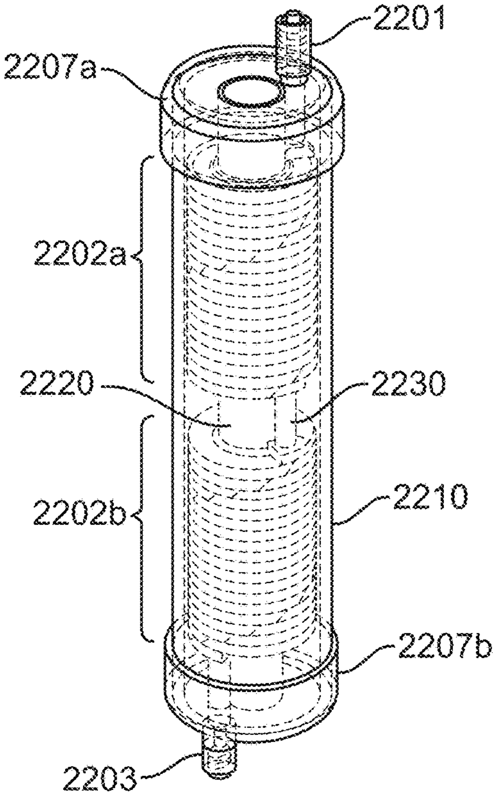
FIG. 22B illustrates an embodiment device comprising two sets of stacked helical filter plates in housing, each with different polypeptides.
Figure 28:
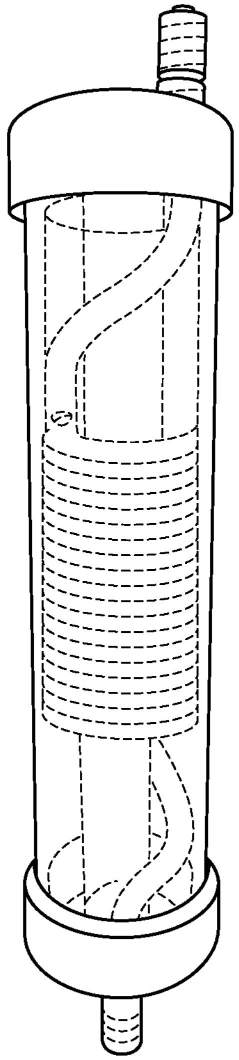
FIG. 28 illustrates an embodiment device of FIG. 22A comprising stacked helical filter plates in housing and incorporating an inlet and outlet.

Expanding on the stacked plate configuration described herein, FIG. 22A illustrates embodiment stacked helical filter plates in a sealed filter housing assembly 2200 and incorporating an inlet 2201 and outlet 2203 adapter each attached an inlet line and outlet line leading to or away from to the helical-shaped filter plate channel 2202. The assembly is housed in a cylinder 2210 around a mandrel 2220 and the entire sub-assembly is capped 2207_a_, 2207_b_ within the cylinder. FIG. 22A illustrates a non-limiting embodiment of a stacked plate configuration described herein, (channel Length=1,960 mm, diameter of assembled device=4.44 cm, number of staked spirals=20, channel Length per plate=98 mm). In the embodiment illustrated in FIG. 22A, the stacked plates may comprise 20 of the plates of FIG. 21A being stacked on each other and glued together. In some embodiments, the helical shaped multidirectional stackable plate configuration is assembled using bolts, adhesive, binding material, thermal expansion, resin, epoxy, an inner sleeve, an outer sleeve, a base plate, a mandrel, cover glass, curing, extrusion welding, contact welding, high frequency welding, friction welding, laser welding, ultrasonic welding, solvent welding, or casting. In some embodiments, the stackable plate configuration is between 1 plate and 25 plates. In some embodiments, the stackable plate configuration is between 2 plate and 23 plates. In some embodiments, the stackable plate configuration is between 3 plate and 20 plates. FIG. 28 shows a line drawing of an assembled device of the embodiment illustrated in FIG. 22A.

Further still, FIG. 22B illustrates an embodiment comprising two sets of stacked helical filter plates 2202*a*, 2202*b*, in series, in a sealed housing 2210 spaced apart by a spacer tube 2220 and with the stacked helical filter plates 2202*a*, 2202*b* connected by a connector tube 2230. The set of staked helical filter places 2202*a* and 2202*b* may be a variation or embodiment of the stacked plate configuration of FIG. 21B. The first set of stacked helical filter plates 2202*a* can be functionalized with one polypeptide such as polymyxin E, while the second set of helical plates 2202*b* can be functionalized with another polypeptide such a vancomycin. This allows for the capture and removal of Gram-negative, Gram-positive, and endotoxins from flowing fluids within a single device. The embodiment of FIG. 22B may be incorporated into a filtration system described herein.

Figure 23A:
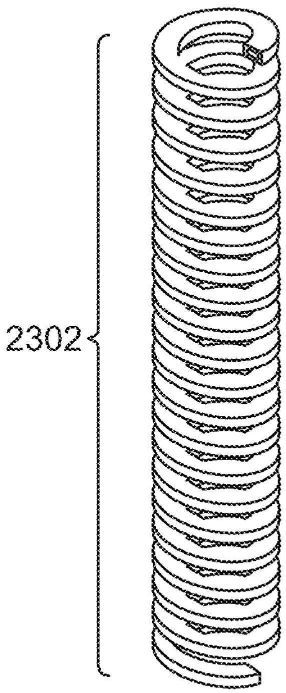
FIG. 23A illustrates an embodiment device comprising polycarbonate tubing extruded to form a helical-shaped multidirectional channel.
Figure 23B:
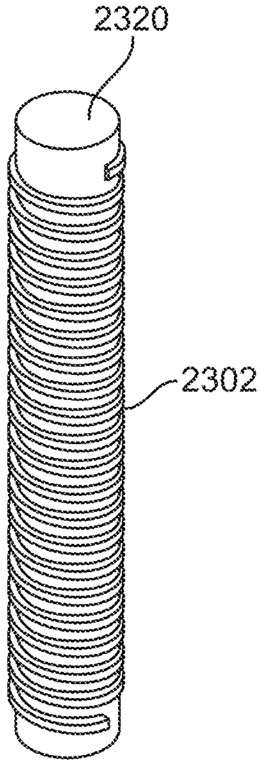
FIG. 23B illustrates an embodiment device comprising polycarbonate tubing extruded to form a helical-shaped multidirectional channel that is fabricated around a mandrel.

FIG. 23A illustrates an embodiment device comprising polycarbonate tubing extruded to form a helical-shaped multidirectional channel 2302. Whereas, FIG. 23B illustrates an embodiment device comprising polycarbonate tubing extruded to form a helical-shaped multidirectional channel 2302 that is fabricated around a mandrel 2320. In some embodiments, the multidirectional channel is extruded polycarbonate tubing. In some embodiments, the multidirectional channel is enclosed. In some embodiments, the multidirectional stackable plate configuration is enclosed within a cylinder. In some embodiments, the multidirectional channel is extruded around a mandrel. The embodiment of FIG. 23A and FIG. 23B may comprise a multidirectional fluidic channel with similar dimensions, e g channel length, pitch, diameter, etc. of other multidirectional fluidic channels described herein.

Figure 24A:
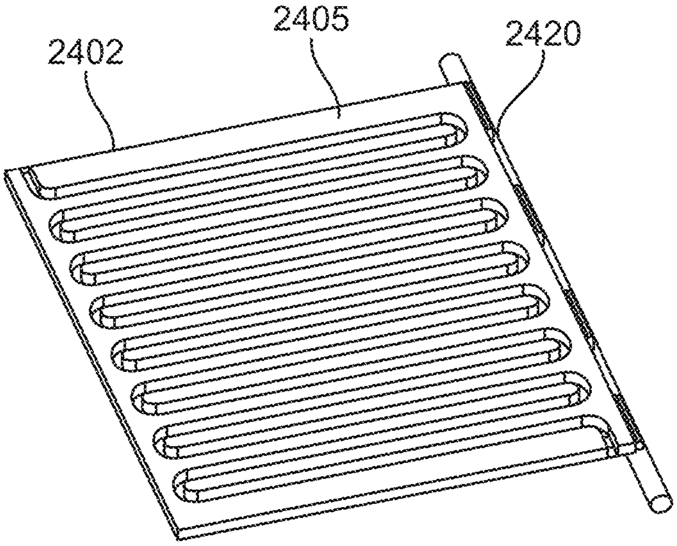
FIG. 24A illustrates an embodiment device made from an injection molded polycarbonate sheet attached to a mandrel with the helical-shaped channel incorporated into the sheet design.
Figure 24B:
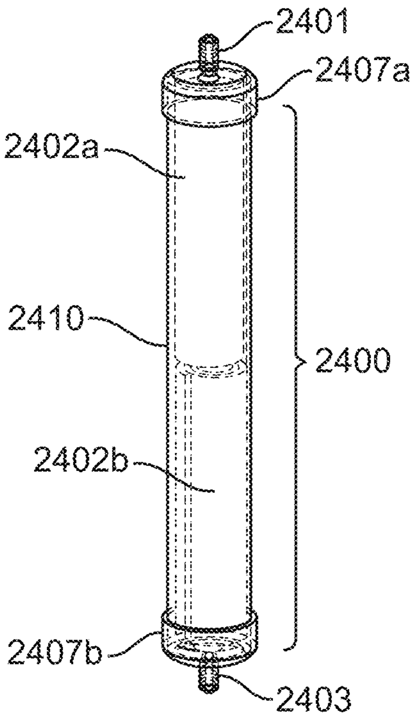
FIG. 24B illustrates an embodiment device made from a sheet rolled into a helical shape around a mandrel by first heating the polycarbonate flat sheet and then tightly rolling the flat sheet around the mandrel to create a helical shape wherein two of these rolled sheets are connected in series using connector tubing (not shown)

FIG. 24A illustrates an embodiment device made from a manufacturing method comprising forming an injection molded polycarbonate sheet 2405 attached to a mandrel 2420 with the helical-shaped channel 2402 incorporated into the sheet design. The formed sheet is then rolled into a helical shape around a mandrel by first heating the polycarbonate flat sheet and then tightly rolled around the mandrel to create a helical shape. In some embodiments, two of these rolled sheets 2402*a*, 2402*b* can be connected in series using connector tubing (not shown), as illustrated in FIG. 24B, placed in a cylinder 2410 with endcaps 2407*a*, 2407*b* having inlet 2401 and outlet 2403 adapters forming another assembly embodiment 2400. In some embodiments, the sheet is rolled around the mandrel between 1 and 100 times. In some embodiments, the sheet is rolled around the mandrel between 1 and 20 times. In some embodiments, the sheet is rolled around the mandrel between 1 and 5 times. FIG. 24A and FIG. 24B may comprise a multidirectional fluidic channel with similar dimensions, e.g. channel length, channel width, etc. of other multidirectional fluidic channels described herein.

Figure 25A:
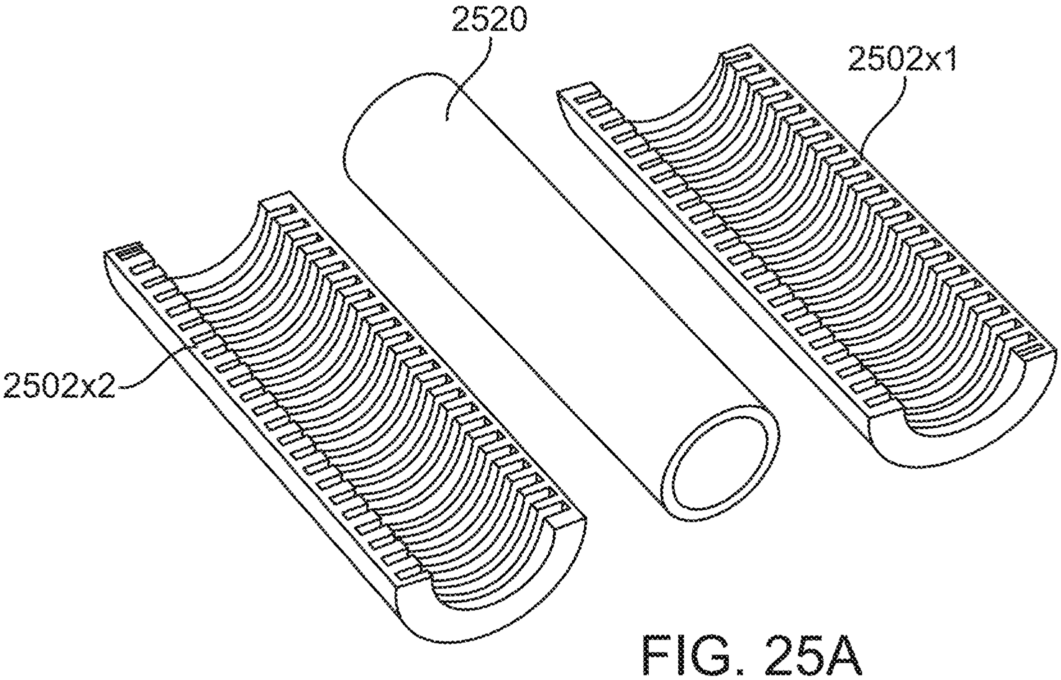
FIG. 25A illustrates an embodiment device made from injection molded polycarbonate parts that incorporate the helical-shaped channel design into the housing, while using a solid inner mandrel.
Figure 25B:
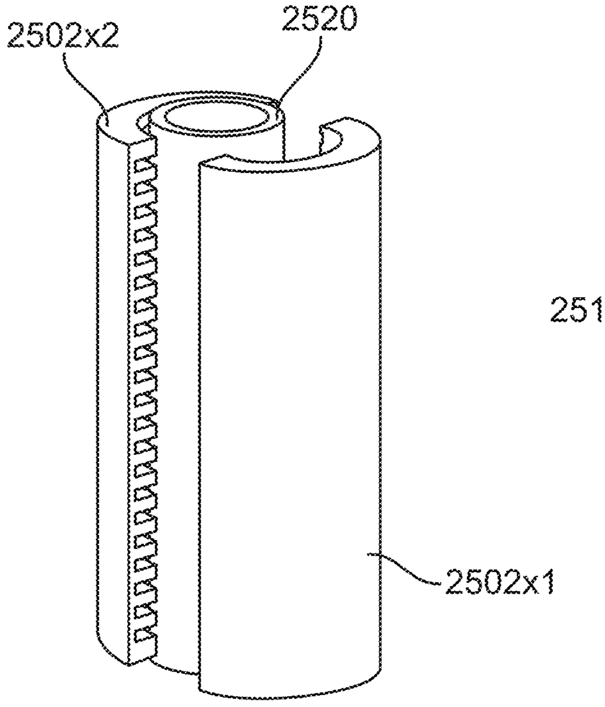
FIG. 25B illustrates a cross-sectional view of the helical housing wrapped around the mandrel of FIG. 25A.
Figure 25C:
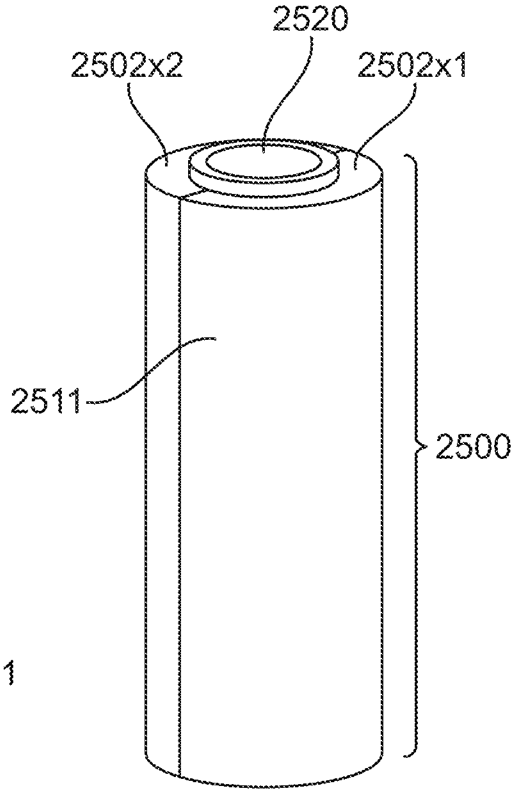
FIG. 25C illustrates an embodiment helical housing of FIG. 25A assembled around the mandrel using ultrasonic welding and/or solvent welding.

In yet another embodiment 2500, injection molded polycarbonate parts $\mathbf{2502}_{x1}$, $\mathbf{2502}_{x2}$ that incorporate the helical-shaped channel design into the housing can be generated with still another manufacturing method, then assembled, around a solid inner mandrel 2520 and sealed using ultrasonic welding and/or solvent welding 2511, as illustrated in FIGS. 25A-25C. FIG. 25A illustrates an embodiment device made from injection molded polycarbonate parts that incorporate the helical-shaped channel design into the housing, while using a solid inner mandrel. FIG. 25B illustrates a cross-sectional view of the helical housing wrapped around the mandrel of FIG. 25A. FIG. 25C illustrates an embodiment helical housing of FIG. 25A assembled around the mandrel using ultrasonic welding and/or solvent welding. FIG. 25A, FIG.25B, and FIG. 25C may comprise a multidirectional fluidic channel with similar dimensions, e.g. channel length, pitch, diameter, etc. of other multidirectional fluidic channels described herein.

Figure 26A:
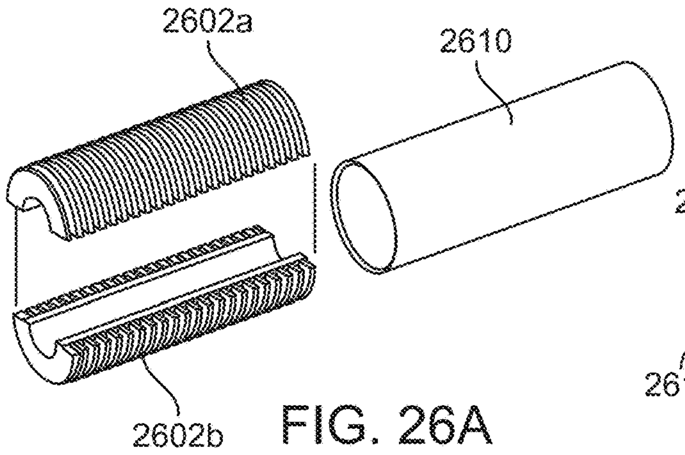
FIG. 26A illustrates an embodiment comprising an outer tube of cast or extruded polycarbonate and core A and core B injection molded polycarbonate with the helical channel design incorporated into the cores, wherein the faces of core A and core B can be coated with elastomer.
Figure 26B:
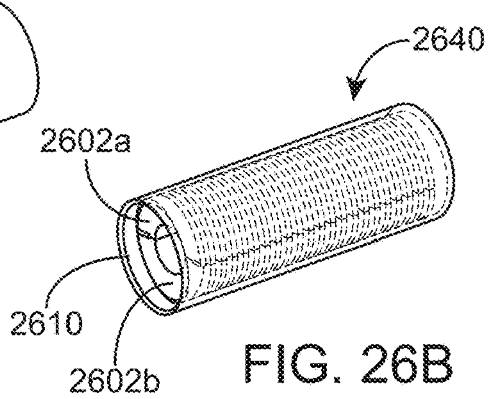
FIG. 26B illustrates the embodiment of FIG. 26A wherein the core halves are assembled and pressed into the outer tube with sealing through the use of an elastomer.

In some embodiments, the device comprises an outer tube that comprises a cast polycarbonate sleeve or extruded polycarbonate sleeve, and at least two cores, 2602*a* ("A") and 2602*b* ("B"), comprising injection molded polycarbonate with the helical channel design incorporated into exterior of the cores. The faces of the at least two cores A and B, in some embodiments, is coated with elastomer, as illustrated in FIG. 26A-FIG. 26B. Follow the coating step, the at least two cores 2602*a* and 2602*b*, (halves, as shown) are formed into an assembly 2640 and pressed into the outer tube or sleeve 2710 and sealed using an elastomer. Endcaps with inlet and outlet connections are then assembled to the ends of the tube or sleeve. FIG. 26A and FIG. 26B may comprise a multidirectional fluidic channel with similar dimensions, e.g. channel length, pitch, diameter, etc. of other multidirectional fluidic channels described herein.

Figure 27A:
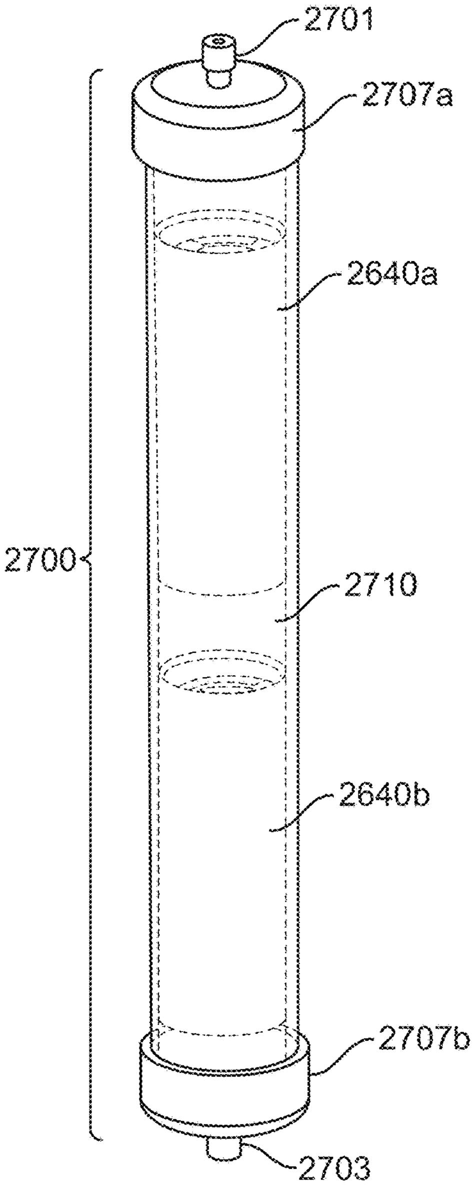
FIG. 27A illustrates an embodiment comprising two stacked and assembled injection molded polycarbonate parts that incorporate the helical-shaped channel design into the core pieces, while using a solid outer tube and which allow for the capture and removal of Gram-negative, Gram-positive, and endotoxins from flowing fluids within a single device.
Figure 27B:
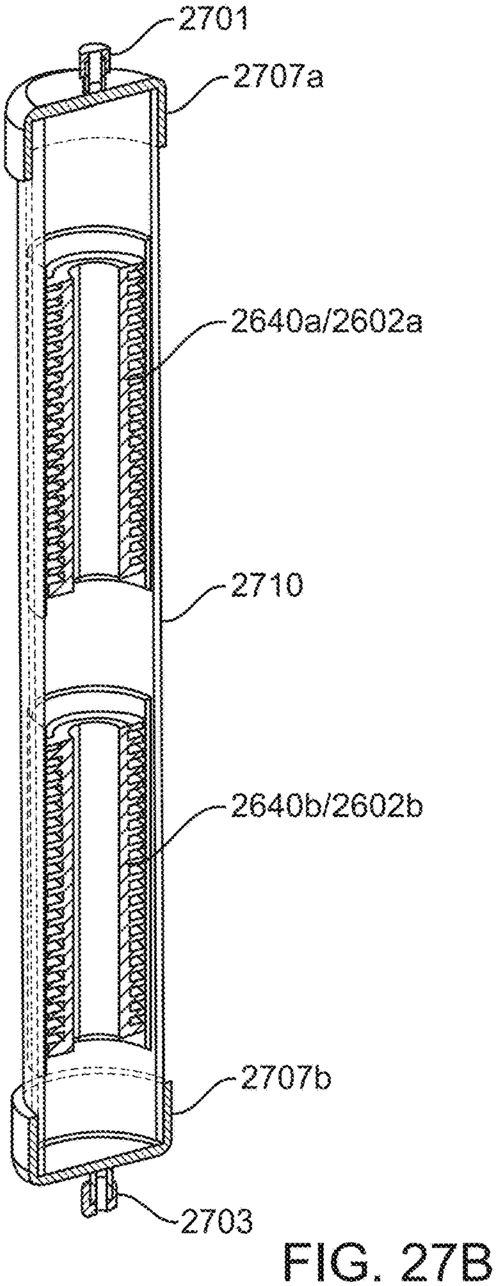
FIG. 27B illustrates a cross-sectional view of the assembled helical-core channel device of FIG. 27A.

Extending the prior concepts described in FIGS. 22B and 24B, FIG. 27A illustrates two stacked and assembled injection molded polycarbonate parts (e.g.: 2640*a*, 2640*b*) that incorporate the helical-shaped channel design into the core pieces (2640*a*/2602*a* and 2640*b*/2602*b*), while using a solid outer tube 2710. The first piece of injection molded polycarbonate containing a helical channel 2640*a*/2602*a*, can be functionalized with one polypeptide such as polymyxin E, while the second piece of injection molded polycarbonate containing a helical channel 2640*b*/2602*b* can be functionalized with another polypeptide such a vancomycin. These two pieces of injection molded polycarbonate helical channels can be connected using a connector tube. This allows for the capture and removal of Gram-negative, Gram-positive, and endotoxins from flowing fluids within a single device. FIG. 27B illustrates the cross-sectional view of the assembled helical-core channel device of FIG. 27A with endcaps 2707*a*, 2707*b* having inlet 2701 and outlet 2703 adapters forming another assembly embodiment 2700.

The claimed device can be made through the employment of any number of technologies. For example, it may be made through 3-D printing, soft lithography, photolithography, injection molding, blow molding, casting, ultrasonic welding, high frequency welding, heated tool or plate welding, solvent bonding, laser welding, spin welding, infrared welding, vibration welding, adhesive bonding, extrusion, and machining. In some embodiments, the machining methods are turning, drilling, boring, reaming, electric discharge machining and/or milling. Material may be machined or injection molded to create an enclosure of desired dimensions, such as by injection molding, extrusion, machining channel(s) as a whole or by machining halves that may be sealed and enclosed using bolts, adhesive, epoxy, welding, thermal expansion, or another means (FIGS. 8A, 8B, 9A, 9B, 9C, 17, 18, 21A, 21B, 21C, 21D, 22A, 22B, 23A, 23B, 24A, 24B, 25A, 25B, 25C, 26A, 26B, 27A, 27B, and 28). For the channel(s), tubing may be attached to the inlet(s) and outlet(s) by the use of fittings, caps, or barbed luer lock connectors (FIGS. 18, 22A, 22B, 24A, 24B, 27A, 27B, and 28). The machining may be performed on various biocompatible materials, including various grades of polycarbonate. The device may then be coated with a substance, such as polymyxin or vancomycin, using previously described methods. The coating can coat at least a portion of an inner wall of the multidirectional channel(s) through conventional means.

In some embodiments of the device, the multidirectional channel is enclosed. In some embodiments of the device, the multidirectional channel is enclosed using bolts, adhesive, binding material, thermal expansion, resin, epoxy, an inner and/or outer sleeve, a base plate, a mandrel, cover glass, curing, extrusion welding, contact welding, high frequency welding, friction welding, laser welding, ultrasonic welding, solvent welding, or casting. In some embodiments of the device, the multidirectional channel is fabricated using at least one method selected from the group consisting of: 3-D printing, soft lithography, photolithography, injection molding, blow molding, casting, ultrasonic welding, high frequency welding, heated tool or plate welding, solvent bonding, laser welding, spin welding, infrared welding, vibration welding, adhesive bonding, machining, turning, drilling, boring, reaming, electric discharge machining, or milling In some embodiments of the device, tubing is attached to the multidirectional channel inlet(s) and/or outlet(s) by the use of fittings, caps, or luer lock connectors.

Provided herein is a system for the capture and adsorption of blood-borne materials of interest comprising a fluidic cartridge with at least one inlet and at least one outlet; a multidirectional fluidic channel between the at least one inlet and the at least one outlet; said multidirectional fluidic channel comprising at least one inner wall; and a substance selected from the group consisting of: antibodies, crosslinking agents, peptides, proteins, antibiotics, polymers, amines, polyethers, amino acids, aptamers, tumor necrosis factors, adhesion receptors, E-selectin, cytokines, chemotherapy agents, quorum sensing proteins, quorum sensing receptors, and biological agents, coating, fixed and covalently bonded to at least a portion of the at least one inner wall of the multidirectional fluidic channel In some embodiments of the system, the substance coating the channel wall comprises a fixed, covalently-bonded polypeptide antibiotic. In some embodiments of the system, the covalently-bonded polypeptide antibiotic is polymyxin. In some embodiments, the covalently-bonded polypeptide antibiotic is vancomycin. In some embodiments of the system, the substance coating the channel wall comprises a fixed crosslinking agent selected from the group consisting of: hexamethylene diamine, polyethylene glycol, polyethylene glycol derivatives, N-hydroxysuccinimide esters, and glycine. In some embodiments of the system, the multidirectional channel is composed of at least one thermoplastic polymer base material that has at least one surface exposed functional group. In some embodiments of the system, the thermoplastic polymer base material has at least one surface exposed functional group selected from the groups consisting of: carbonyl groups, carboxyl groups, alcohol groups, amino groups, chloride groups, styrene groups, alpha-halogenated acyl group, benzyl groups, isocyanic acid groups, and other polymers or copolymers such as vinylchloride, vinylacetate, acrylamide, polyethylene, polyethylene terephthalate acrylic acid, acrylonitrile, maleic anhydride and methylmethacrylate. In some embodiments of the system, the base material is polycarbonate. In some embodiments of the system, the fluidic device is disposable. The system may comprise any embodiment of the multidirectional fluidic channel described herein. The system may comprise the multidirectional fluidic channel of one or more of FIGS. 8A, 8B, 9A, 9B, 9C, 17, 18, 21A, 21B, 21C, 21D, 22A, 22B, 23A, 23B, 24A, 24B, 25A, 25B, 25C, 26A, 26B, 27A, 27B, and 28.

Figure 19:
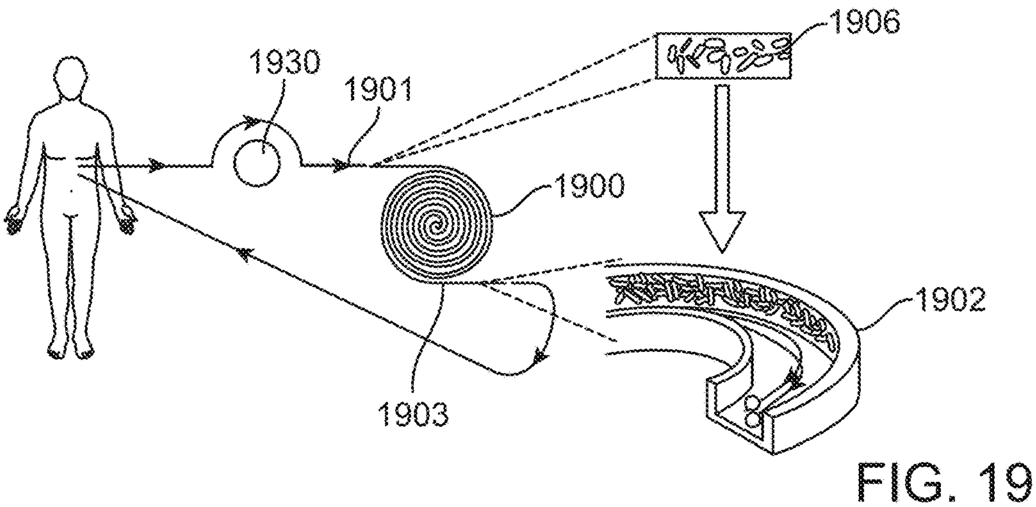
FIG. 19 illustrates example embodiment wherein whole blood infected with bacteria and/or endotoxin being pumped from a patient to the inlet of the double-spiral fluidic device that is functionalized along the channel walls with polypeptide antibiotics designed to capture bacteria and endotoxin, followed by the blood then containing only healthy material being returned to the patient.

In some embodiments, the claimed device is configurable for in-line filtration and capture such that whole blood infected with bacteria and/or endotoxin 1906 can be pumped 1930 from a patient to the inlet 1901 of the double-spiral fluidic device 1900, as illustrated in FIG. 19. The device is functionalized along the channel walls 1902 with polypeptide antibiotics designed to capture bacteria and endotoxin. Following processing through the fluidic device, the blood then containing only healthy material is returned to the patient via the outlet 1903.

Figure 20:
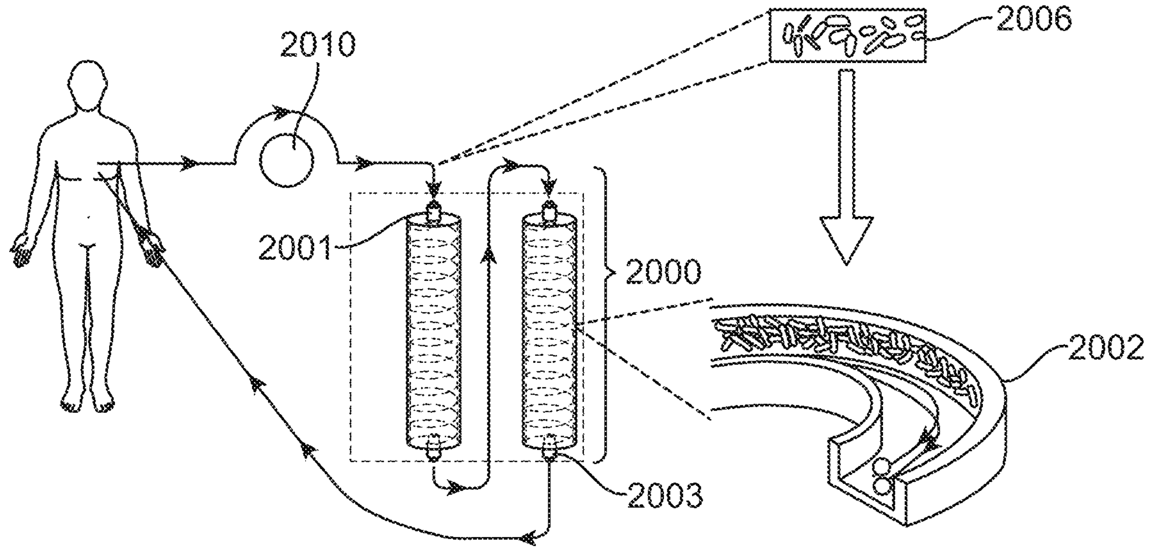
FIG. 20 illustrates example embodiment wherein whole blood infected with bacteria and/or endotoxin being pumped from a patient to the inlet of the helical fluidic devices in series.

Similarly, as illustrated in FIG. 20, is an embodiment configurable for in-line filtration and capture such that whole blood infected with bacteria and/or endotoxin can be pumped 2010 from a patient to the inlet 2001 of the helical fluidic devices in series 2000. The embodiment devices are functionalized along the channel walls 2002 with polypeptide antibiotics designed to capture bacteria and endotoxin 2006. Following processing through the fluidic devices, the blood then containing only healthy material is returned to the patient via the outlet 2003.

In some embodiments, bacteria and endotoxin are removed from blood by circulation outside the body wherein prior to return to the patient body, blood removed from the patient body or plasma components separated from blood are passed through the multidirectional bacterial and endotoxin adsorbent device as described herein, and the cleaned blood or plasma components from which bacteria and endotoxin were removed are returned to the patient body (FIG. 19).

Moreover, it should be appreciated that any of the devices described or contemplated herein may be used in series or parallel (FIG. 20).

Provided herein is a method for the capture and adsorption of materials of interest comprising bringing a sample of fluid in contact with a multidirectional, polypeptide antibiotic coated channel; adsorbing said material(s) of interest on said multidirectional channel walls; and detecting the presence or amount of said materials of interest captured within the multidirectional, polypeptide antibiotic coated channel In some embodiments of the method, a fluid sample is brought in contact with a multidirectional, polypeptide antibiotic coated channel using a pump. The method may comprise any variant, embodiment, or example of the channels described herein. In some embodiments, the pump is a peristaltic pump. In some embodiments, the pump is a syringe pump. In some embodiments of the method, a fluid sample is brought in contact with a multidirectional, polypeptide antibiotic coated channel using a syringe. In some embodiments, the polypeptide antibiotic is polymyxin. In some embodiments, the polypeptide antibiotic is vancomycin. In some embodiments of the method, heparin, sodium citrate, or other anticoagulants, are added to the fluid sample prior to being brought in contact with a multidirectional, polypeptide antibiotic coated channel In some embodiments, detection of the presence or amount of materials of interest captured within the multidirectional, polypeptide antibiotic coated channel is performed using a method selected from the group comprising: cell counting, MALDI-TOF MS (matrix assisted laser desorption ionization-time of flight mass spectrometry), mass spectrometry, PCR (polymerase chain reaction), biosensing, flow cytometry, and fluorescent labeling.

Provided herein is a method for treating a patient suspected of having bacteremia, endotoxemia or sepsis comprising contacting a sample of blood with the fluidic cartridge containing a multidirectional fluidic channel between at least one inlet and at least one outlet; adsorbing one or more materials of interest on at least one wall of the multidirectional fluidic channel; removing the one or more materials of interest from the sample of blood to produce treated blood; and returning said treated blood to said patient. The method may comprise any variant, embodiment, or example of the channels described herein.

Provided herein is a method for diagnosing a patient suspected of having bacteremia, endotoxemia or sepsis comprising contacting a sample of fluid with a fluidic cartridge containing a multidirectional fluidic channel between at least one inlet and at least one outlet; adsorbing one or more materials of interest on at least one wall of the multidirectional fluidic channel; and detecting the presence or amount of materials of interest captured along the at least one wall of the multidirectional fluidic channel The method may comprise any variant, embodiment, or example of the channels described herein. In some embodiments, the method comprises identifying the captured materials of interest through a procedure selected from the group consisting of: polymerase chain reaction (PCR), fluorescence in situ hybridization (FISH), optically active microbeads, optically active nanoparticles, and matrix-assisted laser desorption/ionization time-of-flight (MALDI-TOF). In some embodiments, the method comprises identifying the captured materials of interest through culturing methods. In some embodiments, the method comprises identifying the captured materials of interest through elution of the captured materials of interest followed by a procedure selected from the group consisting of polymerase chain reaction (PCR), fluorescence in situ hybridization (FISH), optically active microbeads, optically active nanoparticles, and/or matrix-assisted laser desorption/ionization time-of-flight (MALDI-TOF), or culturing.

Provided herein are materials used for removal of pathogens and endotoxins from fluids for transfusion medicine, sepsis treatment, bacteremia treatment, endotoxemia treatment, and other blood-borne diseases. These fluids, such as blood, may be passed or circulated through the channel(s) of the bacterial and endotoxin adsorbent device. The method may comprise any variant, embodiment, or example of the channels described herein.

Provided herein are methods in which thermoplastic tubing is coated with the polypeptide antibiotic substance. The method may comprise any variant, embodiment, or example of the channels described herein.

EXAMPLES

It is understood that the examples and embodiments described herein are for illustrative purposes only and are not intended to limit the scope of the claimed invention. It is also understood that various modifications or changes in light of the examples and embodiments described herein will be suggested to persons skilled in the art and are to be include within the spirit and purview of this application and scope of the appended claims.

The following examples utilize spiral-shaped multidirectional channel devices with the following parameters (channel Length=1,816-2,009 mm, Width=2 mm to 5.08 mm, Height=0.25-1.75 mm), fabricated using milling techniques and sealed by bolting two polycarbonate pieces together. Hexamethylene diamine solution (10% (v/v) aqueous in 100 mM borate buffer) was added to the polycarbonate channel surface for 45 minutes. Addition of the diamine results in a surface decorated with amine groups that are available for subsequent functionalization reactions.

For colistinated devices, colistin sulfate salt (0.28 g) was added to 16 mLs of a fifty-fifty distilled water/ethanol mixture (50% DiH2O/50% EtOH, v/v). The colistin solution was added to the polycarbonate-based channel and incubated within the channel at room temperature for 1 hour. Afterwards, the channel was washed with EtOH and air dried.

For devices with vancomycin, vancomycin (0.22 g) was added to 13 mLs of an ethanol/water mixture (50% $DiH_2O$/50% EtOH (v/v)). The vancomycin solution was added to the polycarbonate-based channel and incubated within the channel at room temperature for 1 hour. Afterwards, the channel was washed with EtOH and air dried.

For pegylated devices, NHS-$PEG_{1000}$-NHS (0.24 grams (g)) was added to 16 mLs of an ethanol/water mixture (50% $DiH_2O$/50% EtOH (v/v)). The NHS-$PEG_{1000}$-NHS solution was added to the polycarbonate-based channel and incubated within the channel at room temperature for 45 minutes. Afterwards, the channel was washed with EtOH and dried.

Figure 2A:
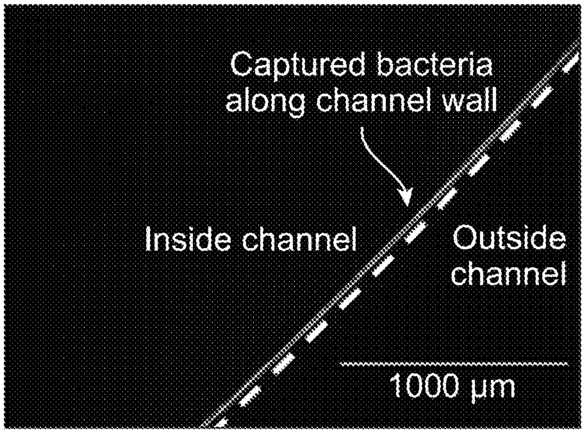
FIG. 2A illustrates adsorption of fluorescently labeled *A. baumannii* ATCC 17978 along polymyxin functionalized walls of an embodiment polycarbonate device.
Figure 2B:
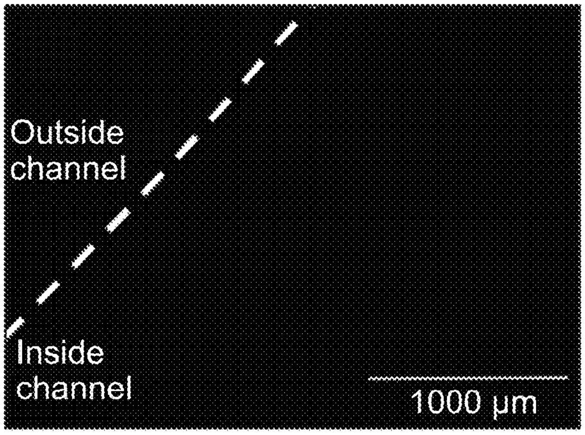
FIG. 2B illustrates absence of adsorption of fluorescently labeled *A. baumannii* ATCC 17978 along PEGylated walls of an embodiment polycarbonate device.

FIG. 2A and FIG. 2B show example implementations of a device of the present disclosure to evaluate the bacterial capture capacity a multidirectional fluidic channel using *Acinetobacter baumannii. Acinetobacter baumannii* ATCC 17978 bacterial cells were chosen as a standard specimen for qualitatively and quantitatively evaluating the bacterial capture capacity of the colistinated and polyethylene glycol (PEGylated) functionalized fluidic devices. FIG. 2A illustrates adsorption of fluorescently labeled *A. baumannii* ATCC 17978 along polymyxin functionalized walls of an embodiment polycarbonate device. Fluorescently labeled *A. baumannii* ATCC 17978 are bound to the colistinated channel walls following passage through the fluidic device at 80 mL $min^{-1}$ and subsequent washing (FIG. 2A). FIG. 2B illustrates absence of adsorption of fluorescently labeled *A. baumannii* ATCC 17978 along PEGylated walls of an embodiment polycarbonate device. Significant bacterial capture did not occur within the PEGylated spiral fluidic device, which served as a control, presumably due to the absence of colistin surface functionalization (FIG. 2B).

Figure 3A:
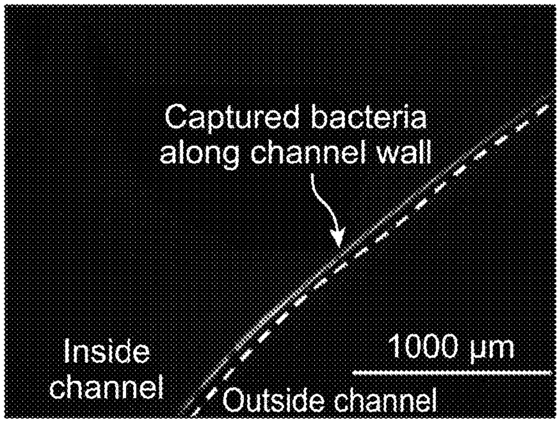
FIG. 3A illustrates adsorption of fluorescently labeled *S. aureus* ATCC 29213 along vancomycin functionalized walls of an embodiment polycarbonate device.
Figure 3B:
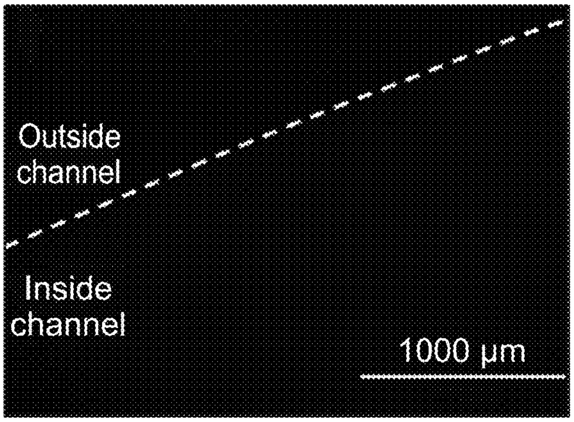
FIG. 3B illustrates absence of adsorption of fluorescently labeled *S. aureus* ATCC 29213 along PEGylated walls of an embodiment polycarbonate device.

FIG. 3A and FIG. 3B show example implementations of a device of the present disclosure to evaluate the bacterial capture capacity a multidirectional fluidic channel for *Staphylococcus aureus. Staphylococcus aureus* ATCC 29213 bacterial cells were chosen as a standard specimen for qualitatively and quantitatively evaluating the bacterial capture capacity of the vancomycin functionalized and Polyethylene glycol (PEGylated) functionalized fluidic devices. FIG. 3A illustrates adsorption of fluorescently labeled *S. aureus* ATCC 29213 along vancomycin functionalized walls of an embodiment polycarbonate device. Fluorescently labeled *S. aureus* ATCC 29213 bacterial cells are bound to the vancomycin functionalized channel walls following passage through the fluidic device at 80 mL and subsequent washing (FIG. 3A). FIG. 3B illustrates absence of adsorption of fluorescently labeled *S. aureus* ATCC 29213 along PEGylated walls of an embodiment polycarbonate device. Significant bacterial capture did not occur within the PEGylated spiral fluidic device, which served as a control, presumably due to the absence of vancomycin surface functionalization (FIG. 3B).

Figure 10A:
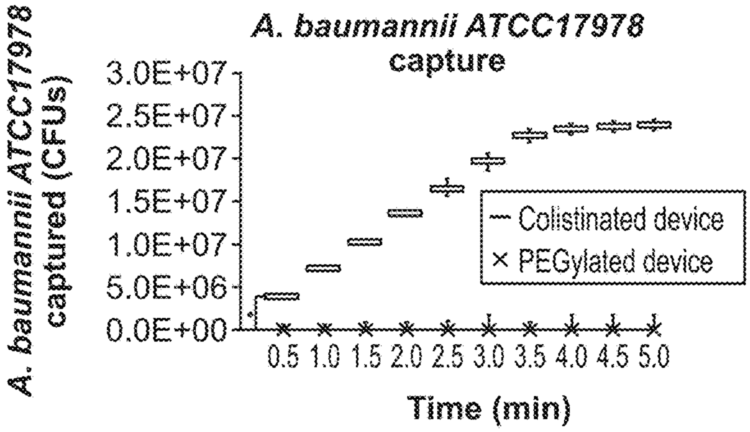
FIG. 10A illustrates a capture of *A. baumannii* ATCC 17978 when flowed through the polymyxin coated device (i.e. colistinated device) at 80 ml $min^{-1}$.
Figure 10B:
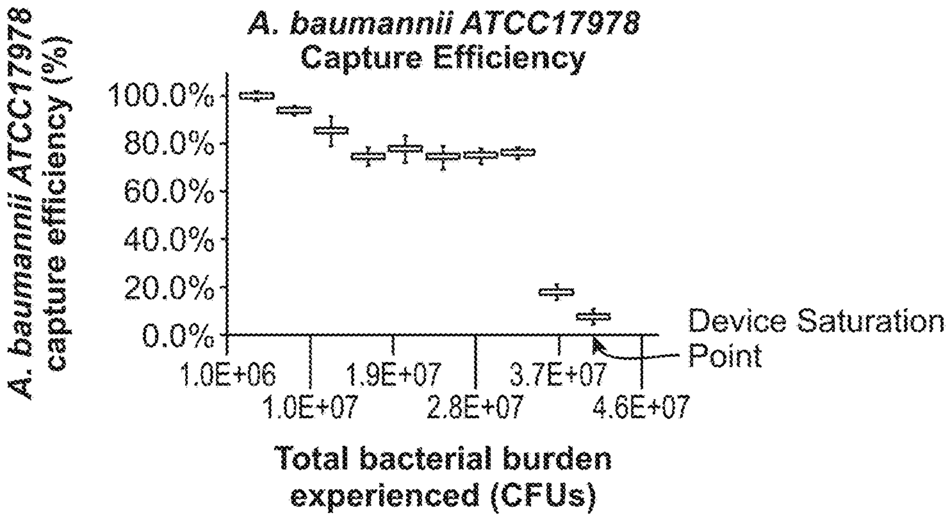
FIG. 10B illustrates the total capture capacity of the device was 2.39E7 CFUs.

FIG. 10A and FIG. 10B show example implementations of a device of the present disclosure to evaluate the bacterial capture capacity a multidirectional fluidic channel using *Acinetobacter baumannii*. FIG. 10A illustrates a capture of *A. baumannii* ATCC 17978 when flowed through the polymyxin coated device (i.e. colistinated device) at 80 ml $min^{-1}$. The *A. baumannii* ATCC 17978 concentration flowed through the device was approximately $10^5$ colony-forming units per milliliter (CFU/mL). No capture was observed within the PEGylated device. n=4, p<0.05*. Bacterial capture capacity, thus, was quantified by flowing *Acinetobacter baumannii* ATCC 17978 suspensions through the colistin coated fluidic device at a flow rate of 80 mL $min^{-1}$. A bacterial cell capture capacity of over $10^7$ colony forming units (CFUs) was achieved with a single passage through the colistinated double spiral fluidic device and a capture efficiency of nearly 100% within the first minute of flow (FIG. 10A and FIG. 10B), as confirmed by the reduction of colonies that could be cultured from the fluid exiting the device. FIG. 10B illustrates the total capture capacity of the device was 2.39E7 CFUs.

Figure 11B:
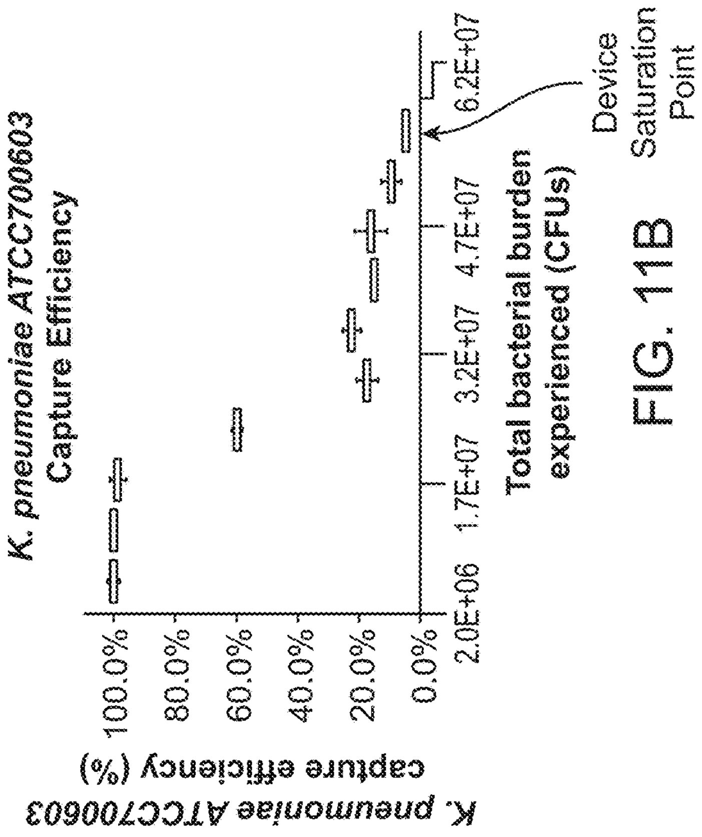
FIG. 11B illustrates the total capture capacity of the device was 1.98E7 CFUs.
Figure 11A:
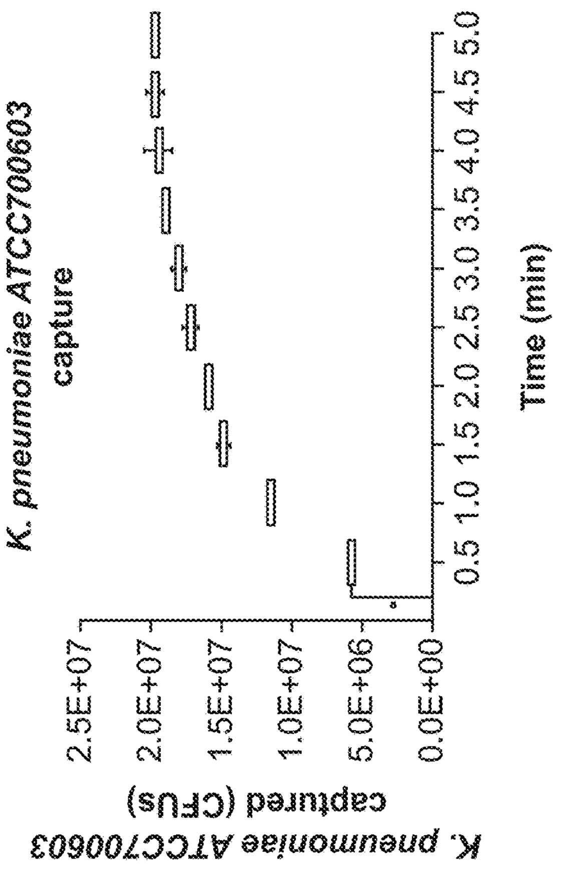
FIG. 11A illustrates a capture of *K. pneumoniae* ATCC 700603 when flowed through the polymyxin E coated device (i.e. colistinated device) at 80 ml $min^{-1}$.

FIG. 11A and FIG. 11B show example implementations of a device of the present disclosure to evaluate the bacterial capture capacity a multidirectional fluidic channel for *Klebsiella pneumoniae*. FIG. 11A illustrates a capture of *K. pneumoniae* ATCC 700603 when flowed through the polymyxin E coated device (i.e. colistinated device) at 80 ml $min^{-1}$. The *K. pneumoniae* ATCC 700603 concentration flowed through the device was approximately $10^5$ CFU/mL. n=4, p<0.05*. *Klebsiella pneumoniae* ATCC 700603, another Gram-negative human pathogen, was also successfully removed from flowing fluid with an associated capture efficiency of nearly 100% within the first minute of flow through the colistinated device (FIG. 11A and FIG. 11B). FIG. 11B illustrates the total capture capacity of the device was 1.98E7 CFUs.

Figure 12B:
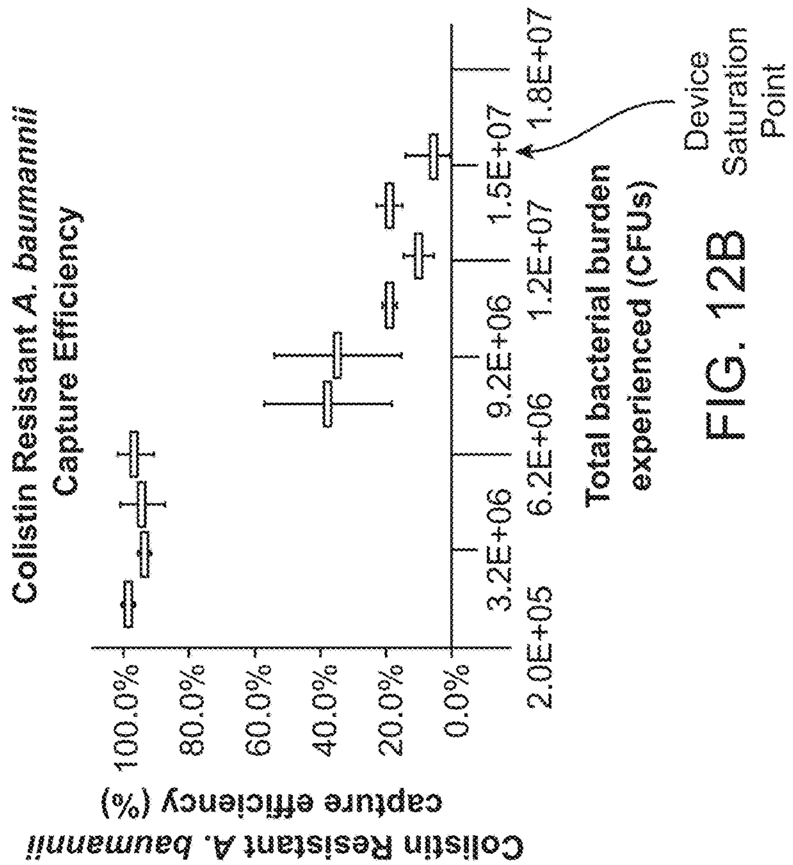
FIG. 12B illustrates the initial capture efficiency was nearly 100%; the total capture capacity of the device was 7.89E6 CFUs.
Figure 12A:
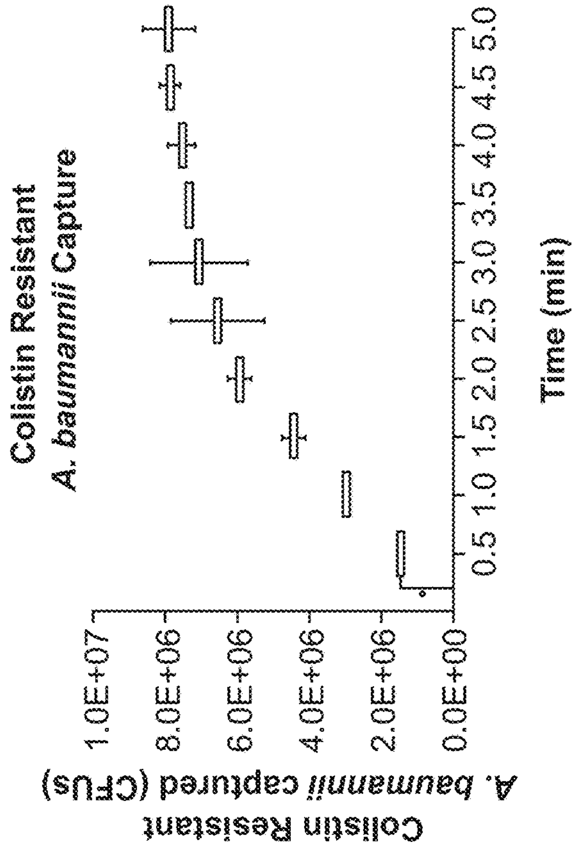
FIG. 12A illustrates the capture of colistin resistant *A. baumannii* when flowed through the polymyxin E coated device (i.e. colistinated device) at 80 ml $min^{-1}$.

FIG. 12A and FIG. 12B show example implementations of a device of the present disclosure to evaluate the bacterial capture capacity a multidirectional fluidic channel using *Acinetobacter baumannii*. The colistinated double spiral fluidic device also captured and removed antibiotic-resistant organisms, including colistin-resistant *A. baumannii* (Qureshi, Z. A. et al. Colistin-resistant *Acinetobacter baumannii*: Beyond carbapenem resistance. *Clin. Infect. Dis.* 60, 1295-1303 (2015)) and colistin-resistant *K. pneumoniae* ATCC 700603, from flowing fluid (FIGS. 12A, 12B, 13A, and 13B). FIG. 12A illustrates the capture of colistin resistant *A. baumannii* when flowed through the polymyxin E coated device (i.e. colistinated device) at 80 ml $min^{-1}$. The colistin resistant *A. baumannii* concentration flowed through the device was approximately $10^4$ CFU/mL, n=4, p<0.05*. FIG. 12B illustrates the initial capture efficiency was nearly 100%; the total capture capacity of the device was 7.89E6 CFUs.

Figure 13A:
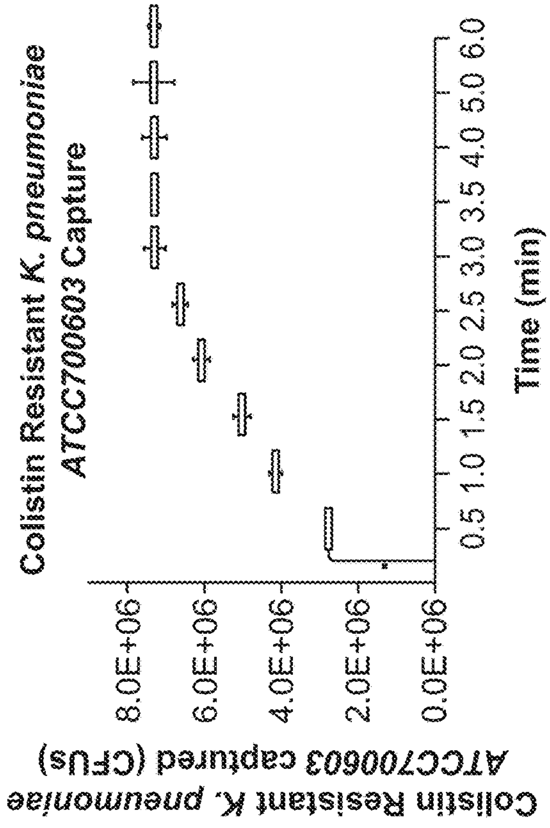
FIG. 13A illustrates the capture of colistin resistant *K. pneumoniae* ATCC 700603 when flowed through the polymyxin E coated device (i.e. colistinated device) at 80 ml $min^{-1}$.
Figure 13B:
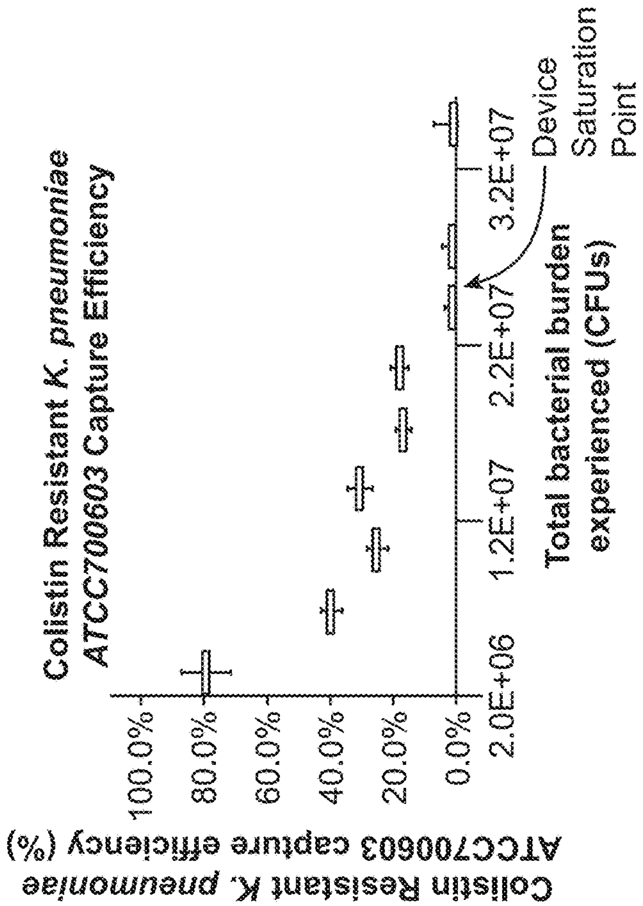
FIG. 13B illustrates the initial capture efficiency was nearly 80%. The total capture capacity of the device was 7.31E6 CFUs.

FIG. 13A and FIG. 13B show example implementations of a device of the present disclosure to evaluate the bacterial capture capacity a multidirectional fluidic channel for *Klebsiella pneumoniae*. FIG. 13A illustrates the capture of colistin resistant *K. pneumoniae* ATCC 700603 when flowed through the polymyxin E coated device (i.e. colistinated device) at 80 ml $min^{-1}$. The colistin resistant *K. pneumoniae* ATCC 700603 concentration flowed through the device was approximately $10^4$ CFU/mL, n=4, p<0.05*. FIG. 13B illustrates the initial capture efficiency was nearly 80%. The total capture capacity of the device was 7.31E6 CFUs.

Figure 14A:
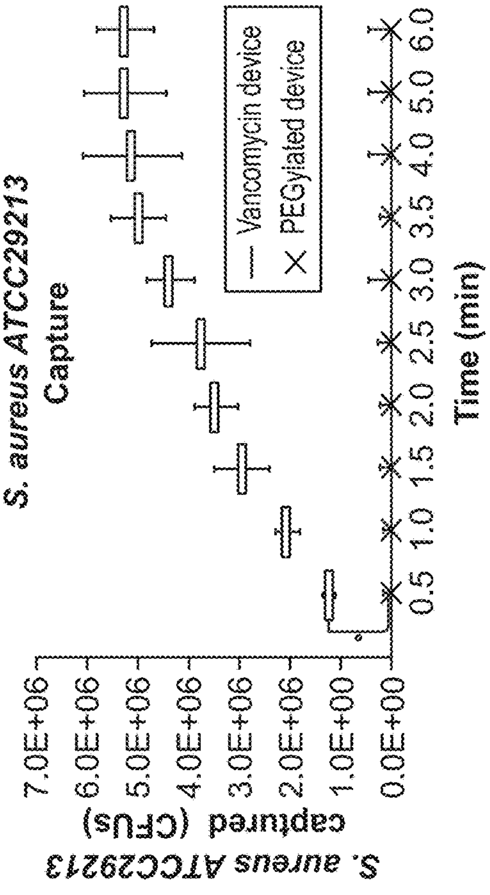
FIG. 14A illustrates the capture of S. aureus ATCC 29213 when flowed through the vancomycin functionalized device at 80 ml $min^{-1}$.
Figure 14B:
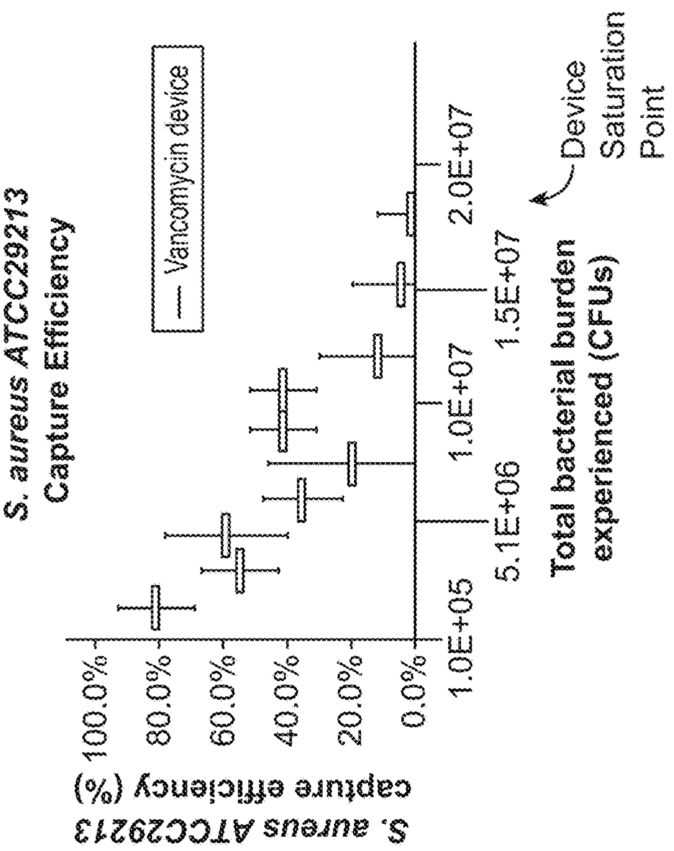
FIG. 14B illustrates the total capture capacity of the device was 5.24E6 CFUs.

FIG. 14A and FIG. 14B show example implementations of a device of the present disclosure to evaluate the bacterial capture capacity a multidirectional fluidic channel for *Staphylococcus aureus*. The vancomycin functionalized double spiral fluidic device captured and removed Gram-positive pathogens from flowing fluid, including *Staphylococcus aureus* ATCC 29213, with a capture efficiency of nearly 80% within the first minute of flow (FIGS. 14A and 14B). FIG. 14A illustrates the capture of *S. aureus* ATCC 29213 when flowed through the vancomycin functionalized device at 80 ml $min^{-1}$. The *S. aureus* ATCC 29213 concentration flowed through the device was approximately $10^4$ CFU/mL. No capture was observed within the PEGylated device. n=4, p<0.05*. FIG. 14B illustrates the total capture capacity of the device was 5.24E6 CFUs. PEGylated devices did not capture Gram-positive *S. aureus* ATCC 29213 or Gram-negative *A. baumannii* ATCC 17978, confirming specificity for pathogens in colistin- and vancomycin-functionalized devices (FIGS. 11B and 14B).

A summary of test data is presented in FIG. 15, which shows the capture capacity of the bacteria adsorbent device using a variety of bacterial strains as described and presented in FIGS. 10A-14B.

Figure 16:
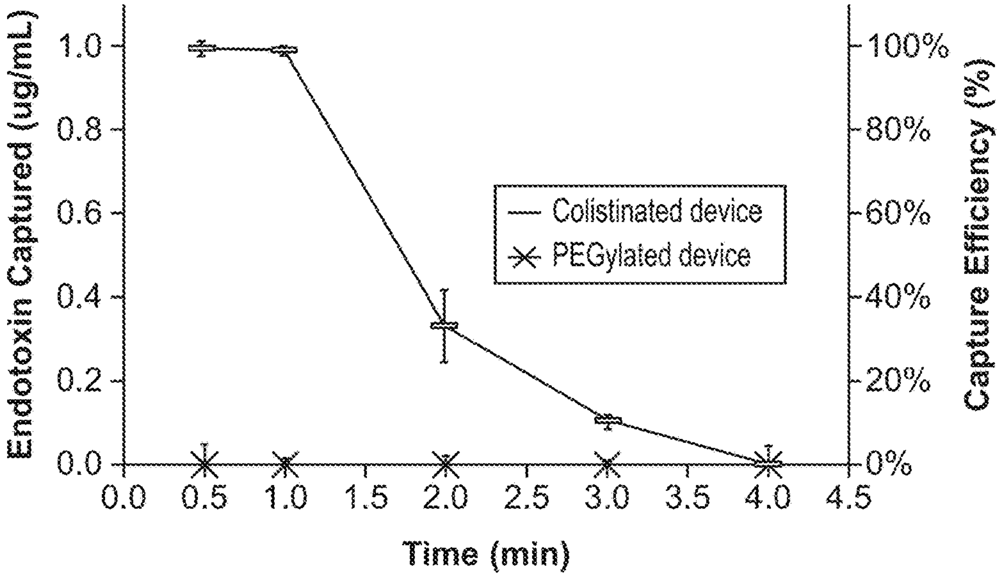
FIG. 16 illustrates that an endotoxin was spiked into endotoxin-free water (1 microgram per milliliter (ug $ml^{-1}$)) and flowed through the polymyxin E coated device (i.e. colistinated device) and PEGylated double spiral fluidic devices at 80 ml $min^{-1}$, the amount of endotoxin captured over time was assessed, and results were plotted as the mean±SD, n=3.

Endotoxin, one of the principal components of the outer membrane of Gram-negative bacteria, also contributes to the systemic inflammatory response that is characteristic of sepsis (Wiesel, P. et al. Endotoxin-induced mortality is related to increased oxidative stress and end-organ dysfunction, not refractory hypotension, in heme oxygenase-1-deficient mice. *Circulation* 102, 3015-3022 (2000)). Therefore, the removal of endotoxin from flowing fluid using embodiments of the multidirectional fluidic device described herein, according to methods herein was assessed. FIG. 16 illustrates that an endotoxin was spiked into endotoxin-free water (1 ug $ml^{-1}$) and flowed through the polymyxin E coated device (i.e. colistinated device) and PEGylated double spiral fluidic devices at 80 ml $min^{-1}$. The amount of endotoxin captured over time was assessed. Results were plotted as the mean±SD, n=3. Endotoxin was rapidly captured from the fluid passing through the colistinated fluidic device, with endotoxin capture efficiency approaching 100% in single pass operation, as shown in FIG. 16. In contrast, endotoxin was not effectively captured using the PEGylated device, demonstrating the critical requirement for colistin in endotoxin adsorption in the multidirectional fluidic device.

FIG. 28 shows a line drawing of an assembled device of the embodiment illustrated in FIG. 22A. Length of Channel—2060 mm (at outer wall): Pitch—3.8 mm: Radius of Curvature—16.5 mm (radius of outer wall): Diameter of Device—44.5 mm (OD of housing): Number of plates—20.

What is claimed is:

1. A device for the capture and adsorption of blood-borne materials of interest, the device comprising:

a fluidic cartridge with at least one inlet and at least one outlet;

two or more filter plates, each filter plate having at least one plate inlet, at least one plate outlet, and a fluidic channel, wherein the fluidic channel comprises a curved shape wherein the fluidic channel is fluidically connected with the at least one plate inlet and the at least one plate outlet, wherein the two or more filter plates are arranged in a stackable plate configuration to collectively form a multidirectional fluidic channel having at least one inner wall, and wherein the multidirectional fluidic channel is fluidically connected with the at least one inlet and the at least one outlet of the fluidic cartridge; and a first substance coating at least a portion of the at least one inner wall of the first multidirectional fluidic channel, wherein the first substance is effective to capture or to adsorb blood-borne materials, wherein a curvature of the multidirectional fluidic channel is configured to promote the capture or the adsorption of the blood-borne materials by the first substance coating the inner wall when the blood-borne materials of interest is flowed through the multidirectional fluidic channel.

2. The device of claim 1, wherein the first substance is selected from the group consisting of: antibodies, crosslinking agents, peptides, proteins, antibiotics, polymers, amines, polyethers, amino acids, aptamers, tumor necrosis factors, adhesion receptors, E-selectin, cytokines, chemotherapy agents, quorum sensing proteins, quorum sensing receptors, and biological agents.

3. The device of claim 2, wherein the first substance comprises a fixed, covalently-bonded antibiotic.

4. The device of claim 3, wherein the fixed, covalently-bonded antibiotic is polymyxin or vancomycin.

5. The device of claim 4, wherein an amount of the polymyxin or the vancomycin is at least 0.5 mM.

6. The device of claim 5, wherein the amount of the polymyxin or the vancomycin is about 1.0 to about 50.0 mM.

7. The device of claim 1, wherein the first substance comprises a fixed crosslinking agent selected from the group consisting of: hexamethylene diamine, polyethylene glycol, polyethylene glycol derivatives, N-hydroxysuccinimide esters, and glycine.

8. The device of claim 1, wherein the multidirectional fluidic channel comprises a thermoplastic polymer base material that has at least one surface exposed functional group selected from the group consisting of: carbonyl groups, carboxyl groups, alcohol groups, amino groups, chloride groups, styrene groups, alpha-halogenated acyl group, benzyl groups, and isocyanic acid groups.

9. The device of claim 1, wherein the multidirectional fluidic channel has a width of about 0.01 to about 1,000.0 mm, wherein the multidirectional fluidic channel has a height of about 0.001 to about 100.0 mm, or wherein the multidirectional fluidic channel has a length of 0.1 to 10,000 mm.

10. The device of claim 1, wherein the multidirectional fluidic channel is spiral or helical shaped.

11. The device of claim 10, wherein a spiral or a-helix of the multidirectional fluidic channel has an outer-most radius of curvature of about 1.0 to about 1,000.0 mm.

12. The device of claim 10, wherein a spiral or a helix of the multidirectional fluidic channel has a distance of about 1.0 to about 10.0 mm between a first portion of the multidirectional fluidic channel and second portion of the multidirectional fluidic channel as measured by a center to center distance between loops of the multidirectional fluidic channel.

13. The device of claim 1, wherein the at least one inlet or the at least one outlet comprises a fitting, a cap, or a luer lock connector to attach the multidirectional fluidic channel to a tubing.

14. The device of claim 1, wherein the stackable plate configuration comprises a number of plates within a range from 2 plates to 25 plates.

15. The device of claim 1, further comprising a second multidirectional fluidic channel comprising at least one inner wall, wherein the first substance coating at least a portion of the at least one inner wall of the first multidirectional fluidic channel comprises a first antibiotic, and wherein a second substance coating at least a portion of the at least one inner wall of the second multidirectional fluidic channel comprises a second antibiotic.

16. The device of claim 15, wherein the first substance and the second substance are different substances.

17. The device of claim 15, wherein the multidirectional fluidic channel comprises a stackable plate configuration; wherein the stackable plate configuration comprises a number of plates within a range from 2 plates to 25 plates; wherein the second multidirectional fluidic channel comprises a stackable plate configuration; and wherein the stackable plate configuration comprises a number of plates within a range from 2 plates to 25 plates.

18. The device of claim 1, wherein the first substance is effective to capture or adsorb one or more of a Gram-negative bacterium, a Gram-positive bacterium, or an endotoxin.

19. The device of claim 1, wherein the first substance is effective to capture or to adsorb a Gram-positive bacterium or a Gram-negative bacterium with a capture capacity of $10^5$ colony forming units or greater.

20. The device of claim 15, wherein the first substance and the second substance are effective to capture or to adsorb a Gram-positive bacterium or a Gram-negative bacterium the blood-borne material with a capture capacity of $10^5$ colony forming units or greater.

21. The device of claim 1, wherein the first substance comprises porous beads.

22. The device of claim 1, wherein the multidirectional fluidic channel comprises heparin disposed therein.

23. The device of claim 1, wherein the multidirectional fluidic channel comprises a thermoplastic polymer base material that is functionalized with a polymer or co-polymer selected from the group consisting of: polycarbonate, vinylchloride, vinylacetate, acrylamide, polyethylene, polyethylene terephthalate acrylic acid, acrylonitrile, maleic anhydride, and methylmethacrylate.

24. The device of claim 1, wherein the first substance comprises a fixed, covalently-bonded polypeptide antibiotic.

25. The device of claim 24, wherein the fixed, covalently-bonded polypeptide antibiotic is polymyxin or colistin.

* * * * *